(12) United States Patent
Min et al.

(10) Patent No.: US 7,332,474 B2
(45) Date of Patent: Feb. 19, 2008

(54) PEPTIDES AND RELATED COMPOUNDS HAVING THROMBOPOIETIC ACTIVITY

(75) Inventors: Hosung Min, Newbury Park, CA (US); Karen C. Sitney, Studio City, CA (US); Cynthia Hartley, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 770 days.

(21) Appl. No.: 10/269,806

(22) Filed: Oct. 10, 2002

(65) Prior Publication Data

US 2003/0176352 A1 Sep. 18, 2003

Related U.S. Application Data

(60) Provisional application No. 60/328,666, filed on Oct. 11, 2001.

(51) Int. Cl.
*A61K 38/00* (2006.01)
(52) U.S. Cl. .......................................... 514/13; 530/326
(58) Field of Classification Search ...................... None
See application file for complete search history.

(56) References Cited

U.S. PATENT DOCUMENTS

| | | | |
|---|---|---|---|
| 3,691,016 A | 9/1972 | Patel | |
| 3,941,763 A | 3/1976 | Sarantakis | |
| 3,969,287 A | 7/1976 | Jaworek et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,289,872 A | 9/1981 | Denkewalter et al. | |
| 4,330,440 A | 5/1982 | Ayers et al. | |
| 4,925,673 A | 5/1990 | Steiner et al. | |
| 5,013,556 A | 5/1991 | Woodle et al. | |
| 5,223,409 A | 6/1993 | Ladner et al. | |
| 5,229,490 A | 7/1993 | Tam | |
| 5,284,656 A | 2/1994 | Platz et al. | |
| 5,338,665 A | 8/1994 | Schatz et al. | |
| 5,428,130 A | 6/1995 | Capon et al. | |
| 5,432,018 A | 7/1995 | Dower et al. | |
| 5,480,981 A | 1/1996 | Goodwin et al. | |
| 5,498,530 A | 3/1996 | Schatz et al. | |
| 5,733,731 A | 3/1998 | Schatz et al. | |
| 5,739,277 A | 4/1998 | Presta et al. | |
| 5,792,451 A | 8/1998 | Sarubbi et al. | |
| 5,869,451 A * | 2/1999 | Dower et al. ................. | 514/13 |
| 5,922,545 A | 7/1999 | Mattheakis et al. | |
| 5,932,546 A | 8/1999 | Barrett et al. | |

FOREIGN PATENT DOCUMENTS

| | | |
|---|---|---|
| WO | WO93/21259 | 10/1993 |
| WO | WO95/18858 | 7/1995 |
| WO | WO95/21919 | 8/1995 |
| WO | WO95/21920 | 8/1995 |
| WO | WO95/26746 | 10/1995 |
| WO | WO96/32478 | 10/1996 |
| WO | WO96/40189 | 12/1996 |
| WO | WO96/40750 | 12/1996 |
| WO | WO96/40772 | 12/1996 |
| WO | WO96/40987 | 12/1996 |
| WO | WO97/34631 | 9/1997 |
| WO | WO98/15833 | 4/1998 |
| WO | WO98/25965 | 6/1998 |
| WO | WO 00/24770 | 5/2000 |
| WO | WO 00/24782 | 5/2000 |

OTHER PUBLICATIONS

Rudikoff, et al., Proc. Natl. Acad. Sci., 1982, 79, 1979-1983.*
Abuchowski et al., Enzymes as Drugs: Chapter 13, Soluble Polymer-Enzyme Adducts, Hocenberg and Roberts, eds., Wiley-Interscience, New York, NY. pp. 367-383 (1981).
Adjei et al., Pharmaceutical Research 7:565-569 (1990).
Adjei et al., International Journal of Pharmaceutics 61:135-144 (1990).
Alexander et al., Blood 87:2162-2170 (1996).
Bartley et al., Cell 77:1117-1124 (1994).
Basser et al., The Lancet 348:1279-1281 (1996).
Braquet et al., Journal of Cardiovascular Pharmacology, 13 (Suppl. 5):S143-S146 (1989).
Capon et al., Nature 337:525-531 (1989).
Chang et al., The Journal of Biological Chemistry 270:511-514 (1995).
Choi et al., Blood 85:402-413 (1995).
Clackson et al., Science 267:383-386 (1995).
Creighton, Thomas E., Proteins: Structures and Molecular Principles, W.H. Freeman and Company, New York, pp. 70-86 (1983).
Cwirla et al., Science 276:1696-1699 (1997).
Davis et al., Biochemistry International 10:395-404 (1985).
Debili et al., Blood 85:391-401 (1995).
Debs et al., The Journal of Immunology 140:3482-3488 (1988).
de Sauvage et al., Nature 369:533-538 (1994).
Devlin et al., Science 249:404-406 (1990).
Duncan et al., Nature 332:563-564 (1988).
Ellison et al., Nucleic Acids Research 10:4071-4079 (1982).
Erickson et al., The Proteins, $3^{rd}$ ed., 2: Chapter 3, Solid-Phase Peptide Synthesis, Neurath et al., eds., Academic Press, New York, pp. 255-527 (1976).
Finn et al., The Proteins, $3^{rd}$ ed., 2: Chapter 3, Solid-Phase Peptide Synthesis, Neurath et al., eds., Academic Press, New York, pp. 255-527 (1976).
Fisher et al., The New England Journal of Medicine 334:1697-1702 (1996).
Francis, Gillian E., Guest Review: Protein modication and fusion proteins, Royal Free Hospital School of Medicine, London, UK, pp. 4-10.

(Continued)

*Primary Examiner*—Anish Gupta
*Assistant Examiner*—Satyanarayana R. Gudibande
(74) *Attorney, Agent, or Firm*—Robert T. Ramos

(57) ABSTRACT

The present invention relates generally to novel peptides and related compounds that have thrombopoietic activity. The compounds of the invention may be used to increase production of platelets or platelet precursors (e.g. megakaryocytes) in a mammal.

5 Claims, 30 Drawing Sheets

OTHER PUBLICATIONS

Gurney et al., Blood 85:981-988 (1995).
Harvill et al., Immunotechnology 1:95-105 (1995).
Hokom et al., Blood 86:4486-4492 (1995).
Hubbard et al., Annals of Internal Medicine 111:206-212 (1989).
Jefferis et al., Molecular Immunology 27:1237-1240 (1990).
Jefferis et al., Immunology Letters 44:111-117 (1995).
Johnson et al., Biochemistry 37:3699-3710 (1998).
Kato et al., Journal of Biochemistry 118:229-236 (1995).
Kaushansky et al., Nature 369:568-571 (1994).
Kay et al., Reviews—Research Focus 3:370-378 (1998).
Kimura et al., Journal of Biochemistry, Molecular Biology & Biophysics 2:281-286 (1999).
Kuter et al., Proceedings from the National Academy of Sciences USA 91:11104-11108 (1994).
Livnah et al., Science 273:464-471 (1996).
Lok et al., Nature 369:565-568 (1994).
Lowman, H.B., Annual Review of Biomolecular Structures 26:401-424 (1997).
Marshall, Keith, Modern Pharmaceutics, Chapter 10: Solid Oral Dosage Forms, G.S. Banker and C.T. Rhodes eds., School of Pharmacy, University of Bradford, Bradford, Yorkshire, England, pp. 359-427 (1979).
Merrifield, R.B., Journal of the American Chemical Society 85:2149-2154 (1963).
Merrifield R.B., Chemical Polypeptides, Chapter 16:Solid Phase Peptide Synthesis, Katsoyannis and Panayotis eds., Rockefeller University, New York, pp. 335-361 (1973).
Methia et al., Blood 82:1395-1401 (1993).
Newmark et al., Journal of Applied Biochemistry 4:185-189 (1982).
Palacios et al., Cell 41:727-734 (1985).
Rasko et al., Stem Cells 15:33-42 (1997).
Ravin et al., Remington Pharmaceutical Sciences, 18$^{th}$ ed., Chapter 75: Preformulation, pp. 1435-1712 (1990).
Roberts et al., Proceedings from the National Academy of Sciences USA 94:12297-12302 (1997).
Sarmay et al., Molecular Immunology 29:633-639 (1992).
Scott et al., Science 249:386-390 (1990).
Sheridan et al., Platelets 8:319-332 (1997).
Smith et al., Journal of Clinical Investigation 84:1145-1154 (1989).
Stewart et al., Solid Phase Peptide Synthesis: Table of Contents and Indexes only, W.H. Freeman and Company, San Francisco (1969).
Syed et al., Nature 395:511-516 (1998).
Takasaki et al., Nature Biotechnology 15:1266-1270 (1997).
Ulich et al., Blood 86: 971-976 (1995).
Van Zee et al., The Journal of Immunology 156:2221-2230 (1996).
Vignon et al., Proceedings from the National Academy of Sciences USA 89:5640-5644 (1992).
Wells et al., Current Opinion in Biotechnology 3:355-362 (1992).
Wells et al., Annual Review of Biochemistry 65:609-634 (1996).
Whitty et al., Chemistry & Biology 6:R107-R118 (1999).
Wrighton et al., Science 273:458-463 (1996).
Wrighton et al., Nature Biotechnology 15:1261-1265 (1997).
Zeigler et al. Blood 84:4045-4052 (1994).
Zheng et al., The Journal of Immunology 154:5590-5600 (1995).

* cited by examiner

FIGURE 1

| TMP1<br><br>1A. | TMP1-TMP2<br><br>(C-terminus of TMP1 to N-terminus of TMP2)<br><br>1B. | TMP1-LN1-TMP1<br><br>1C. |
|---|---|---|
| TMP1-LN1-TMP2-LN2<br><br>1D. | TMP1-TMP2-TMP3-TMP4-TMP5<br><br>1E. | TMP1-LN1-TMP1 ⎤<br>TMP2-LN2-TMP2 ⎦<br><br>1F. |
| $(TMP1)_x$-LN1<br><br>1G. | $(TMP1-LN1)_x$<br><br>1H. | TMP1 ⎤<br>TMP2 ⎦<br><br>(C-terminus of TMP1 to C-terminus of TMP2)<br><br>1I. |
| ⎡ TMP1<br>⎣ TMP1<br>(N-terminus of TMP1 to N-terminus of TMP2)<br><br>1J. | TMP1-LN1 ⎤<br>TMP2-LN2 ⎦<br><br>1K. | ⎡ TMP1-LN1-TMP2<br>⎣ TMP3-LN2-TMP1<br><br>1L. |

Figure 2

| | | |
|---|---|---|
| TMP1-V1<br><br>2A. | V1-TMP1<br><br>2B. | V1-TMP1-LN1-TMP2<br><br>2C. |
| TMP1-LN1-V1<br><br>2D. | TMP1-TMP2-V1<br><br>2E. | V1-TMP1 ⎤<br>         ⎥<br>TMP2    ⎦<br><br>2F. |
| ⎡ TMP1-V1<br>⎣ TMP2<br><br>2G. | V1-LN1-TMP1-LN2-TMP2<br><br>2H. | TMP1-LN1-TMP1-LN1-V1<br><br>2I. |
| V1-TMP1-V2<br><br>2J. | V1-TMP2-TMP2-TMP2-V1<br><br>2K. | V1-TMP1  ⎤<br>         ⎥<br>V2-TMP2  ⎦<br><br>2L. |

Figure 3

```
     ATGGACAAAACTCACACATGTCCACCTTGTCCAGCTCCGGAACTCCTGGGGGGACCGTCA
   1 ------------+----------+----------+----------+----------+----------+ 60
     TACCTGTTTTGAGTGTGTACAGGTGGAACAGGTCGAGGCCTTGAGGACCCCCCTGGCAGT
a    M  D  K  T  H  T  C  P  P  C  P  A  P  E  L  L  G  G  P  S    -

GTCTTCCTCTTCCCCCCAAAAACCCAAGGACACCCTCATGATCTCCCGGACCCCTGAGGTC
  61 ------------+----------+----------+----------+----------+----------+ 120
     CAGAAGGAGAAGGGGGGTTTTGGGTTCCTGTGGGAGTACTAGAGGGCCTGGGGACTCCAG
a    V  F  L  F  P  P  K  P  K  D  T  L  M  I  S  R  T  P  E  V    -

ACATGCGTGGTGGTGGACGTGAGCCACGAAGACCCTGAGGTCAAGTTCAACTGGTACGTG
 121 ------------+----------+----------+----------+----------+----------+ 180
     TGTACGCACCACCACCTGCACTCGGTGCTTCTGGGACTCCAGTTCAAGTTGACCATGCAC
a    T  C  V  V  V  D  V  S  H  E  D  P  E  V  K  F  N  W  Y  V    -

GACGGCGTGGAGGTGCATAATGCCAAGACAAAGCCGCGGGAGGAGCAGTACAACAGCACG
 181 ------------+----------+----------+----------+----------+----------+ 240
     CTGCCGCACCTCCACGTATTACGGTTCTGTTTCGGCGCCCTCCTCGTCATGTTGTCGTGC
a    D  G  V  E  V  H  N  A  K  T  K  P  R  E  E  Q  Y  N  S  T    -

TACCGTGTGGTCAGCGTCCTCACCGTCCTGCACCAGGACTGGCTGAATGGCAAGGAGTAC
 241 ------------+----------+----------+----------+----------+----------+ 300
     ATGGCACACCAGTCGCAGGAGTGGCAGGACGTGGTCCTGACCGACTTACCGTTCCTCATG
a    Y  R  V  V  S  V  L  T  V  L  H  Q  D  W  L  N  G  K  E  Y    -

AAGTGCAAGGTCTCCAACAAAGCCCTCCCAGCCCCCATCGAGAAAACCATCTCCAAAGCC
 301 ------------+----------+----------+----------+----------+----------+ 360
     TTCACGTTCCAGAGGTTGTTTCGGGAGGGTCGGGGGTAGCTCTTTTGGTAGAGGTTTCGG
a    K  C  K  V  S  N  K  A  L  P  A  P  I  E  K  T  I  S  K  A    -

AAAGGGCAGCCCCGAGAACCACAGGTGTACACCCTGCCCCCATCCCGGGATGAGCTGACC
 361 ------------+----------+----------+----------+----------+----------+ 420
     TTTCCCGTCGGGGCTCTTGGTGTCCACATGTGGGACGGGGGTAGGGCCCTACTCGACTGG
a    K  G  Q  P  R  E  P  Q  V  Y  T  L  P  P  S  R  D  E  L  T    -

AAGAACCAGGTCAGCCTGACCTGCCTGGTCAAAGGCTTCTATCCCAGCGACATCGCCGTG
 421 ------------+----------+----------+----------+----------+----------+ 480
     TTCTTGGTCCAGTCGGACTGGACGGACCAGTTTCCGAAGATAGGGTCGCTGTAGCGGCAC
a    K  N  Q  V  S  L  T  C  L  V  K  G  F  Y  P  S  D  I  A  V    -

GAGTGGGAGAGCAATGGGCAGCCGGAGAACAACTACAAGACCACGCCTCCCGTGCTGGAC
 481 ------------+----------+----------+----------+----------+----------+ 540
     CTCACCCTCTCGTTACCCGTCGGCCTCTTGTTGATGTTCTGGTGCGGAGGGCACGACCTG
a    E  W  E  S  N  G  Q  P  E  N  N  Y  K  T  T  P  P  V  L  D    -

TCCGACGGCTCCTTCTTCCTCTACAGCAAGCTCACCGTGGACAAGAGCAGGTGGCAGCAG
 541 ------------+----------+----------+----------+----------+----------+ 600
     AGGCTGCCGAGGAAGAAGGAGATGTCGTTCGAGTGGCACCTGTTCTCGTCCACCGTCGTC
a    S  D  G  S  F  F  L  Y  S  K  L  T  V  D  K  S  R  W  Q  Q    -

GGGAACGTCTTCTCATGCTCCGTGATGCATGAGGCTCTGCACAACCACTACACGCAGAAG
 601 ------------+----------+----------+----------+----------+----------+ 660
     CCCTTGCAGAAGAGTACGAGGCACTACGTACTCCGAGACGTGTTGGTGATGTGCGTCTTC
a    G  N  V  F  S  C  S  V  M  H  E  A  L  H  N  H  Y  T  Q  K    -

AGCCTCTCCCTGTCTCCGGGTAAA
 661 ------------+----------+----       684        [SEQ ID NO. 31] (Nucleic Acid)
     TCGGAGAGGGACAGAGGCCCATTT
a    S  L  S  L  S  P  G  K              [SEQ ID NO. 32] (Amino Acid
```

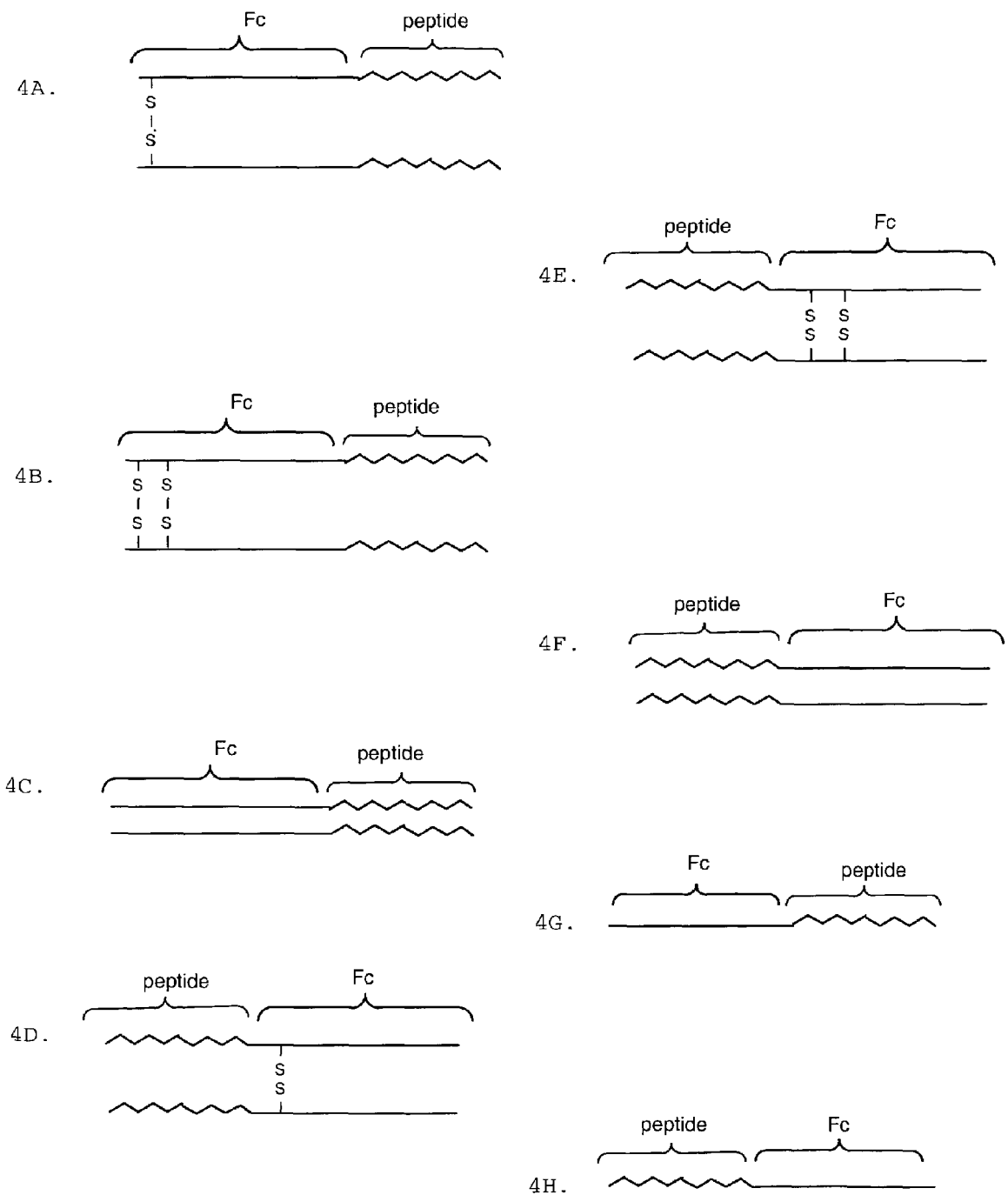

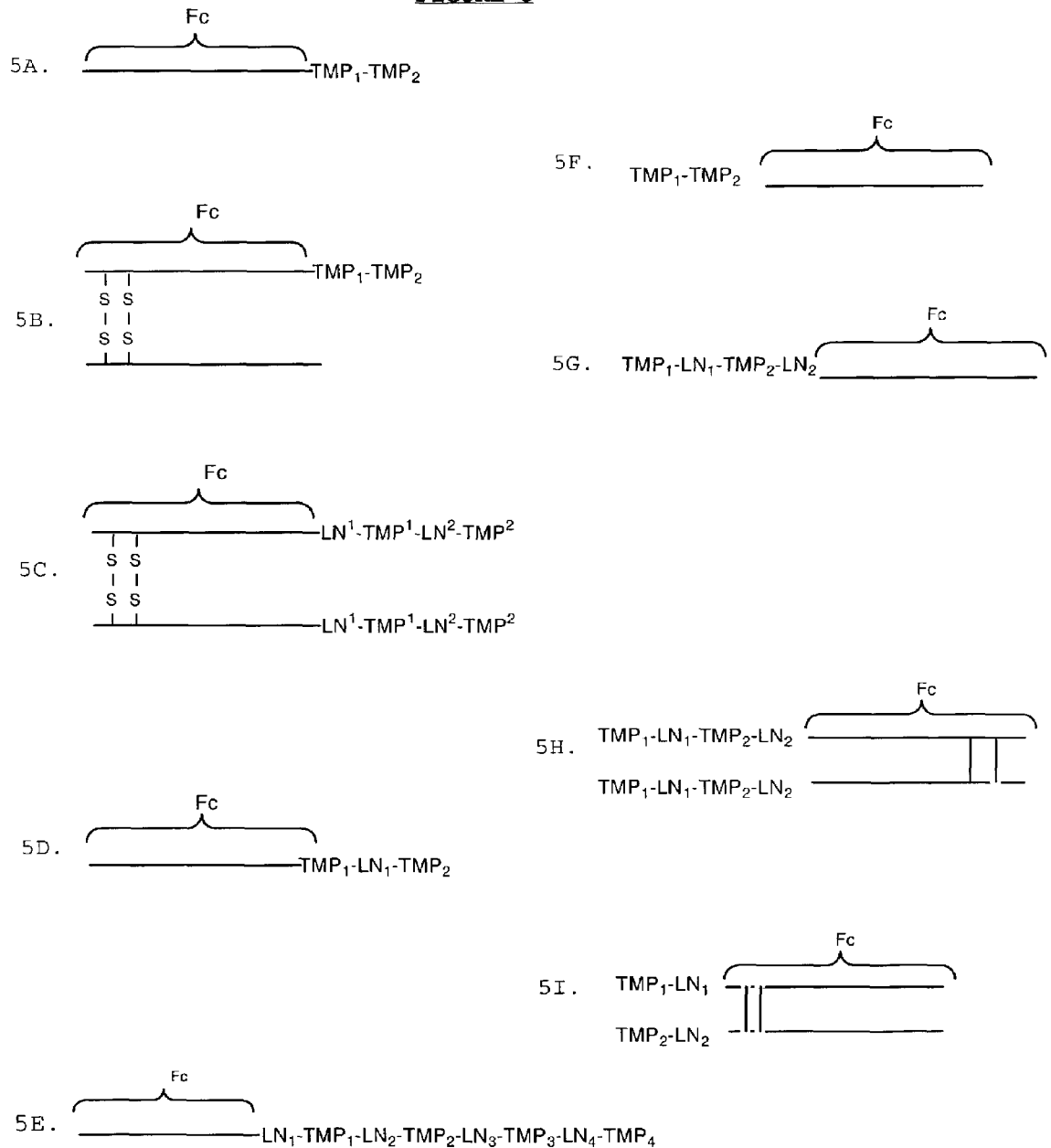

FIGURE 6A

200003180 vector

```
                                                           NdeI
                                                            |
    TAGTCGATTAATCGATTTGATTCTAGATTTGTTTTAACTAATTAAAGGAGGAATAACATA
  1 ---------+---------+---------+---------+---------+---------+ 60
    ATCAGCTAATTAGCTAAACTAAGATCTAAACAAAATTGATTAATTTCCTCCTTATTGTAT

M
    ApaLI                XhoI
      |                    |
      TGGGTGCACAGAAAGCGGCCGCAAAAAAACTCGAGGGTGGAGGCGGTGGGGACAAAACTC
   61 ---------+---------+---------+---------+---------+---------+ 120
      ACCCACGTGTCTTTCGCCGGCGTTTTTTTGAGCTCCCACCTCCGCCACCCCTGTTTTGAG c      G  A  Q  K  A  A  A  K  K  L  E  G  G  G  G  D  K  T  H -
                                                      |--Fc----->

ACACATGTCCACCTTGCCCAGCACCTGAACTCCTGGGGGGACCGTCAGTTTTCCTCTTCC
  121 ---------+---------+---------+---------+---------+---------+ 180
      TGTGTACAGGTGGAACGGGTCGTGGACTTGAGGACCCCCCTGGCAGTCAAAAGGAGAAGG c      T  C  P  P  C  P  A  P  E  L  L  G  G  P  S  V  F  L  F  P -

CCCCAAAACCCAAGGACACCCTCATGATCTCCCGGACCCCTGAGGTCACATGCGTGGTGG
  181 ---------+---------+---------+---------+---------+---------+ 240
      GGGGTTTTGGGTTCCTGTGGGAGTACTAGAGGGCCTGGGGACTCCAGTGTACGCACCACC c      P  K  P  K  D  T  L  M  I  S  R  T  P  E  V  T  C  V  V  V -

TGGACGTGAGCCACGAAGACCCTGAGGTCAAGTTCAACTGGTACGTGGACGGCGTGGAGG
  241 ---------+---------+---------+---------+---------+---------+ 300
      ACCTGCACTCGGTGCTTCTGGGACTCCAGTTCAAGTTGACCATGCACCTGCCGCACCTCC c      D  V  S  H  E  D  P  E  V  K  F  N  W  Y  V  D  G  V  E  V -

TGCATAATGCCAAGACAAAGCCGCGGGAGGAGCAGTACAACAGCACGTACCGTGTGGTCA
  301 ---------+---------+---------+---------+---------+---------+ 360
      ACGTATTACGGTTCTGTTTCGGCGCCCTCCTCGTCATGTTGTCGTGCATGGCACACCAGT c      H  N  A  K  T  K  P  R  E  E  Q  Y  N  S  T  Y  R  V  V  S -

GCGTCCTCACCGTCCTGCACCAGGACTGGCTGAATGGCAAGGAGTACAAGTGCAAGGTCT
  361 ---------+---------+---------+---------+---------+---------+ 420
      CGCAGGAGTGGCAGGACGTGGTCCTGACCGACTTACCGTTCCTCATGTTCACGTTCCAGA c      V  L  T  V  L  H  Q  D  W  L  N  G  K  E  Y  K  C  K  V  S -

CCAACAAAGCCCTCCCAGCCCCCATCGAGAAAACCATCTCCAAAGCCAAAGGGCAGCCCC
  421 ---------+---------+---------+---------+---------+---------+ 480
      GGTTGTTTCGGGAGGGTCGGGGGTAGCTCTTTTGGTAGAGGTTTCGGTTTCCCGTCGGGG c      N  K  A  L  P  A  P  I  E  K  T  I  S  K  A  K  G  Q  P  R -
```

FIGURE 6B

```
             BsrGI
              |
     GAGAACCACAGGTGTACACCCTGCCCCCATCCCGGGATGAGCTGACCAAGAACCAGGTCA
481  ---------+---------+---------+---------+---------+---------+ 540
     CTCTTGGTGTCCACATGTGGGACGGGGGTAGGGCCCTACTCGACTGGTTCTTGGTCCAGT c       E   P   Q   V   Y   T   L   P   P   S   R   D   E   L   T   K   N   Q   V   S -

GCCTGACCTGCCTGGTCAAAGGCTTCTATCCCAGCGACATCGCCGTGGAGTGGGAGAGCA
541  ---------+---------+---------+---------+---------+---------+ 600
     CGGACTGGACGGACCAGTTTCCGAAGATAGGGTCGCTGTAGCGGCACCTCACCCTCTCGT c       L   T   C   L   V   K   G   F   Y   P   S   D   I   A   V   E   W   E   S   N -

ATGGGCAGCCGGAGAACAACTACAAGACCACGCCTCCCGTGCTGGACTCCGACGGCTCCT
601  ---------+---------+---------+---------+---------+---------+ 660
     TACCCGTCGGCCTCTTGTTGATGTTCTGGTGCGGAGGGCACGACCTGAGGCTGCCGAGGA c       G   Q   P   E   N   N   Y   K   T   T   P   P   V   L   D   S   D   G   S   F -

TCTTCCTCTACAGCAAGCTCACCGTGGACAAGAGCAGGTGGCAGCAGGGGAACGTCTTCT
661  ---------+---------+---------+---------+---------+---------+ 720
     AGAAGGAGATGTCGTTCGAGTGGCACCTGTTCTCGTCCACCGTCGTCCCCTTGCAGAAGA c       F   L   Y   S   K   L   T   V   D   K   S   R   W   Q   Q   G   N   V   F   S -

CATGCTCCGTGATGCATGAGGCTCTGCACAACCACTACACGCAGAAGAGCCTCTCCCTGT
721  ---------+---------+---------+---------+---------+---------+ 780
     GTACGAGGCACTACGTACTCCGAGACGTGTTGGTGATGTGCGTCTTCTCGGAGAGGGACA c       C   S   V   M   H   E   A   L   H   N   H   Y   T   Q   K   S   L   S   L   S -

BamHI
                  |
     CTCCGGGTAAATAATGGATCCGCGGAAAGAAGAAGAAGAAGAAGAAAGCCCGAAA
781  ---------+---------+---------+---------+---------+----- 835
     GAGGCCCATTTATTACCTAGGCGCCTTTCTTCTTCTTCTTCTTTCGGGCTTT c       P   G   K   *
```

[SEQ ID NO. 33] (Nucleic Acid)

[SEQ ID NO. 34] (Amino Acid)

FIGURE 7A
TMP1 [SEQ ID NOS. 35, 36]

```
    NdeI ApaLI
     |   |
    CATATGGGTGCACAGGGTATCGAAGGTCCGACTCTGCGTCAGTGGCTGGCTGCTCGTGCT
1 ------+---------+---------+---------+---------+---------+--- 60
    GTATACCCACGTGTCCCATAGCTTCCAGGCTGAGACGCAGTCACCGACCGACGAGCACGA
a      M G A Q G I E G P T L R Q W L A A R A -

XhoI
        |
       CTCGAG
61 ------
       GAGCTC
a      L E
```

FIGURE 7B
TMP2 [SEQ ID NOS. 37-40]

2465-33  TGC ACA AGG TGG AGC ACG TGA AGG ACC AAC TCT TCG TCA ATG
         GCT TGA ATG GGT TCG TGT TGG TCA TTC TC 2465-34  TCG AGA GAA TGA CCA ACA CGA ACC CAT TCA AGC CAT TGA CGA
         AGA GTT GGT CCT TCA CGT GCT CCA CCT TG

```
      ApaLI
       |
      GTGCACAAGGTGGAGCACGTGAAGGACCAACTCTTCGTCAATGGCTTGAATGGGTTCGTG
1 ---------+---------+---------+---------+---------+---------+ 60
      CACGTGTTCCACCTCGTGCACTTCCTGGTTGAGAAGCAGTTACCGAACTTACCCAAGCAC
c     A Q G G A R E G P T L R Q W L E W V R V -

XhoI
           |
          TTGGTCATTCTCTCGAG
61 ---------+------ 77
          AACCAGTAAGAGAGCTC
c         G H S L E -
```

FIGURE 7C

TMP3 [SEQ ID NOS. 41 - 44]

2465-35  TGC ACA AGG ACG TGA TCT TGA TGG TCC AAC TCT TCG TCA ATG
        GCT TCC ACT TCC ATC TGT TCA ACA TTC TC 2465-36  TCG AGA GAA TGT TGA ACA GAT GGA AGT GGA AGC CAT TGA CGA
        AGA GTT GGA CCA TCA AGA TCA CGT CCT TG

```
          ApaLI
            |
GTGCACAAGGACGTGATCTTGATGGTCCAACTCTTCGTCAATGGCTTCCACTTCCATCTG
1 --------+---------+---------+---------+---------+---------+ 60
CACGTGTTCCTGCACTAGAACTACCAGGTTGAGAAGCAGTTACCGAAGGTGAAGGTAGAC
c     A Q G R D L D G P T L R Q W L P L P S V -
```

```
           XhoI
             |
         TTCAACATTCTCTCGAG
       61 --------+------- 77
         AAGTTGTAAGAGAGCTC
c         Q H S L E -
```

FIGURE 7D

TMP4 [SEQ ID NOS. 45 - 48]

2467-21  TGC ACA AGG AGC TTT ACG TGA TGG TCC AAC TCT TAA ACA ATG
        GTT AGA ATA TCG TCG TCA AGC TCA TTC AC 2467-22  TCG AGT GAA TGA GCT TGA CGA CGA TAT TCT AAC CAT TGT TTA
        AGA GTT GGA CCA TCA CGT AAA GCT CCT TG

```
          ApaLI
            |
GTGCACAAGGAGCTTTACGTGATGGTCCAACTCTTAAACAATGGTTAGAATATCGTCGTC
1 --------+---------+---------+---------+---------+---------+ 60
CACGTGTTCCTCGAAATGCACTACCAGGTTGAGAATTTGTTACCAATCTTATAGCAGCAG
c     A Q G A L R D G P T L K Q W L E Y R R Q -
```

```
           XhoI
             |
         AAGCTCATTCACTCGAG
       61 --------+------ 77
         TTCGAGTAAGTGAGCTC
c         A H S L E -
```

FIGURE 7E

TMP5 [SEQ ID NOS. 49-52]

2467-23  TGC ACA AGG AGC ACG TCA AGA AGG ACC AAC TCT TAA AGA ATG
GTT ATT TTG GGT TCG TAT GGG TCA TTC AC 2467-24  TCG AGT GAA TGA CCC ATA CGA ACC CAA AAT AAC CAT TCT TTA
AGA GTT GGT CCT TCT TGA CGT GCT CCT TG

```
       ApaLI
         |
     GTGCACAAGGAGCACGTCAAGAAGGACCAACTCTTAAAGAATGGTTATTTTGGGTTCGTA
     1 ----+----+----+----+----+----+ 60
     CACGTGTTCCTCGTGCAGTTCTTCCTGGTTGAGAATTTCTTACCAATAAAACCCAAGCAT
   c    A Q G A R Q E G P T L K E W L F W V R M -

XhoI
                |
         TGGGTCATTCACTCGAG
       61 ----+---- 77
         ACCCAGTAAGTGAGCTC
       c  G H S L E -
```

FIGURE 7F

TMP6 [SEQ ID NOS. 53-56]

2468-14  TGC ACA AGG AGA AGC TTT ATT AGG TCC AAC TTT ACG TGA ATG
GCT TGC TTG GCG TCG TGC ACA ACA TTC TC 2468-15  TCG AGA GAA TGT TGT GCA CGA CGC CAA GCA AGC CAT TCA CGT
AAA GTT GGA CCT AAT AAA GCT TCT CCT TG

```
       ApaLI
         |
     GTGCACAAGGAGAAGCTTTATTAGGTCCAACTTTACGTGAATGGCTTGCTTGGCGTCGTG
     1 ----+----+----+----+----+----+ 60
     CACGTGTTCCTCTTCGAAATAATCCAGGTTGAAATGCACTTACCGAACGAACCGCAGCAC
   c    A Q G E A L L G P T L R E W L A W R R A -

XhoI
                |
         CACAACATTCTCTCGAG
       61 ----+---- 77
         GTGTTGTAAGAGAGCTC
       c  Q H S L E -
```

FIGURE 7G

TMP7 [SEQ ID NOS. 57-60]

2468-16  TGC ACA AGG TAT GGC ACG TGA TGG TCC AAC TCT TCG TGA ATG
        GCT TCG TAC TTA TCG TAT GAT GCA TTC TC 2468-17  TCG AGA GAA TGC ATC ATA CGA TAA GTA CGA AGC CAT TCA CGA
        AGA GTT GGA CCA TCA CGT GCC ATA CCT TG

```
          ApaLI
            |
GTGCACAAGGTATGGCACGTGATGGTCCAACTCTTCGTGAATGGCTTCGTACTTATCGTA
1 --------+---------+---------+---------+---------+--------+ 60
CACGTGTTCCATACCGTGCACTACCAGGTTGAGAAGCACTTACCGAAGCATGAATAGCAT
c    A  Q  G  M  A  R  D  G  P  T  L  R  E  W  L  R  T  Y  R  M -
```

```
          XhoI
            |
         TGATGCATTCTCTCGAG
61 ------+------ 77
         ACTACGTAAGAGAGCTC
c         M  H  S  L  E -
```

FIGURE 7H

TMP8 [SEQ ID NOS. 61-64]

2469-10  TGC ACA AGG ATG GAT GCC AGA AGG ACC AAC ATT AAA ACA ATG
        GCT TTT TCA TGG TCG TGG TCA ACA TTC TC 2469-11  TCG AGA GAA TGT TGA CCA CGA CCA TGA AAA AGC CAT TGT TTT
        AAT GTT GGT CCT TCT GGC ATC CAT CCT TG

```
          ApaLI
            |
GTGCACAAGGATGGATGCCAGAAGGACCAACATTAAAACAATGGCTTTTTCATGGTCGTG
1 --------+---------+---------+---------+---------+--------+ 60
CACGTGTTCCTACCTACGGTCTTCCTGGTTGTAATTTTGTTACCGAAAAAGTACCAGCAC
c    A  Q  G  W  M  P  E  G  P  T  L  K  Q  W  L  F  H  G  R -
```

```
          XhoI
            |
         GTCAACATTCTCTCGAG
61 --------+------ 77
         CAGTTGTAAGAGAGCTC
c         Q  H  S  L  E -
```

FIGURE 7I

TMP9 [SEQ ID NOS. 65-68]

2469-12  TGC ACA AGG ACA TAT TCG TGA AGG TCC AAC ATT ACG TCA ATG
        GCT TGT TGC TCT TCG TAT GGT TCA TTC TC 2469-13  TCG AGA GAA TGA ACC ATA CGA AGA GCA ACA AGC CAT TGA CGT
        AAT GTT GGA CCT TCA CGA ATA TGT CCT TG

```
           ApaLI
             |
    GTGCACAAGGACATATTCGTGAAGGTCCAACATTACGTCAATGGCTTGTTGCTCTTCGTA
    1 -------+--------+--------+--------+--------+--------+ 60
    CACGTGTTCCTGTATAAGCACTTCCAGGTTGTAATGCAGTTACCGAACAACGAGAAGCAT
  c    A  Q  G  H  I  R  E  G  P  T  L  R  Q  W  L  V  A  L  R  M -

XhoI
                  |
          TGGTTCATTCTCTCGAG
       61 --------+------- 77
          ACCAAGTAAGAGAGCTC
       c    V  H  S  L  E -
```

FIGURE 7J

TMP10 [SEQ ID NOS. 69-72]

2469-14  TGC ACA AGG TCA ATT AGG ACA TGG TCC AAC TCT TCG TCA ATG
        GCT TTC TTG GTA TCG TGG TAT GCA TTC TC 2469-15  TCG AGA GAA TGC ATA CCA CGA TAC CAA GAA AGC CAT TGA CGA
        AGA GTT GGA CCA TGT CCT AAT TGA CCT TG

```
           ApaLI
             |
    GTGCACAAGGTCAATTAGGACATGGTCCAACTCTTCGTCAATGGCTTTCTTGGTATCGTG
    1 -------+--------+--------+--------+--------+--------+ 60
    CACGTGTTCCAGTTAATCCTGTACCAGGTTGAGAAGCAGTTACCGAAAGAACCATAGCAC
  c    A  Q  G  Q  L  G  H  G  P  T  L  R  Q  W  L  S  W  Y  R  G -

XhoI
                  |
          GTATGCATTCTCTCGAG
       61 --------+------ 77
          CATACGTAAGAGAGCTC
       c    M  H  S  L  E -
```

FIGURE 7K

TMP11 [SEQ ID NOS. 73-76]

2470-15  TGC ACA AGG AGA ATT ACG TCA AGG ACC AAC TCT TCA TGA ATG
GCT TCA ACA TTT AGC AAG CAA ACA TTC TC 2470-16  TCG AGA GAA TGT TTG CTT GCT AAA TGT TGA AGC CAT TCA TGA
AGA GTT GGT CCT TGA CGT AAT TCT CCT TG

```
       ApaLI
         |
GTGCACAAGGAGAATTACGTCAAGGACCAACTCTTCATGAATGGCTTCAACATTTAGCAA
1 --------+---------+---------+---------+---------+---------+ 60
CACGTGTTCCTCTTAATGCAGTTCCTGGTTGAGAAGTACTTACCGAAGTTGTAAATCGTT
c     A Q G E L R Q G P T L H E W L Q H L A S -
```

```
       XhoI
         |
       GCAAACATTCTCTCGAG
    61 --------+------- 77
       CGTTTGTAAGAGAGCTC
   c    K H S L E -
```

FIGURE 7L

TMP12 [SEQ ID NOS. 77-80]

2470-17  TGC ACA AGG AGT AGG TAT TGA AGG TCC AAC ATT ACG TCA ATG
GTT AGC TCA ACG TCT TAA TCC ACA TTC TC 2470-18  TCG AGA GAA TGT GGA TTA AGA CGT TGA GCT AAC CAT TGA CGT
AAT GTT GGA CCT TCA ATA CCT ACT CCT TG

```
       ApaLI
         |
GTGCACAAGGAGTAGGTATTGAAGGTCCAACATTACGTCAATGGTTAGCTCAACGTCTTA
1 --------+---------+---------+---------+---------+---------+ 60
CACGTGTTCCTCATCCATAACTTCCAGGTTGTAATGCAGTTACCAATCGAGTTGCAGAAT
c     A Q G V G I E G P T L R Q W L A Q R L N -
```

```
       XhoI
         |
       ATCCACATTCTCTCGAG
    61 --------+------- 77
       TAGGTGTAAGAGAGCTC
   c    P H S L E -
```

FIGURE 7M

TMP13 [SEQ ID NOS. 81-84]

2470-19  TGC ACA AGG ATG GTC ACG TGA TGG TCC AAC ACT TCG TGA ATG
        GCT TGC TTG GCG TGC TGT TGG ACA TAG TC 2470-20  TCG AGA CTA TGT CCA ACA GCA CGC CAA GCA AGC CAT TCA CGA
        AGT GTT GGA CCA TCA CGT GAC CAT CCT TG

```
         ApaLI
           |
    GTGCACAAGGATGGTCACGTGATGGTCCAACACTTCGTGAATGGCTTGCTTGGCGTGCTG
    1 --------+--------+--------+--------+--------+--------+ 60
    CACGTGTTCCTACCAGTGCACTACCAGGTTGTGAAGCACTTACCGAACGAACCGCACGAC
  c    A  Q  G  W  S  R  D  G  P  T  L  R  E  W  L  A  W  R  A  V -

XhoI
               |
         TTGGACATAGTCTCGAG
    61 --------+------- 77
         AACCTGTATCAGAGCTC
       c   G  H  S  L  E -
```

FIGURE 7N

TMP14 [SEQ ID NOS. 85-88]

2471-15  TGC ACA AGG AGC AGT TCC ACA AGG ACC AAC TCT TAA ACA GTG
        GTT ATT ATG GCG TCG TTG TGC ACA TTC TC 2471-16  TCG AGA GAA TGT GCA CAA CGA CGC CAT AAT AAC CAC TGT TTA
        AGA GTT GGT CCT TGT GGA ACT GCT CCT TG

```
         ApaLI
           |
    GTGCACAAGGAGCAGTTCCACAAGGACCAACTCTTAAACAGTGGTTATTATGGCGTCGTT
    1 --------+--------+--------+--------+--------+--------+ 60

CACGTGTTCCTCGTCAAGGTGTTCCTGGTTGAGAATTTGTCACCAATAATACCGCAGCAA
  c    A  Q  G  A  V  P  Q  G  P  T  L  K  Q  W  L  L  W  R  R  C -

XhoI
               |
         GTGCACATTCTCTCGAG
    61 --------+------- 77
         CACGTGTAAGAGAGCTC
       c   A  H  S  L  E -
```

FIGURE 7O

TMP15 [SEQ ID NOS. 89-92]

2471-17  TGC ACA AGG TCG TAT TCG TGA AGG TCC AAC TCT TAA AGA ATG
GCT TGC TCA ACG TCG TGG TTT TCA TAG TC 2471-18  TCG AGA CTA TGA AAA CCA CGA CGT TGA GCA AGC CAT TCT TTA
AGA GTT GGA CCT TCA CGA ATA CGA CCT TG

```
         ApaLI
           |
    GTGCACAAGGTCGTATTCGTGAAGGTCCAACTCTTAAAGAATGGCTTGCTCAACGTCGTG
    1 ---------+---------+---------+---------+---------+--------- + 60
    CACGTGTTCCAGCATAAGCACTTCCAGGTTGAGAATTTCTTACCGAACGAGTTGCAGCAC
  c    A Q G R I R E G P T L K E W L A Q R R G -
```

```
           XhoI
             |
        GTTTTCATAGTCTCGAG
    61 --------+------- 77
        CAAAAGTATCAGAGCTC
   c      F H S L E -
```

FIGURE 7P

TMP16 [SEQ ID NOS. 93-96]

2471-19  TGC ACA AGG TCG TTT CGC TGA AGG TCC AAC ACT TCG TGA ATG
GTT AGA ACA ACG TAA ACT TGT TCA TAG TC 2471-20  TCG AGA CTA TGA ACA AGT TTA CGT TGT TCT AAC CAT TCA CGA
AGT GTT GGA CCT TCA GCG AAA CGA CCT TG

```
         ApaLI
           |
    GTGCACAAGGTCGTTTCGCTGAAGGTCCAACACTTCGTGAATGGTTAGAACAACGTAAAC
    1 ---------+---------+---------+---------+---------+--------- + 60
    CACGTGTTCCAGCAAAGCGACTTCCAGGTTGTGAAGCACTTACCAATCTTGTTGCATTTG
  c    A Q G R F A E G P T L R E W L E Q R K L -
```

```
           XhoI
             |
        TTGTTCATAGTCTCGAG
    61 --------+------- 77
        AACAAGTATCAGAGCTC
   c      V H S L E -
```

FIGURE 7Q

TMP17 [SEQ ID NOS. 97-100]

2471-21 TGC ACA AGG TGA TCG TTT CCA AGG TCC AAC TCT TCG TGA ATG
GCT TGC TGC AAT CCG TAG CGT ACA TAG TC 2471-22 TCG AGA CTA TGT ACG CTA CGG ATT GCA GCA AGC CAT TCA CGA
AGA GTT GGA CCT TGG AAA CGA TCA CCT TG

```
           ApaLI
             |
GTGCACAAGGTGATCGTTTCCAAGGTCCAACTCTTCGTGAATGGCTTGCTGCAATCCGTA
  1 --------+---------+---------+---------+---------+--------+ 60
CACGTGTTCCACTAGCAAAGGTTCCAGGTTGAGAAGCACTTACCGAACGACGTTAGGCAT
  c     A  Q  G  D  R  F  Q  G  P  T  L  R  E  W  L  A  A  I  R  S -

XhoI
              |
          GCGTACATAGTCTCGAG
       61 --------+------- 77
          CGCATGTATCAGAGCTC
        c     V  H  S  L  E -
```

FIGURE 7R

TMP18 [SEQ ID NOS. 101-104]

2471-23 TGC ACA AGG TGC TGG TCG TGA AGG TCC AAC TCT ACG TGA ATG
GCT TAA TAT GCG TGT TTG GCA ACA TTC TC 2471-24 TCG AGA GAA TGT TGC CAA ACA CGC ATA TTA AGC CAT TCA CGT
AGA GTT GGA CCT TCA CGA CCA GCA CCT TG

```
            ApaLI
              |
GTGCACAAGGTGCTGGTCGTGAAGGTCCAACTCTACGTGAATGGCTTAATATGCGTGTTT
  1 --------+---------+---------+---------+---------+--------+ 60
CACGTGTTCCACGACCAGCACTTCCAGGTTGAGATGCACTTACCGAATTATACGCACAAA
  c     A  Q  G  A  G  R  E  G  P  T  L  R  E  W  L  N  M  R  V  W -

XhoI
              |
          GGCAACATTCTCTCGAG
       61 --------+------- 77
          CCGTTGTAAGAGAGCTC
        c     Q  H  S  L  E -
```

FIGURE 7S

TMP19 [SEQ ID NOS. 105-108]

2471-25  TGC ACA AGG AGC TTT ACA AGA AGG ACC AAC ATT ACG TCA ATG
GTT AGG ATG GGG TCA ATG GGG ACA CTC TC 2471-26  TCG AGA GAG TGT CCC CAT TGA CCC CAT CCT AAC CAT TGA CGT
AAT GTT GGT CCT TCT TGT AAA GCT CCT TG

```
            ApaLI
             |
    GTGCACAAGGAGCTTTACAAGAAGGACCAACATTACGTCAATGGTTAGGATGGGGTCAAT
    1 ----+----+----+----+----+----+ 60
    CACGTGTTCCTCGAAATGTTCTTCCTGGTTGTAATGCAGTTACCAATCCTACCCCAGTTA
  c    A Q G A L Q E G P T L R Q W L G W G Q W -

Xhol
                 |
            GGGGACACTCTCTCGAG
            61 ----+----- 77
            CCCCTGTGAGAGAGCTC
          c    G H S L E -
```

FIGURE 7T

TMP20 [SEQ ID NOS. 109-112]

2471-27  TGC ACA AGG ATA CTG TGA TGA AGG TCC AAC TCT TAA ACA ATG
GTT AGT ATG TCT TGG TTT ACA ACA TAG TC 2471-28  TCG AGA CTA TGT TGT AAA CCA AGA CAT ACT AAC CAT TGT TTA
AGA GTT GGA CCT TCA TCA CAG TAT CCT TG

```
            ApaLI
             |
    GTGCACAAGGATACTGTGATGAAGGTCCAACTCTTAAACAATGGTTAGTATGTCTTGGTT
    1 ----+----+----+----+----+----+ 60
    CACGTGTTCCTATGACACTACTTCCAGGTTGAGAATTTGTTACCAATCATACAGAACCAA
  c    A Q G Y C D E G P T L K Q W L V C L G L -

Xhol
                 |
            TACAACATAGTCTCGAG
            61 ----+----- 77
            ATGTTGTATCAGAGCTC
          c    Q H S L E -
```

FIGURE 7U

TMP22 [SEQ ID NOS. 113-116]

2471-29  TGC ACA AGG ATG TAG TTC AGG AGG TCC AAC TTT ACG TGA ATG
GTT ACA ATG TCG TCG TAT GCA ACA TTC TC 2471-30  TCG AGA GAA TGT TGC ATA CGA CGA CAT TGT AAC CAT TCA CGT
AAA GTT GGA CCT CCT GAA CTA CAT CCT TG

```
        ApaLI
         |
     GTGCACAAGGATGTAGTTCAGGAGGTCCAACTTTACGTGAATGGTTACAATGTCGTCGTA
     1 ----+----+----+----+----+----+ 60
     CACGTGTTCCTACATCAAGTCCTCCAGGTTGAAATGCACTTACCAATGTTACAGCAGCAT
   c    A Q G C S S G G P T L R E W L Q C R R M -

XhoI
           |
        TGCAACATTCTCTCGAG
       61 ----+------ 77
        ACGTTGTAAGAGAGCTC
     c    Q H S L E -
```

FIGURE 7V

TMP23 [SEQ ID NOS. 117-120]

2468-12  TGC ACA AGG ATG TTC ATG GGG TGG TCC AAC TCT TAA ACA ATG
GTT ACA ATG TGT TCG TGC TAA ACA TTC TC 2468-13  TCG AGA GAA TGT TTA GCA CGA ACA CAT TGT AAC CAT TGT TTA
AGA GTT GGA CCA CCC CAT GAA CAT CCT TG

```
        ApaLI
         |
     GTGCACAAGGATGTTCATGGGGTGGTCCAACTCTTAAACAATGGTTACAATGTGTTCGTG
     1 ----+----+----+----+----+----+ 60
     CACGTGTTCCTACAAGTACCCCACCAGGTTGAGAATTTGTTACCAATGTTACACAAGCAC
   c    A Q G C S W G G P T L K Q W L Q C V R A -

XhoI
           |
        CTAAACATTCTCTCGAG
       61 ----+------ 77
        GATTTGTAAGAGAGCTC
     c    K H S L E -
```

FIGURE 7W

TMP24 [SEQ ID NOS. 121-124]

2543-44    TGC ACA AGG ATG TCA ATT AGG TGG TCC GAC TCT TCG TGA ATG
GCT TGC TTG TCG TCT TGG TGC TCA TTC AC 2543-45    TCG AGT GAA TGA GCA CCA AGA CGA CAA GCA AGC CAT TCA CGA
AGA GTC GGA CCA CCT AAT TGA CAT CCT TG

```
            ApaLI
              |
   GTGCACAAGGATGTCAATTAGGTGGTCCGACTCTTCGTGAATGGCTTGCTTGTCGTCTTG
   1 ---------+---------+---------+---------+---------+--------- 60
   CACGTGTTCCTACAGTTAATCCACCAGGCTGAGAAGCACTTACCGAACGAACAGCAGAAC
 c     A  Q  G  C  Q  L  G  G  P  T  L  R  E  W  L  A  C  R  L  G -

XhoI
                |
         GTGCTCATTCACTCGAG
      61 --------+------ 77
         CACGAGTAAGTGAGCTC
 c        A  H  S  L  E -
```

FIGURE 7X

TMP25 [SEQ ID NOS. 125-128]

2543-46    TGC ACA AGG ATG TTG GGA AGG TGG TCC TAC ACT TAA AGA ATG
GCT TCA ATG TCT TGT AGA ACG TCA TTC AC 2543-47    TCG AGT GAA TGA CGT TCT ACA AGA CAT TGA AGC CAT TCT TTA
AGT GTA GGA CCA CCT TCC CAA CAT CCT TG

```
            ApaLI
              |
   GTGCACAAGGATGTTGGGAAGGTGGTCCTACACTTAAAGAATGGCTTCAATGTCTTGTAG
   1 ---------+---------+---------+---------+---------+--------- 60
   CACGTGTTCCTACAACCCTTCCACCAGGATGTGAATTTCTTACCGAAGTTACAGAACATC
 c     A  Q  G  C  W  E  G  G  P  T  L  K  E  W  L  Q  C  L  V  E-

XhoI
                |
         AACGTCATTCACTCGAG
      61 --------+------ 77
 c        R  H  S  L  E -
```

FIGURE 7Y

TMP26 [SEQ ID NOS. 129-132]

2551-29  TGC ACA AGG TTG TCG TGG TGG TGG TCC AAC TCT TCA TCA ATG
        GCT TTC TTG TTT TCG TTG GCA ACA TTC AC 2551-30  TCG AGT GAA TGT TGC CAA CGA AAA CAA GAA AGC CAT TGA TGA
        AGA GTT GGA CCA CCA CCA CGA CAA CCT TG

```
        ApaLI
          |
GTGCACAAGGTTGTCGTGGTGGTGGTCCAACTCTTCATCAATGGCTTTCTTGTTTTCGTT
 I --------+---------+---------+---------+---------+--------+ 60
CACGTGTTCCAACAGCACCACCACCAGGTTGAGAAGTAGTTACCGAAAGAACAAAAGCA
 c      A Q G C R G G G P T L H Q W L S C F R W -

XhoI
          |
        AGGCAACATTCACTCGAG
     61 --------+------- 77
        CCGTTGTAAGTGAGCTC
 c      Q H S L E -
```

FIGURE 7Z

TMP27 [SEQ ID NOS. 133-136]

2551-94  TGC ACA AGG ATG TCG TGA TGG TGG TCC AAC TCT TAG ACA ATG
        GCT TGC TTG TCT TCA ACA AAA ACA TTC AC 2551-95  TCG AGT GAA TGT TTT TGT TGA AGA CAA GCA AGC CAT TGT CTA
        AGA GTT GGA CCA CCA TCA CGA CAT CCT TG

```
        ApaLI
          |
GTGCACAAGGATGTCGTGATGGTGGTCCAACTCTTAGACAATGGCTTGCTTGTCTTCAAC
 I --------+---------+---------+---------+---------+--------+ 60
CACGTGTTCCTACAGCACTACCACCAGGTTGAGAATCTGTTACCGAACGAACAGAAGTTG
 c      A Q G C R D G G P T L R Q W L A C L Q Q -

XhoI
          |
        AAAAACATTCACTCGAG
     61 --------+------- 77
        TTTTTGTAAGTGAGCTC
 c      K H S L E -
```

FIGURE 7AA

TMP28 [SEQ ID NOS. 137-140]

2551-96  TCG AGT GAA TGT TGA GCA AGA CGC CAA ACA AGC CAT TCT TTT
         AAA GTT GGA CCA GAT CTT AAT TCT CCT TG 2551-97  TGC ACA AGG AGA ATT AAG ATC TGG TCC AAC TTT AAA AGA ATG
         GCT TGT TTG GCG TCT TGC TCA ACA TTC AC

```
    ApaLI
     |
GTGCACAAGGAGAATTAAGATCTGGTCCAACTTTAAAAGAATGGCTTGTTTGGCGTCTTG
1 -----+--------+--------+--------+--------+--------+ 60
CACGTGTTCCTCTTAATTCTAGACCAGGTTGAAATTTTCTTACCGAACAAACCGCAGAAC
c    A Q G E L R S G P T L K E W L V W R L A -
```

```
       XhoI
        |
    CTCAACATTCACTCGAG
61 ------+------ 77
    GAGTTGTAAGTGAGCTC
c    Q H S L E -
```

FIGURE 7BB

TMP29 [SEQ ID NOS. 141-144]

2552-63  TGC ACA AGG AGG ATG TAG ATC TGG TCC AAC ACT TCG TGA ATG
         GTT AGC TTG TAG AGA GGT TCA ACA CTC TC 2552-64  TCG AGA GAG TGT TGA ACC TCT CTA CAA GCT AAC CAT TCA CGA
         AGT GTT GGA CCA GAT CTA CAT CCT CCT TG

```
     ApaLI
      |
GTGCACAAGGAGGATGTAGATCTGGTCCAACACTTCGTGAATGGTTAGCTTGTAGAGAGG
1 --------+--------+--------+--------+--------+--------+ 60
CACGTGTTCCTCCTACATCTAGACCAGGTTGTGAAGCACTTACCAATCGAACATCTCTCC
c    A Q G G C R S G P T L R E W L A C R E V -
```

```
        XhoI
         |
    TTCAACACTCTCTCGAG
61 ---------+------ 77
    AAGTTGTGAGAGAGCTC
c    Q H S L E -
```

FIGURE 7CC

TMP30 [SEQ ID NOS. 145-148]

2552-65 TGC ACA AGG TAC ATG CGA ACA AGG ACC AAC TCT AAG ACA ATG
GCT ACT ATG TAG ACA AGG AAG ACA CTC AC 2552-66 TCG AGT GAG TGT CTT CCT TGT CTA CAT AGT AGC CAT TGT CTT
AGA GTT GGT CCT TGT TCG CAT GTA CCT TG

```
        ApaLI
         |
GTGCACAAGGTACATGCGAACAAGGACCAACTCTAAGACAATGGCTACTATGTAGACAAG
1 --------+---------+---------+---------+---------+---------+ 60
CACGTGTTCCATGTACGCTTGTTCCTGGTTGAGATTCTGTTACCGATGATACATCTGTTC
c     A Q G T C E Q G P T L R Q W L L C R Q G -
```

```
        XhoI
         |
     GAAGACACTCACTCGAG
 61 --------+------- 77
     CTTCTGTGAGTGAGCTC
 c     R H S L E -
```

TMP21 was cloned directly from the phage display (Target Quest) library as an *ApaLI* to *XhoI* fragment. The sequence of the insert is given below.

FIGURE 7DD

TMP21 [SEQ ID NOS. 149-150]

```
        ApaLI
         |
GTGCACAGGGTTGGTGTAAGGAGGGTCCTACTCTGCGTGAGTGGCTGCGGTGGGGTTTTC
1 --------+---------+---------+---------+---------+---------+ 60
CACGTGTCCCAACCACATTCCTCCCAGGATGAGACGCACTCACCGACGCCACCCCAAAAG
c     A Q G W C K E G P T L R E W L R W G F L -
```

```
        XhoI
         |
     TGTGTCATTCTCTCGAG
 61 ---------+-------
 c   C H S L E
```

FIGURE 8A

200003182 vector

```
                                   NdeI
                                    |
    TCGATTAATCGATTTGATTCTAGATTTGTTTTAACTAATTAAAGGAGGAATAACATATGG
1   ---------+---------+---------+---------+---------+---------+ 60
    AGCTAATTAGCTAAACTAAGATCTAAACAAAATTGATTAATTTCCTCCTTATTGTATACC
                                                              M D
```

```
    ACAAAACTCACACATGTCCACCTTGTCCAGCTCCGGAACTCCTGGGGGGACCGTCAGTCT
61  ---------+---------+---------+---------+---------+---------+ 120
    TGTTTTGAGTGTGTACAGGTGGAACAGGTCGAGGCCTTGAGGACCCCCCTGGCAGTCAGA
``` c   K T H T C P P C P A P E L L G G P S V F -

```
    TCCTCTTCCCCCCAAAACCCAAGGACACCCTCATGATCTCCCGGACCCCTGAGGTCACAT
121 ---------+---------+---------+---------+---------+---------+ 180
    AGGAGAAGGGGGGTTTTGGGTTCCTGTGGGAGTACTAGAGGGCCTGGGGACTCCAGTGTA
``` c   L F P P K P K D T L M I S R T P E V T C -

```
    GCGTGGTGGTGGACGTGAGCCACGAAGACCCTGAGGTCAAGTTCAACTGGTACGTGGACG
181 ---------+---------+---------+---------+---------+---------+ 240
    CGCACCACCACCTGCACTCGGTGCTTCTGGGACTCCAGTTCAAGTTGACCATGCACCTGC
``` c   V V V D V S H E D P E V K F N W Y V D G -

```
    GCGTGGAGGTGCATAATGCCAAGACAAAGCCGCGGGAGGAGCAGTACAACAGCACGTACC
241 ---------+---------+---------+---------+---------+---------+ 300
    CGCACCTCCACGTATTACGGTTCTGTTTCGGCGCCCTCCTCGTCATGTTGTCGTGCATGG
``` c   V E V H N A K T K P R E E Q Y N S T Y R -

```
    GTGTGGTCAGCGTCCTCACCGTCCTGCACCAGGACTGGCTGAATGGCAAGGAGTACAAGT
301 ---------+---------+---------+---------+---------+---------+ 360
    CACACCAGTCGCAGGAGTGGCAGGACGTGGTCCTGACCGACTTACCGTTCCTCATGTTCA
``` c   V V S V L T V L H Q D W L N G K E Y K C -

```
    GCAAGGTCTCCAACAAAGCCCTCCCAGCCCCCATCGAGAAAACCATCTCCAAAGCCAAAG
361 ---------+---------+---------+---------+---------+---------+ 420
    CGTTCCAGAGGTTGTTTCGGGAGGGTCGGGGGTAGCTCTTTTGGTAGAGGTTTCGGTTTC
``` c   K V S N K A L P A P I E K T I S K A K G -

```
          BsrGI
            |
    GGCAGCCCCGAGAACCACAGGTGTACACCCTGCCCCCATCCCGGGATGAGCTGACCAAGA
421 ---------+---------+---------+---------+---------+---------+ 480
    CCGTCGGGGCTCTTGGTGTCCACATGTGGGACGGGGGTAGGGCCCTACTCGACTGGTTCT
``` c   Q P R E P Q V Y T L P P S R D E L T K N -

```
    ACCAGGTCAGCCTGACCTGCCTGGTCAAAGGCTTCTATCCCAGCGACATCGCCGTGGAGT
481 ---------+---------+---------+---------+---------+---------+ 540
    TGGTCCAGTCGGACTGGACGGACCAGTTTCCGAAGATAGGGTCGCTGTAGCGGCACCTCA
```

FIGURE 8B c     Q V S L T C L V K G F Y P S D I A V E W -

```
    GGGAGAGCAATGGGCAGCCGGAGAACAACTACAAGACCACGCCTCCCGTGCTGGACTCCG
541 ---------+---------+---------+---------+---------+---------+ 600
    CCCTCTCGTTACCCGTCGGCCTCTTGTTGATGTTCTGGTGCGGAGGGCACGACCTGAGGC
``` c     E S N G Q P E N N Y K T T P P V L D S D -

```
    ACGGCTCCTTCTTCCTCTACAGCAAGCTCACCGTGGACAAGAGCAGGTGGCAGCAGGGGA
601 ---------+---------+---------+---------+---------+---------+ 660
    TGCCGAGGAAGAAGGAGATGTCGTTCGAGTGGCACCTGTTCTCGTCCACCGTCGTCCCCT
``` c     G S F F L Y S K L T V D K S R W Q Q G N -

```
    ACGTCTTCTCATGCTCCGTGATGCATGAGGCTCTGCACAACCACTACACGCAGAAGAGCC
661 ---------+---------+---------+----------+---------+---------+ 720
    TGCAGAAGAGTACGAGGCACTACGTACTCCGAGACGTGTTGGTGATGTGCGTCTTCTCGG
``` c     V F S C S V M H E A L H N H Y T Q K S L -

```
                   ApaLI          XhoI
                     |              |
    TCTCCCTGTCTCCGGGTAAAGGTGGAGGTGGTGGTGCACAGAAAGCGGCCGCAAAAAAAC
721 ---------+---------+---------+---------+---------+---------+ 780
    AGAGGGACAGAGGCCCATTTCCACCTCCACCACCACGTGTCTTTCGCCGGCGTTTTTTTG
``` c     S L S P G K G G G G G A Q K A A A K K L -

```
    BamHI
      |
    TCGAGTAATGGATCCGCGGAAAGAAGAAGAAGAAGAAGAAAGCCCGAAAGGAAGCTG
781 ---------+---------+----------+----------+---------+------- 837
    AGCTCATTACCTAGGCGCCTTTCTTCTTCTTCTTCTTCTTTCGGGCTTTCCTTCGAC
``` c     E *

[SEQ ID NO. 151] (Nucleic Acid)

[SEQ ID NO. 152] (Amino Acid)

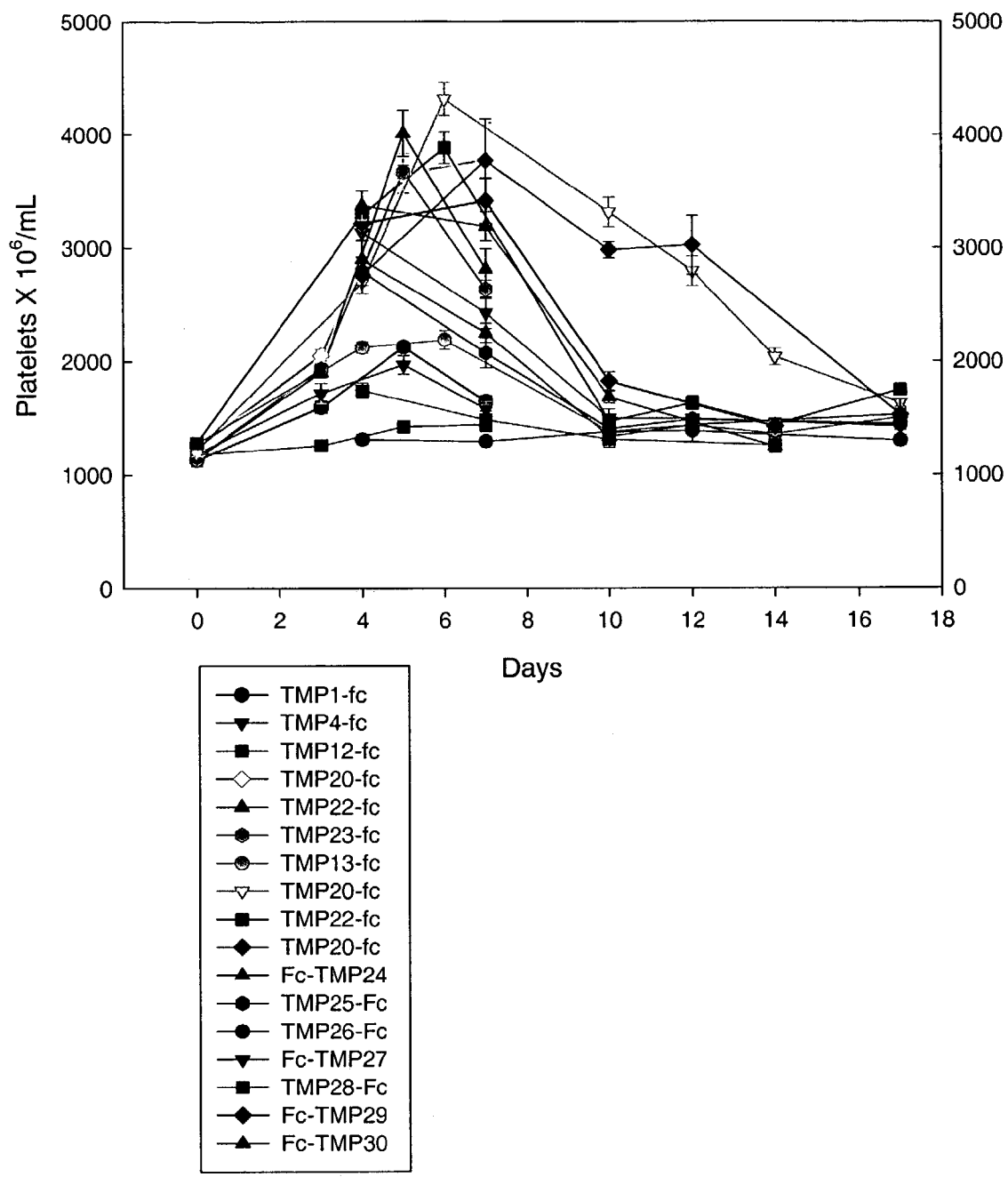

PEPTIDES AND RELATED COMPOUNDS HAVING THROMBOPOIETIC ACTIVITY

This application claims the benefit of U.S. Provisional Application No. 60/328,666 filed Oct. 11, 2001, which is hereby incorporated by reference.

FIELD OF THE INVENTION

The present invention relates generally to peptides and related compounds that have thrombopoietic activity. The compounds of the invention may be used to increase production of platelets or platelet precursors (e.g. megakaryocytes) in a mammal.

BACKGROUND OF THE INVENTION

This invention relates to compounds, especially peptides, that have the ability to stimulate in vitro and in vivo-production of platelets and their precursor cells, e.g., megakaryocytes. The following is provided as background regarding two proteins that are known to have thrombopoietic activity: thrombopoietin (TPO) and megakaryocyte growth and development factor (MGDF).

The cloning of endogenous thrombopoietin (TPO) (Lok et al., Nature 369:568-571 (1994); Bartley et al., Cell 77:1117-1124 (1994); Kuter et al., Proc. Natl. Acad. Sci. USA 91:11104-11108 (1994); de Sauvage et al., Nature 369:533-538 (1994); Kato et al., Journal of Biochemistry 119:229-236 (1995); Chang et al., Journal of Biological Chemistry 270:511-514 (1995)) has rapidly increased our understanding of megakaryopoiesis (megakaryocyte production) and thrombopoiesis (platelet production).

Endogenous human TPO, a 60 to 70 kDa glycosylated protein primarily produced in the liver and kidney, consists of 332 amino acids (Bartley et al., Cell 77:1117-1124 (1994); Chang et al., Journal of Biological Chemistry 270:511-514 (1995)). The protein is highly conserved between different species, and has 23% homology with human erythropoietin (Gurney et al., Blood 85:981-988 (1995)) in the amino terminus (amino acids 1 to 172) (Bartley et al., Cell 77:1117-1124 (1994)). Endogenous TPO has been shown to possess all of the characteristics of the key biological regulator of thrombopoiesis. Its in vitro actions include specific induction of megakaryocyte colonies from both purified murine hematopoietic stem cells (Zeigler et al., Blood 84:4045-4052 (1994)) and human $CD34^+$ cells (Lok et al., Nature 369:568-571 (1994); Rasko et al., Stem Cells 15:33-42 (1997)), the generation of megakaryocytes with increased ploidy (Broudy et al., Blood 85:402-413 (1995)), and the induction of terminal megakaryocyte maturation and platelet production (Zeigler et al., Blood 84:4045-4052 (1994); Choi et al., Blood 85:402-413 (1995)). Conversely, synthetic antisense oligodeoxynucleotides to the TPO receptor (c-mpl) significantly inhibit the colony-forming ability of megakaryocyte progenitors (Methia et al., Blood 82:1395-1401 (1993)). Moreover, c-mpl knock-out mice are severely thrombocytopenic and deficient in megakaryocytes (Alexander et al., Blood 87:2162-2170 (1996)).

Recombinant human MGDF (rHuMGDF, Amgen Inc., Thousand Oaks, Calif.) is another thrombopoietic polypeptide related to TPO. It is produced using *E. coli* transformed with a plasmid containing cDNA encoding a truncated protein encompassing the amino-terminal receptor-binding domain of human TPO (Ulich et al., Blood 86:971-976 (1995)). The polypeptide is extracted, refolded, and purified, and a poly[ethylene glycol] (PEG) moiety is covalently attached to the amino terminus. The resulting molecule is referred to herein as PEG-rHuMGDF or MGDF for short.

Various studies using animal models (Ulich, T. R. et al., Blood 86:971-976 (1995); Hokom, M. M. et al., Blood 86:4486-4492 (1995)) have clearly demonstrated the therapeutic efficacies of TPO and MGDF in bone marrow transplantation and in the treatment of thrombocytopenia, a condition that often results from chemotherapy or radiation therapy. Preliminary data in humans have confirmed the utility of MGDF in elevating platelet counts in various settings. (Basser et al., Lancet 348:1279-81 (1996); Kato et al., Journal of Biochemistry 119:229-236 (1995); Ulich et al., Blood 86:971-976 (1995)). MGDF might be used to enhance the platelet donation process, since administration of MGDF increases circulating platelet counts to about three-fold the original value in healthy platelet donors.

TPO and MGDF exert their action through binding to the c-mpl receptor which is expressed primarily on the surface of certain hematopoietic cells, such as megakaryocytes, platelets, $CD34^+$ cells and primitive progenitor cells (Debili, N. et al., Blood 85:391-401 (1995); de Sauvage, F. J. et al, Nature 369:533-538 (1994); Bartley, T. D., et al., Cell 77:1117-1124 (1994); Lok, S. et al., Nature 369: 565-8 (1994)). Like most receptors for interleukins and protein hormones, c-mpl belongs to the class I cytokine receptor superfamily (Vigon, I. et al., Proc. Natl. Acad. Sci. USA 89:5640-5644 (1992)). Activation of this class of receptors involves ligand-binding induced receptor homodimerization which in turn triggers the cascade of signal transducing events.

In general, the interaction of a protein ligand with its receptor often takes place at a relatively large interface. However, as demonstrated in the case of human growth hormone bound to its receptor, only a few key residues at the interface actually contribute to most of the binding energy (Clackson, T. et al., Science 267:383-386 (1995)). This and the fact that the bulk of the remaining protein ligand serves only to display the binding epitopes in the right topology makes it possible to find active ligands of much smaller size. Accordingly, molecules of only "peptide" length (e.g., 2 to 80 amino acids) can bind to the receptor protein of a given large protein ligand. Such peptides may mimic the bioactivity of the large protein ligand or, through competitive binding, inhibit the bioactivity of the large protein ligand, and are commonly referred to as "peptide mimetics" or "mimetic peptides."

Phage display peptide libraries have emerged as a powerful technique in identifying such peptide mimetics. See, e.g., Scott, J. K. et al., Science 249:386 (1990); Devlin, J. J. et al., Science 249:404 (1990); U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference in its entirety). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla, et al. (1997), Science 276: 1696-9. The peptide sequences may also suggest which residues may be safely replaced by alanine scanning or by mutagenesis at the DNA level. Mutagenesis libraries may be created and screened to further optimize the sequence of the best binders. Lowman (1997), Ann. Rev. Biophys. Biomol. Struct. 26: 401-24.

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki, et al. (1997), Nature Biotech, 15: 1266-70. These analytical methods may also be used to investigate the interaction between a receptor protein and peptides selected by phage display, which may suggest further modification of the peptides to increase binding affinity.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." In another method, translation of random RNA is halted prior to ribosome release, resulting in a library of polypeptides with their associated RNA still attached. Hereinafter, this and related methods are collectively referred to as "ribosome display." Other methods employ peptides linked to RNA; for example, PROfusion technology, Phylos, Inc. See, for example, Roberts & Szostak (1997), Proc. Natl. Acad. Sci. USA, 94: 12297-303. Hereinafter, this and related methods are collectively referred to as "RNA-peptide screening." Chemically derived peptide libraries have been developed in which peptides are immobilized on stable, non-biological materials, such as polyethylene rods or solvent-premeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman (1992), Curr. Opin. Biotechnol, 3: 355-62. Conceptually, one may discover peptide mimetics of any protein using phage display, RNA-peptide screening, and the other methods mentioned above.

By using the phage display peptide library technique, small peptide molecules that act as agonists of the c-mpl receptor were discovered (Cwirla, S. E. et al., Science 276:1696-1699 (1997)). In such a study, random small peptide sequences displayed as fusions to the coat proteins of filamentous phage were affinity-eluted against the antibody-immobilized extracellular domain of c-mpl and the retained phages were enriched for a second round of affinity purification. This binding selection and repropagation process was repeated many times to enrich the pool of tighter binders. As a result, two families of c-mpl-binding peptides, unrelated to each other in their sequences, were first identified. Mutagenesis libraries were then created to further optimize the best binders, which finally led to the isolation of a very active peptide with an $IC_{50}=2$ nM and an $EC_{50}=400$ nM (Cwirla, S. E. et al., Science 276:1696-1699 (1997)). This 14-residue TPO mimetic peptide has no apparent sequence homology to TPO or MGDF. The structure of this particular TPO mimetic peptide (TMP)compound is as follows:

```
Ile Glu Gly Pro Thr Leu Arg Gln Trp Leu Ala Ala Arg Ala   (SEQ ID NO:1)
or,

IEGPTLRQWLAARA
``` using single letter amino acid abbreviations.

Previously, in a similar study on EPO mimetic peptides, an EPO mimetic peptide (EMP) was discovered using the same technique (Wrighton, N. C. et al., Science, 273:458-463 (1996)), and was found to act as a dimer in binding to the EPO receptor (EPOR). The $(ligand)_2/(receptor)_2$ complex thus formed had a C2 symmetry according to X-ray crystallographic data (Livnah, O. et al., Science 273:464-471 (1996)). Based on this structural information, a covalently linked dimer of EMP in which the C-termini of two EMP monomers were crosslinked with a flexible spacer was designed and found to have greatly enhanced binding as well as in vitro/in vivo bioactivity (Wrighton, N. C., et al., Nature Biotechnology 15:1261-1265 (1997)).

A similar C-terminal dimerization strategy was applied to the TPO mimetic peptide (TMP). (Cwirla, S. E. et al., Science 276:1696-1699 (1997)). It was found that a C-terminally linked dimer (C-C link) of a particular TPO mimetic peptide had an improved binding affinity of 0.5 nM and an increased in vitro activity ($EC_{50}=0.1$ nM) in cell proliferation assays (Cwirla, S. E. et al., Science 276:1696-1699 (1997)).

The availability of recombinant proteins for therapeutic use has led to advances in protein modifications in order to enhance or improve the properties of such proteins as pharmaceutical agents. Such modifications can provide enhanced protein protection and decreased degradation by reducing or eliminating proteolysis. Additional advantages include, under certain circumstances, increasing the stability, circulation time and biological activity of the therapeutic protein. A review article describing protein modifications is Francis, Focus on Growth Factors 3:4-10 (May 1992) (published by Mediscript, London, UK).

Useful modifications of protein therapeutic agents include linkage to polymers such as polyethylene glycol (PEG) and dextran. Such modifications are discussed in detail in a patent application entitled "Modified Peptides as Therapeutic Agents," U.S. Ser. No. 09/428,082, PCT appl. no. WO 00/24782, which is hereby incorporated by reference in its entirety.

Another such modification is the use of an Fc region of an immunoglobulin molecule. Antibodies comprise two functionally independent parts; a variable domain known as "Fab" which binds an antigen, and a constant domain known as "Fc" which provides the link to effector functions such as complement or phagocytic cells. The Fc portion of an immunoglobulin has a long plasma half-life, whereas the Fab is short-lived. (Capon, et al. Nature 337, 525-531 (1989)).

Therapeutic protein products have been constructed using the Fc domain to provide longer half life or to incorporate functions such as Fc receptor binding, protein A binding, complement fixation and placental transfer which all reside in the Fc proteins of immunoglobulins. (Capon, et al., Nature 337:525-531 (1989)). For example, the Fc region of an IgG1 antibody has been fused to CD30-L, a molecule which binds CD30 receptors expressed on Hodgkin's Disease tumor cells, anaplastic lymphoma cells, T-cell leukemia cells and other malignant cell types. See, U.S. Pat. No. 5,480,981. IL-10, an anti-inflammatory and antirejection agent has been fused to murine Fc 2a in order to increase the cytokine's short circulating half-life (Zheng, X. et al., The Journal of Immunology, 154: 5590-5600 (1995)). Studies have also evaluated the use of tumor necrosis factor receptor linked with the Fc protein of human IgG1 to treat patients with septic shock (Fisher, C. et al., N. Engl. J. Med., 334: 1697-1702 (1996); Van Zee, K. et al., The Journal of Immunology, 156: 2221-2230 (1996)). Fc has also been fused with CD4 receptor to produce a therapeutic protein for treatment of AIDS. See, Capon et al., Nature, 337:525-531 (1989). In addition, interleukin 2 has been fused to the Fc portion of IgG1 or IgG3 to overcome the short half life of interleukin 2 and its systemic toxicity. See, Harvill et al., Immunotechnology, 1: 95-105 (1995).

Published PCT Application No. WO 00/24770 discloses specific thrombopoietic compounds, generally peptides, having a tandem (i.e., N- to C-terminus) orientation and tandem peptide dimers attached at the N-terminus thereof to a carrier molecule, such as a linear polymer, an oligosaccharide or an Fc group.

There remains a need to provide additional compounds having a superior biological activity of stimulating the production of platelets (thrombopoietic activity) and/or platelet precursor cells, especially megakaryocytes (megakaryopoietic activity). There also remains a need to provide compounds that exhibit thrombopoietic activity and that also possess superior therapeutic qualities, such as a long half-life. Such compounds will exhibit advantageous properties relating to production, isolation, purification, biological activity, stability and circulation time. The present invention provides new compounds having such activity(ies), and related aspects.

SUMMARY OF THE INVENTION

The present invention concerns therapeutic compounds that bind to the c-mpl receptor (hereinafter "the mpl receptor"). More particularly, the present invention provides a group of compounds that demonstrate an improved ability to bind to and/or trigger a transmembrane signal through, i.e., activating, the mpl receptor, which is the same receptor that mediates the activity of endogenous thrombopoietin (TPO). Thus, the inventive compounds have superior thrombopoietic activity, i.e., the ability to stimulate, in vivo and in vitro, the production of platelets and/or megakaryocytopoietic activity, i.e., the ability to stimulate, in vivo and in vitro, the production of platelet precursors. Further, certain of the inventive compounds also exhibit superior therapeutic properties, such as improved plasma half-life, biological activity and in vivo circulation time.

In one aspect, the present invention provides a compound that binds to an mpl receptor comprising the sequence:

X1-X2-X3-X4-G-P-T-L-X9-X10-W-L-X13-X14-X15-X16-X17-X18 wherein X1-X4, X9-X10, and X13-X18 are each independently an amino acid as defined herein, and wherein the compound has a binding affinity for the mpl receptor and/or a bioactivity greater than that of the sequence:

I-E-G-P-T-L-R-Q-W-L-A-A-R-A.

In yet a further aspect, the present invention provides a compound that binds to an mpl receptor having the sequence:

X1-X2-R-E-G-P-T-L-R-Q-W-L-X13-W-R-R-X17-X18 wherein X1, X2, X13, X17 and X18 are each independently an amino acid.

In yet another aspect, the present invention provides a compound that binds to an mpl receptor comprising a sequence which is selected from the group consisting of SEQ ID NO 2 to SEQ ID NO 30, inclusive.

In another aspect, the present invention is a dimer or multimer of a compound comprising a sequence which is selected from the group consisting of SEQ ID NO 2 to SEQ ID NO 30.

In another aspect, the present invention provides a composition of matter that binds to an mpl receptor having the formula:

$$(LN1)_1-(TMP1)_a-(LN2)_m-(TMP2)_b-(LN3)_n-(TMP3)_c-(LN4)_o-(TMP4)_d$$

wherein TMP1, TMP2, TMP3 and TMP4 are each independently selected from the group consisting of the TMPs disclosed herein; LN1, LN2, LN3 and LN4 are each independently a linker; a, b, c and d are each independently an integer from zero to ten; and l, m, n and o are each independently an integer from zero to twenty.

In yet another aspect, the present invention provides a composition of matter that binds to an mpl receptor having the formula:

$$(V1)_v-(LN1)_1-(TMP1)_a-(LN2)_m-(TMP2)_b-(LN3)_n-(TMP3)_c-(LN4)_o-(TMP4)_d-(V2)_w$$

wherein V1 and V2 are each independently a vehicle, and v and w are each independently an integer from 0 to 1.

The compounds of this invention may be prepared by standard synthetic methods, recombinant DNA techniques, or any other methods of preparing peptides and fusion proteins. Compounds of this invention that encompass non-peptide portions may be synthesized by standard organic chemistry reactions, in addition to standard peptide chemistry reactions when applicable.

The compounds of this invention may be used for therapeutic or prophylactic purposes by formulating them with appropriate pharmaceutical carrier materials and administering an effective amount to a patient, such as a human (or other mammal) in need thereof. The vehicle-linked peptide may have activity comparable to—or even greater than—the natural ligand mimicked by the peptide, here, thrombopoietin.

In another aspect, the present invention provides methods of treating thrombocytopenic disorders. In other aspects, the present invention provides methods of increasing megakaryocytes or platelets and methods of producing compounds described herein.

In yet another aspect, the present invention also provides for related pharmaceutical compositions.

In other aspects, the present invention provides for polynucleotides encoding the compositions of matter disclosed herein, expression vectors comprising the polynucleotides and host cells comprising the expression vectors.

BRIEF DESCRIPTION OF THE FIGURES

Numerous other aspects and advantages of the present invention will therefore be apparent upon consideration of the following detailed description thereof, reference being made to the drawings wherein:

FIG. 1 shows exemplary structures of peptide and peptide-linker compounds of the present invention.

FIG. 2 shows exemplary structures of peptide-vehicle and peptide-linker-vehicle compounds of the present invention.

FIG. 3 shows the nucleic acid and amino acid sequences (SEQ ID NOS: 31 and 32, respectively) of human IgG1 Fc that may be used as a preferred vehicle in this invention.

FIG. 4 shows exemplary Fc monomer and dimers compounds of the present invention that may be derived from an IgG1 antibody. "Fc" in the figure represents any of the Fc variants within the meaning of Fc domain herein. "Peptide" represent any of the peptides, linker-peptides, peptide-peptide combinations, or any combination thereof, as disclosed herein. The specific dimers are as follows:

FIGS. 4A and 4D show single disulfide-bonded dimers. IgG1 antibodies typically have two disulfide bonds at the hinge region of the antibody. The Fc domain in FIGS. 4A and 4D may be formed by truncation between the two disulfide bond sites or by substitution of a cysteinyl residue with an unreactive residue (e.g., alanyl). In FIG. 4A, the Fc domain is linked to the amino terminus of the peptide; in 4D, at the carboxyl terminus of the peptide.

FIGS. 4B and 4E show doubly disulfide-bonded dimers. This Fc domain may be formed by truncation of the parent antibody to retain both cysteinyl residues in the Fc domain chains or by expression from a construct including a sequence encoding such an Fc domain. In FIG. 4B, the Fc domain is linked to the amino terminus of the peptide; in 4E, at the carboxyl terminus of the peptide.

FIGS. 4C and 4F show noncovalent dimers. This Fc domain may be formed by elimination of the cysteinyl residues by either truncation or substitution. One may desire to eliminate the cysteinyl residues to avoid impurities formed by reaction of the cysteinyl residue with cysteinyl residues of other proteins present in the host cell. The noncovalent bonding of the Fc domains is sufficient to hold together the dimer. Other dimers may be formed by using Fc domains derived from different types of antibodies (e.g., IgG2, IgM).

FIGS. 4G and 4H show single chain Fc domains attached at the N-terminus of a peptide (FIG. 4G) and at the C-terminus of a peptide (FIG. 4H).

FIG. 5 shows exemplary structures of preferred compounds of the invention that feature tandem repeats of the pharmacologically active peptide attached to an Fc domain. FIG. 5A shows a single chain (or Fc monomer) molecule having attached thereto a tandem peptide dimer, and may also represent the DNA construct for the molecule. FIG. 5B shows an Fc dimer in which the linker-peptide portion is present on only one chain of the Fc dimer. FIG. 5C shows an Fc dimer having the peptide portion (in this case, a tandem peptide dimer) on both chains. The dimer of FIG. 5C will form spontaneously in certain host cells upon expression of a DNA construct encoding the single chain shown in FIG. 5A. In other host cells, the cells could be placed in conditions favoring formation of dimers or the dimers can be formed in vitro. FIGS. 5D through 5I represent additional exemplary single chain (Fc monomer) and double chain (Fc dimer) preferred embodiments.

FIG. 6 shows the nucleic acid sequence (SEQ ID NO 33) and amino acid sequence (SEQ ID NO 34) for a preferred vector (20003180) for use in constructing TMP-Fc fusions compounds as shown in Example 3 herein.

FIG. 7 shows fragments of exemplary pairs of oligonucleotides used to create preferred peptides of the present invention as shown in Example 3. Nucleic acid and amino acid sequences are provided for each. (SEQ ID NOS 35-150)

FIG. 8 shows the nucleic acid sequence (SEQ ID NO 151) and the amino acid sequence (SEQ ID NO 152) of an exemplary vector (20003182) for use in constructing C-terminal Fc fusion compounds (i.e., peptide attached at its N-terminus to the C-terminus of the Fc).

FIGS. 13 and 14 show in vivo platelet counts after a single injection of select compounds of the present invention into mice.

DETAILED DESCRIPTION OF THE INVENTION

I. Definition of Terms

Figure 9:
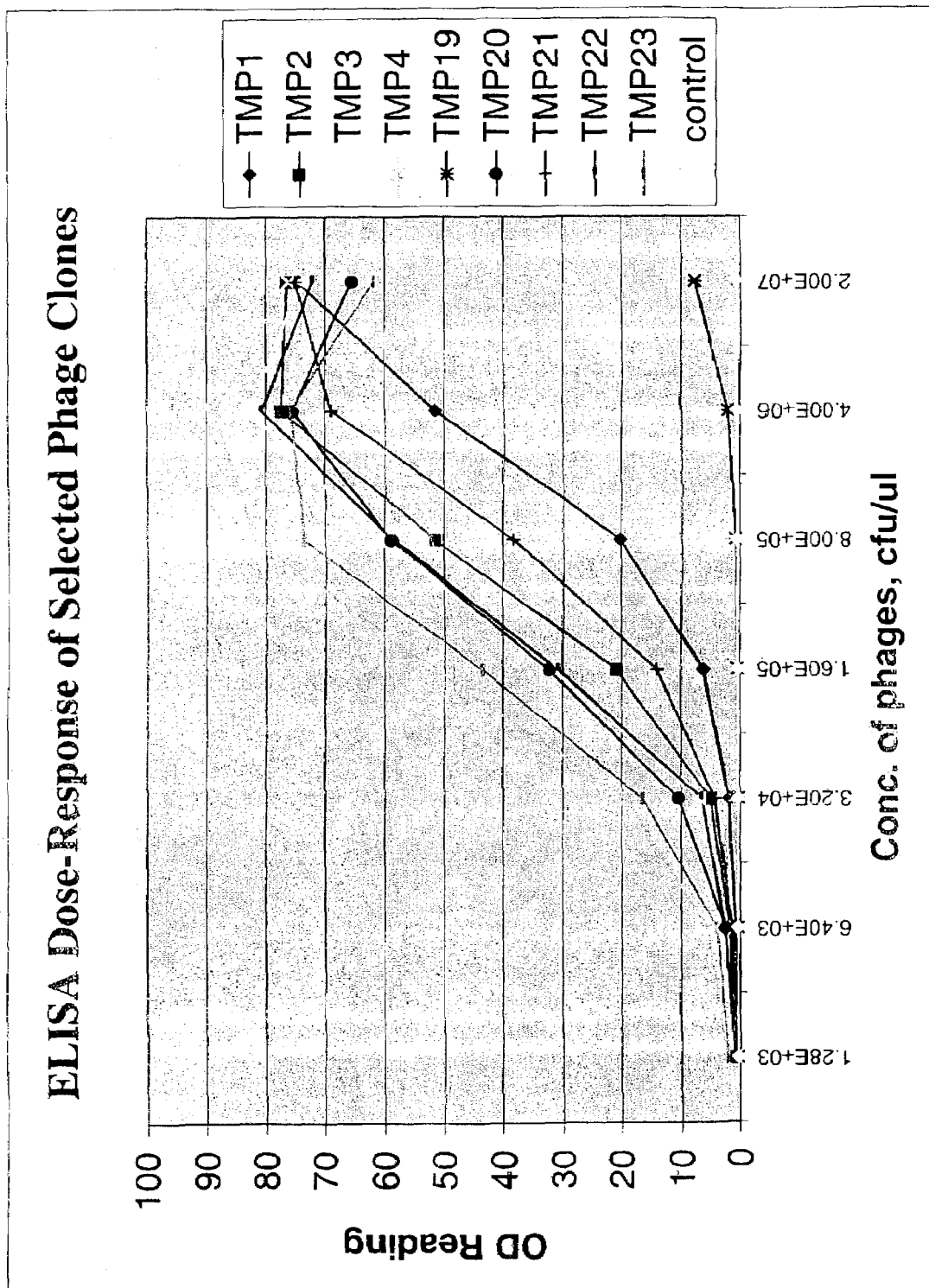
FIG. 9 shows ELISA dose-response of selected phage clones.

The terms used throughout this specification are defined as follows, unless otherwise limited in specific instances.

The term "peptide" refers to molecules of approximately 2 to 80 amino acids, with molecules of 3 to 40 amino acids preferred. Exemplary peptides may be randomly generated by any of the methods set forth herein such as carried in peptide library (e.g. phage display library), generated by chemical synthesis, derived by digestion of proteins and the like.

The term "randomized" used in connection with peptide sequences refers to fully random sequences (e.g., selected by phage display methods or RNA-peptide screening) and sequences in which one or more residues of a naturally occurring molecule is replaced by an amino acid residue not present in that position in the naturally occurring molecule. Exemplary methods for creating and identifying randomized peptide sequences include phage display, E. coli display, ribosome display, RNA-peptide screening, chemical screening, and the like.

The term "dimer" as applied to peptides refers to molecules having two peptide chains associated covalently or non-covalently, with or without linkers. Peptide dimers wherein the peptides are linked C-terminus to N-terminus may also be referred to as "tandem repeats" or "tandem dimers." Peptide dimers wherein the peptides are linked C- to C-terminus, or N- to N-terminus may also be referred to as "parallel repeats" or "parallel dimers."

The term "multimer" as applied to peptides refers to molecules having three or more peptide chains associated covalently, noncovalently, or by both covalent and non-covalent interactions, with or without linkers.

The terms "derivatizing" and "derivative" or "derivatized" involve processes and resulting compounds in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-petidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxycarbonyl—NH—wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "thrombopoietin mimetic peptide," "TPO mimetic peptide" or "TMP" refers to a peptide that binds to the mpl receptor and/or has thrombopoietic activity, i.e., the ability to stimulate, in vivo or in vitro, the production of platelets or platelet precursors, including but not limited to megakaryocytes.

The term "mpl-binding domain" refers to any amino acid sequence that binds the mpl receptor and comprises naturally occurring sequences or randomized sequences. Exemplary mpl-binding domains can be identified or derived by phage display or other methods mentioned herein.

The term "mpl receptor agonist" refers to a molecule that binds to the mpl receptor and increases or decreases one or more assay parameters as does endogenous thrombopoietin (eTPO), the native mpl receptor ligand.

The term "comprising" means that a compound may include additional amino acids on either or both of the N- or or C-termini of the given sequence. Of course, these additional amino acids should not significantly interfere with the activity of the compound.

Additionally, physiologically acceptable salts of the compounds of this invention are also encompassed herein. The term "physiologically acceptable salts" refers to any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

The term "vehicle" refers to a molecule that prevents degradation and/or increases half-life, reduces toxicity, reduces immunogenicity and/or increases biological activity of a therapeutic protein. Exemplary vehicles include an Fc domain (which is preferred) as well as a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); a carbohydrate or oligosaccharide (e.g., dextran); any natural or synthetic protein, polypeptide or peptide that binds to a salvage receptor; albumin, including human serum albumin (HSA), leucine zipper domain, and other such proteins and protein fragments.

The term "native Fc" refers to molecule or sequence comprising the sequence of a non-antigen-binding fragment resulting from digestion of whole antibody, whether in monomeric or multimeric form. The original immunoglobulin source of the native Fc is preferably of human origin and may be any of the immunoglobulins, although IgG1 and IgG2 are preferred. Native Fcs are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference in their entirety. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The term "Fc domain" encompasses native Fc and Fc variant molecules and sequences as defined above. As with Fc variants and native Fcs, the term "Fc domain" includes molecules in monomeric or multimeric form, whether digested from whole antibody or produced by other means.

The term "dimer" as applied to Fc domains or molecules comprising Fc domains refers to molecules having two polypeptide chains associated covalently or non-covalently.

The term "multimer" as applied to Fc domains or molecules comprising Fc domains refers to molecules having two or more polypeptide chains associated covalently, non-covalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined herein) such a native Fc.

The terms "peptibody" and "peptibodies" refer to molecules comprising an antibody Fc domain attached to at least one peptide. Such peptibodies may be multimers or dimers or fragments thereof, and they may be derivatized.

II. Structure of Compounds

In General. The present invention provides compounds capable of binding to and/or modulating the biological activity of the mpl receptor. More particularly, the present invention provides a group of compounds that are capable of binding to and/or triggering a transmembrane signal through, i.e., activating, the mpl receptor, which is the same receptor that mediates the activity of endogenous thrombopoietin (TPO). Thus, the inventive compounds have thrombopoietic activity, i.e., the ability to stimulate, in vivo and in vitro, the production of platelets and/or have megakaryocytopoietic activity, i.e., the ability to stimulate, in vivo and in vitro, the production of platelet precursors, including megakaryocytes.

Briefly, the compounds of the present invention comprise one or more peptides having the sequence of formula I:

$$X_1\text{-}X_2\text{-}X_3\text{-}X_4\text{-}G\text{-}P\text{-}T\text{-}L\text{-}X_9\text{-}X_{10}\text{-}W\text{-}L\text{-}X_{13}\text{-}X_{14}\text{-}X_{15}\text{-}X_{16}\text{-}X_{17}\text{-}X_{18}; \quad \text{I:}$$

wherein $X_1$-$X_4$, $X_9$-$X_{10}$, and $X_{13}$-$X_{18}$ are each independently an amino acid.

In other compositions of matter prepared in accordance with this invention, the compounds may comprise one or more peptides having the sequence of formula I attached or otherwise linked to each other, for example, as dimers or multimers.

In other compositions of matter prepared in accordance with this invention, the compounds may comprise one or more peptides of formula I which are attached or otherwise linked to a vehicle at the peptide's N-terminus or C-terminus. Any of these peptides may be linked in tandem (i.e., sequentially, N to C),or in parallel (i.e., N- to N-terminus, or C- to C-terminus) with or without linkers.

Peptides. Compounds of the present invention comprise TPO mimetic peptides, either alone or in combination with another TMP as, for example, dimers or multimers. TMPs of the present invention comprise the following sequence:

X1-X2-X3-X4-G-P-T-L-X9-X10-W-L-X13-X14-X15-X16-X17-X18;   I:

wherein X1-X4, X9-X10, and X13-X18 are each independently an amino acid. Preferred amino acid residues of the above sequence are further defined below in Table 1.

TABLE 1

Preferred Amino Acid Residues

| Position | Amino Acid Residue |
|---|---|
| X1 | A, V, W, M, G, Y, C, Q, E, R, H |
| X2 | A, V, L, I, G, S, C |
| X3 | L, I, P, W, G, S, D, K, R |
| X4 | L, G, Q, D, E, H |
| X9 | K, R |
| X10 | Q, E |
| X13 | A, V, L, S, Q, E, R |
| X14 | A, W, T, Y, C, Q |
| X15 | V, L, G, Y, R |
| X16 | A, L, F, G, R |
| X17 | A, V, L, M, G, C, Q, N |
| X18 | A, V, P, M, F, G, C, Q, K |

Even more preferred TMP sequences of the present invention are those having the sequence:

X1-X2-X3-X4-G-P-T-L-X9-X10-W-L-X13-X14-X15-X16-X17-X18;   I wherein X1-X4, X9-X10, and X13-X18 are each independently an amino acid and wherein the peptide has a binding affinity for the mpl receptor and/or a bioactivity equal to or greater than that of the sequence:

I-E-G-P-T-L-R-Q-W-L-A-A-R-A   [SEQ ID NO 1].

Binding affinity can be measured by any assay known or available to those skilled in the art, including but not limited to BIAcore measurements, ELISA assays, competition assays, etc.

Bioactivity can be measured in vivo or in vitro by any assay known or available to those skilled in the art. Exemplary assays include, but are not limited to, cell-based assays, i.e., megakaryocyte proliferation assays, 32D cell assays (an IL-3 dependent clone of murine 32D cells that have been transfected with human mpl receptor, described in greater detail in WO 95/26746), CD34+ assays, CD61 cell assays, etc. Bioactivity can also be measured by various in vivo animal assays.

Further preferred TMP sequences of the present invention are identified in Table 2 below.

TABLE 2

Preferred TMP sequences

| TMP No. | PEPTIDE SEQUENCE | SEQ ID NO: |
|---|---|---|
| TMP2 | GAREGPTLRQWLEWVRVG | 2 |
| TMP3 | RDLDGPTLRQWLPLPSVQ | 3 |
| TMP4 | ALRDGPTLKQWLEYRRQA | 4 |

TABLE 2-continued

Preferred TMP sequences

| TMP No. | PEPTIDE SEQUENCE | SEQ ID NO: |
|---|---|---|
| TMP5 | ARQEGPTLKEWLFWVRMG | 5 |
| TMP6 | EALLGPTLREWLAWRRAQ | 6 |
| TMP7 | MARDGPTLREWLRTYRMM | 7 |
| TMP8 | WMPEGPTLKQWLFHGRGQ | 8 |
| TMP9 | HIREGPTLRQWLVALRMV | 9 |
| TMP10 | QLGHGPTLRQWLSWYRGM | 10 |
| TMP11 | ELRQGPTLHEWLQHLASK | 11 |
| TMP12 | VGIEGPTLRQWLAQRLNP | 12 |
| TMP13 | WSRDGPTLREWLAWRAVG | 13 |
| TMP14 | AVPQGPTLKQWLLWRRCA | 14 |
| TMP15 | RIREGPTLKEWLAQRRGF | 15 |
| TMP16 | RFAEGPTLREWLEQRKLV | 16 |
| TMP17 | DRFQGPTLREWLAAIRSV | 17 |
| TMP18 | AGREGPTLREWLNMRVWQ | 18 |
| TMP19 | ALQEGPTLRQWLGWGQWG | 19 |
| TMP20 | YCDEGPTLKQWLVCLGLQ | 20 |
| TMP21 | WCKEGPTLREWLRWGFLC | 21 |
| TMP22 | CSSGGPTLREWLQCRRMQ | 22 |
| TMP23 | CSWGGPTLKQWLQCVRAK | 23 |
| TMP24 | CQLGGPTLREWLACRLGA | 24 |
| TMP25 | CWEGGPTLKEWLQCLVER | 25 |
| TMP26 | CRGGGPTLHQWLSCFRWQ | 26 |
| TMP27 | CRDGGPTLRQWLACLQQK | 27 |
| TMP28 | ELRSGPTLKEWLVWRLAQ | 28 |
| TMP29 | GCRSGPTLREWLACREVQ | 29 |
| TMP30 | TCEQGPTLRQWLLCRQGR | 30 |

Binding affinity and bioactivity data for the peptides TMP2-TMP30 are described further in the Examples. To better mimic the phage environment from which the peptides were selected, and to shield the charged amino- and carboxy-terminus ends of the preferred 18 amino acid peptides, two amino acid "caps" were added to each end of each peptide. In particular, glutamine (Q) and cysteine (C) were added to the amino terminus of each of TMP2-TMP30. Similarly, two amino acid "caps" were added to the carboxy terminus of each peptide—histadine (H) and serine (S). It will be appreciated by those skilled in the art that the caps merely shield the charged ends and are not intended to contribute to or detract from to the binding affinity and/or bioactivity of the preferred peptides.

Since peptide affinity is known to increase with peptide length, the benchmark bioactive peptide (SEQ ID NO 1) was increased from 14 amino acids to 22 amino acids to be the same length as the test peptides, TMP2-TMP30. See Examples 6-11. It will be understood by those skilled in the art that the bioactive region of the comparator peptide is the core 14 amino acid sequence identified as SEQ ID NO 1, and also referred to as TMP1.

Any peptide containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized as described hereinafter.

Additional useful peptide sequences may result from conservative and/or non-conservative modifications of the amino acid sequences of the TMPs disclosed herein. Conservative modifications will produce peptides having functional and chemical characteristics similar to those of the peptide from which such modifications are made. In contrast, substantial modifications in the functional and/or chemical characteristics of the peptides may be accomplished by selecting substitutions in the amino acid sequence that differ significantly in their effect on maintaining (a) the structure of the molecular backbone in the area of the substitution, for example, as a sheet or helical conformation, (b) the charge or hydrophobicity of the molecule at the target site, or (c) the size of the molecule.

For example, a "conservative amino acid substitution" may involve a substitution of a native amino acid residue with a nonnative residue such that there is little or no effect on the polarity or charge of the amino acid residue at that position. Furthermore, any native residue in the polypeptide may also be substituted with alanine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Desired amino acid substitutions (whether conservative or non-conservative) can be determined by those skilled in the art at the time such substitutions are desired. For example, amino acid substitutions can be used to identify important residues of the peptide sequence, or to increase or decrease the affinity of the peptide or vehicle-peptide molecules (see preceding formulae) described herein. Exemplary amino acid substitutions are set forth in Table 3.

TABLE 3

Amino Acid Substitutions

| Original Residues | Exemplary Substitutions | Preferred Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4 Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass non-naturally occurring amino acid residues which are typically incorporated by chemical peptide synthesis rather than by synthesis in biological systems.

Naturally occurring residues may be divided into classes based on common sidechain properties that may be useful for modifications of sequence. For example, non-conservative substitutions may involve the exchange of a member of one of these classes for a member from another class. Such substituted residues may be introduced into regions of the peptide that are homologous with non-human orthologs, or into the non-homologous regions of the molecule. In addition, one may also make modifications using P or G for the purpose of influencing chain orientation.

In making such modifications, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157: 105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

A skilled artisan will be able to determine suitable variants using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of a peptide to similar peptides. With such a comparison, one can identify residues and portions of the molecules that are conserved among similar polypeptides. It will be appreciated that changes in areas of a peptide that are not conserved relative to such similar peptides would be less likely to adversely affect the biological activity and/or structure of the peptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the peptide structure.

The amino acids may have either L or D stereochemistry (except for Gly, which is neither L nor D) and the TMPs of the present invention may comprise a combination of stereochemistries. However, the L stereochemistry is preferred for all of the amino acids in the TMP chain. The invention also provides reverse TMP molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse TMP molecules wherein, like a reverse TMP, the amino terminal to carboxy terminal sequence of amino acids is reversed and residues that are normally "L" enatiomers in TMP are altered to the "D" stereoisomer form.

It is also contemplated that "derivatives" of the TMPs may be substituted for the above-described TMPs. Such derivative TMPs include moieties wherein one or more of the following modifications have been made:

one or more of the peptidyl [—C(O)NR—] linkages (bonds) have been replaced by a non-peptidyl linkage such as a —$CH_2$-carbamate linkage [—$CH_2$—OC(O)NR—]; a phosphonate linkage; a —$CH_2$-sulfonamide [—$CH_2$—S(O)$_2$NR—] linkage; a urea [—NHC(O)NH—] linkage; a —$CH_2$-secondary amine linkage; or an alkylated peptidyl linkage [—C(O)NR$^6$— where R$^6$ is lower alkyl];

peptides wherein the N-terminus is derivatized to a —NRR$^1$ group; to a —NRC(O)R group; to a —NRC(O)OR group; to a —NRS(O)$_2$R group; to a —NHC(O)NHR group, where R and R$^1$ are hydrogen or lower alkyl, with the proviso that R and R$^1$ are not both hydrogen; to a succinimide group; to a benzyloxycarbonyl-NH— (CBZ-NH—) group; or to a benzyloxycarbonyl-NH— group having from 1 to 3 substituents on the phenyl ring selected from the group consisting of lower alkyl, lower alkoxy, chloro, and bromo; and peptides wherein the free C terminus is derivatized to —C(O)R$^2$ where R$^2$ is selected from the group consisting of lower alkoxy and —NR$^3$R$^4$ where R$^3$ and R$^4$ are independently selected from the group consisting of hydrogen and lower alkyl. By "lower" is meant a group having from 1 to 6 carbon atoms.

Additionally, modifications of individual amino acids may be introduced into the TMP molecule by reacting targeted amino acid residues of the peptide with an organic derivatizing agent that is capable of reacting with selected side chains or terminal residues. The following are exemplary:

Lysinyl and amino terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 entanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizole and tetranitromethane may be used to form O-acetyl tyrosyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues are frequently deamidated to the corresponding glutamyl and aspartyl residues. Alternatively, these residues may be deamidated under mildly acidic conditions. Either form of these residues falls within the scope of this invention.

Derivatization with bifunctional agents is useful for cross-linking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for protein immobilization.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (Creighton, T. E., Proteins: Structure and Molecule Properties, W. H. Freeman & Co., San Francisco, pp. 79-86 (1983)), acetylation of the N-terminal amine, and, in some instances, amidation of the C-terminal carboxyl groups.

Such derivatized moieties preferably improve one or more characteristics including thrombopoietic activity, solubility, absorption, biological half life, and the like of the inventive compounds. Alternatively, derivatized moieties may result in compounds that have the same, or essentially the same, characteristics and/or properties of the compound that is not derivatized. The moieties may alternatively eliminate or attenuate any undesirable side effect of the compounds and the like.

Compounds of the present invention may be changed at the DNA level, as well. The DNA sequence of any portion of the compound may be changed to codons more compatible with the chosen host cell. For E. coli, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes. Thus, all modifications, substitution, derivitizations, etc. discussed herein apply equally to all aspects of the present invention, including but not limited to peptides, peptide dimers and multimers, linkers, and vehicles.

Additionally, one skilled in the art can review structure-function studies identifying residues in similar peptides that are important for activity or structure. In view of such a comparison, one can predict the importance of amino acid residues in a peptide that correspond to amino acid residues that are important for activity or structure in similar peptides. One skilled in the art may opt for chemically similar amino acid substitutions for such predicted important amino acid residues of the peptides.

One skilled in the art can also analyze the three-dimensional structure and amino acid sequence in relation to that structure in similar polypeptides. In view of that information, one skilled in the art may predict the alignment of amino acid residues of a peptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such data could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4): 422-427 (1996), Chou et al., Biochemistry, 13(2): 222-245 (1974); Chou et al., Biochemistry, 113(2): 211-222 (1974); Chou et al., Adv. Enzymol. Relat. Areas Mol. Biol., 47: 45-148 (1978); Chou et al., Ann. Rev. Biochem., 47: 251-276 and Chou et al., Biophys. J., 26: 367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., Nucl. Acid. Res., 27(1): 244-247 (1999). It has been suggested (Brenner et al., Curr. Op. Struct. Biol., 7(3): 369-376 (1997)) that there are a limited number of folds in a given polypeptide or protein and that once a critical number of structures have been resolved, structural prediction will gain dramatically in accuracy.

Additional methods of predicting secondary structure include "threading" (Jones, D., Curr. Opin. Struct. Biol., 7(3): 377-87 (1997); Sippl et al., Structure, 4(1): 15-9 (1996)), "profile analysis" (Bowie et al., Science, 253: 164-170 (1991); Gribskov et al., Meth. Enzym., 183: 146-159 (1990); Gribskov et al., Proc. Nat. Acad. Sci., 84(13): 4355-8 (1987)), and "evolutionary linkage" (See Home, supra, and Brenner, supra).

Formulae for preferred peptide and peptide-linker molecules of the present invention are shown in FIG. 1. Additionally, physiologically acceptable salts of the TMPs are also encompassed.

Peptide Compounds

In addition to novel peptides, the present invention provides novel peptide compounds wherein one or more peptides of the present invention are attached or otherwise linked to each other, to a linker (LN) and/or to a vehicle (V). TMPs may be linked in tandem (i.e., sequentially, N-terminus terminus to C-terminus) or in parallel (i.e., N- to N-terminus terminus or C- to C-terminus). TMPs may be attached to other TMPs or the same TMPs, with or without linkers. TMPs may also be attached to other TMPs or the same TMPs with or without linkers and with or without vehicles. Peptide-linker-vehicle compounds of the present invention may be described by the following formula:

$$(V1)_v\text{—}(LN1)_l\text{—}(TMP1)_a\text{—}(LN2)_m\text{—}(TMP2)_b\text{—}(LN3)_n\text{—}(TMP3)_c\text{—}(LN4)_o\text{—}(TMP4)_d\text{—}(V2)_w \quad \text{II}$$

wherein:

V1 and V2 are vehicles; LN1, LN2, LN3 and LN4 are each independently linkers; TMP1, TMP2, TMP3 and TMP4 are each independently peptide sequences of the formula I; a, b, c and d and l, m, n and o are each independently an integer from zero to twenty, and v and w are each independently an integer from zero to one.

Exemplary compounds of the present invention are shown by the following formulae:

TMP1-V1

TMP1-LN1-V1

TMP1-TMP2-V1

TMP1-LN1-TMP2-LN2-V1 and additional multimers thereof wherein V1 is a vehicle (preferably an Fc domain) and is attached at the C-terminus of a TMP, either with or without a linker;

V1-TMP1

V1-LN1-TMP1

V1-TMP1-TMP2

V1-LN1-TMP1-LN2-TMP2 and multimers thereof wherein V1 is a vehicle (preferably an Fc domain) and is attached at the N-terminus of a TMP, either with or without a linker. Formulae for preferred peptide-vehicle and peptide-linker-vehicle molecules of the present invention are shown in FIG. 2.

Many of the preferred compounds of the invention are dimers or multimers in that they possess two TMP moieties or multimers in that they possess multiple TMP moieties. Each of TMP1 through TMP4 etc. can have the same or different structures. Preferably the compounds of the present invention will have from 2-5 TMP moieties, particularly preferably 2-3 and most preferably 2.

These compounds are preferably dimers which are either attached directly or are linked by a linker group (see below). The monomeric TMP moieties are shown in the conventional orientation from N- to C-terminus reading left to right. Accordingly, it can be seen that the inventive compounds can be oriented so that the C-terminus of TMP1 is attached either directly or through a linker to the N-terminus of TMP2 (a tandem dimer). Alternately, the inventive compounds can be oriented so that the C-terminus of TMP1 is attached either directly or through a linker to the C-terminus of TMP2, or the N-terminus of TMP1 is attached either directly or through a linker to the N-terminus of TMP2 (a parallel dimer). These compounds are referred to as dimers even if TMP 1 and TMP2 are structurally distinct. That is, both homodimers and heterodimers are envisioned.

Linkers

In another embodiment, the present invention provides one or more TMPs covalently bonded or otherwise linked or attached to another TMP peptide of via a "linker" group (LN1, LN2, etc.). Any linker group is optional. When it is present, it is not critical what its chemical structure, since it serves primarily as a spacer. The linker should be chosen so as not to interfere with the biological activity of the final compound and also so that immunogenicity of the final compound is not significantly increased. The linker is preferably made up of amino acids linked together by peptide bonds. Thus, in preferred embodiments, the linker is made up of from 1 to 30 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly)$_4$, (Gly)$_5$), poly (Gly-Ala), and polyalanines. Other specific examples of linkers are:

| | |
|---|---|
| (Gly)$_3$Lys(Gly)$_4$; | (SEQ ID NO:96) |
| (Gly)$_3$AsnGlySer(Gly)$_2$; | (SEQ ID NO:97) |
| (Gly)$_3$Cys(Gly)$_4$; and | (SEQ ID NO:98) |
| GlyProAsnGlyGly. | (SEQ ID NO:99) |

To explain the above nomenclature, for example, (Gly)$_3$Lys (Gly)$_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as —NH—(CH$_2$)$_s$—C(O)—, wherein s=2–20 could be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker,

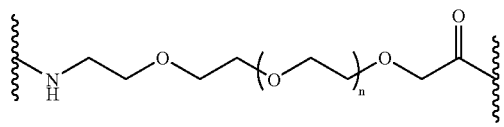

wherein n is such that the linker has a molecular weight of 100 to 5000 kD, preferably 100 to 500 kD. The peptide linkers may be altered to form derivatives in the same manner as described above.

In general, it has been discovered that a linker of a length of about 0-14 sub-units (e.g., amino acids) is preferred for the thrombopoietic compounds of the present invention. The peptide linkers may be altered to form derivatives in the same manner as described above for the TMPs. In addition, the compounds of this embodiment may further be linear or cyclic. By "cyclic" is meant that at least two separated, i.e., non-contiguous, portions of the molecule are linked to each other. For example, the amino and carboxy terminus of the ends of the molecule could be covalently linked to form a cyclic molecule. Alternatively, the molecule could contain two or more Cys residues (e.g., in the linker), which could cyclize via disulfide bond formation. It is further contemplated that more than one tandem peptide dimer can link to form a dimer of dimers. Thus, for example, a tandem dimer containing a Cys residue can form an intermolecular disulfide bond with a Cys of another such dimer. Exemplary peptide-linker compounds of the invention are shown below:

| | |
|---|---|
| CSSGGPTLREWLQCRRMQ --GGGGG-- CSSGGPTLREWLQCRRMQ; | (SEQ ID NO 100) |
| QLGHGPTLRQWLSWYRGM--(Gly)$_3$Lys(Gly)$_4$--ALRDGPTLKQWLEYRRQA; | (SEQ ID NO 101) |
| RFAEGPTLREWLEQRKLV-GGG(PEG)GGG- RFAEGPTLREWLEQRKLV. | (SEQ ID NO 102) |

Thus, in preferred embodiments, the linker comprises (LN1)$_n$, wherein LN1 is a naturally occurring amino acid or a stereoisomer thereof and "n" is any one of 1 through 20. Formulae for preferred peptide-linker molecules are shown in FIG. 1. Further preferred peptide-linker molecules include:

i) TMP1-LN1-TMP2-LN2
ii) LN1-TMP1-LN2-TMP2
iii) LN1-TMP1-LN2-TMP1
iv) TMP1-LN1-TMP1-LN1-TMP1-LN1
v) LN1-TMP1-LN2-TMP2-LN3-TMP3-LN4-TMP4 wherein LN1-LN4 are each independent linkers.

Vehicles

In yet another embodiment, peptides or peptide compounds of the present invention may be linked or attached to a vehicle (V). A vehicle generally refers to a molecule that prevents degradation and/or increases half-life, reduces toxicity, reduces immunogenicity, or increases biological activity of a therapeutic protein. The vehicle (V) may be attached to a peptide through the N-terminus, C terminus, peptide backbone or a sidechain.

The vehicle (V) may be a carrier molecule, such as a linear polymer (e.g., polyethylene glycol, polylysine, dextran, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published Oct. 28, 1993); a lipid; a cholesterol group (such as a steroid); or a carbohydrate or oligosaccharide. Other possible carriers include one or more water soluble polymer attachments such as polyoxyethylene glycol, or polypropylene glycol as described U.S. Pat. Nos: 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyehtylene glycol, propylene glycol homopolymers, a polypropylene oxide/ethylene oxide co-polymer, polyoxyethylated polyols (e.g., glycerol) and polyvinyl alcohol, as well as mixtures of these polymers. Exemplary vehicles also include:
an Fc domain;
other proteins, polypeptides, or peptides capable of binding to a salvage receptor;
human serum albumin (HSA);
a leucine zipper (LZ) domain;
polyethylene glycol (PEG), including 5 kD, 20 kD, and 30 kD PEG, as well as other polymers;
dextran; and other molecules known in the art to provide extended half-life and/or protection from proteolytic degradation or clearance.

An exemplary carrier is polyethylene glycol (PEG). The PEG group may be of any convenient molecular weight and may be straight chain or branched. The average molecular weight of the PEG will preferably range from about 2 kDa to about 100 kDa, more preferably from about 5 kDa to about 50 kDa, most preferably from about 5 kDa to about 10 kDa.

The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, -haloacetyl, maleimido or hydrazino group) to a reactive group on the target compound (e.g., an aldehyde, amino, ester, thiol, -haloacetyl, maleimido or hydrazino group).

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids not including proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

In a more preferred embodiment, the vehicle (V) may comprise one or more antibody Fc domains. Thus, the peptide compounds described above may further be fused to one or more Fc domains, either directly or through linkers. The Fc vehicle may be selected from the human immunoglobulin IgG-1 heavy chain, see Ellison, J. W. et al., Nucleic Acids Res. 10:4071-4079 (1982), or any other Fc sequence known in the art (e.g. other IgG classes including but not limited to IgG-2, IgG-3 and IgG-4, or other immunoglobulins).

It is well known that Fc regions of antibodies are made up of monomeric polypeptide segments that may be linked into dimeric or multimeric forms by disulfide bonds or by non-covalent association. The number of intermolecular disulfide bonds between monomeric subunits of native Fc molecules ranges from 1 to 4 depending on the class (e.g., IgG, IgA, IgE) or subclass (e.g., IgG1, IgG2, IgG3, IgA1, IgA2) of antibody involved. The term "Fc" as used herein is generic to the monomeric, dimeric, and multimeric forms of Fc molecules. It should be noted that Fc monomers will spontaneously dimerize when the appropriate Cys residues are present unless particular conditions are present that prevent dimerization through disulfide bond formation. Even if the Cys residues that normally form disulfide bonds in the Fc dimer are removed or replaced by other residues, the monomeric chains will generally dimerize through non-covalent interactions. The term "Fc" herein is used to mean any of these forms: the native monomer, the native dimer (disulfide bond linked), modified dimers (disulfide and/or non-covalently linked), and modified monomers (i.e., derivatives).

Variants, analogs or derivatives of the Fc portion may be constructed by, for example, making various substitutions of residues or sequences.

Variant (or analog) polypeptides include insertion variants, wherein one or more amino acid residues supplement an Fc amino acid sequence. Insertions may be located at either or both termini of the protein, or may be positioned within internal regions of the Fc amino acid sequence. Insertional variants with additional residues at either or both termini can include for example, fusion proteins and proteins including amino acid tags or labels. For example, the Fc molecule may optionally contain an N-terminal Met, especially when the molecule is expressed recombinantly in a bacterial cell such as *E. coli*.

In Fc deletion variants, one or more amino acid residues in an Fc polypeptide are removed. Deletions can be effected at one or both termini of the Fc polypeptide, or with removal of one or more residues within the Fc amino acid sequence. Deletion variants, therefore, include all fragments of an Fc polypeptide sequence.

In Fc substitution variants, one or more amino acid residues of an Fc polypeptide are removed and replaced with alternative residues. In one aspect, the substitutions are conservative in nature, however, the invention embraces substitutions that are also non-conservative.

For example, cysteine residues can be deleted or replaced with other amino acids to prevent formation of some or all disulfide crosslinks of the Fc sequences. One may remove each of these cysteine residues or substitute one or more such cysteine residues with other amino acids, such as Ala or Ser. As another example, modifications may also be made to introduce amino acid substitutions to (1) ablate the Fc receptor binding site; (2) ablate the complement (C1q) binding site; and/or to (3) ablate the antibody dependent cell-mediated cytotoxicity (ADCC) site. Such sites are known in the art, and any known substitutions are within the scope of Fc as used herein. For example, see *Molecular Immunology*, Vol. 29, No. 5, 633-639 (1992) with regards to ADCC sites in IgG1.

Likewise, one or more tyrosine residues can be replaced by phenylalanine residues as well. In addition, other variant amino acid insertions, deletions (e.g., from 1-25 amino acids) and/or substitutions are also contemplated and are within the scope of the present invention. Conservative amino acid substitutions will generally be preferred. Furthermore, alterations may be in the form of altered amino acids, such as peptidomimetics or D-amino acids.

Fc sequences of the present invention may also be derivatized, i.e., bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase circulating half-life, or may be designed to improve targeting capacity for the polypeptide to desired cells, tissues, or organs.

It is also possible to use the salvage receptor binding domain of the intact Fc molecule as the Fc part of the inventive compounds, such as described in WO 96/32478, entitled "Altered Polypeptides with Increased Half-Life". Additional members of the class of molecules designated as Fc herein are those that are described in WO 97/34631, entitled "Immunoglobulin-Like Domains with Increased Half-Lives". Both of the published PCT applications cited in this paragraph are hereby incorporated by reference.

The Fc fusions may be at the N- or C-terminus of $TMP_1$ or $TMP_2$ or at both the N- and C-termini of $TMP_1$ or $TMP_2$. Similarly, the Fc fusions may be at the N-or C-terminus of the Fc domain.

Preferred compounds of the present invention include IgG1 Fc fusion dimers linked or otherwise attached to dimers or multimers of the TMPs disclosed herein. In such cases, each Fc domain will be linked to a dimer or multimer of TMP peptides, either with or without linkers. Schematic examples of such compounds are shown in FIG. 2.

Multiple vehicles may also be used; e.g., Fc's at each terminus or an Fc at a terminus and a PEG group at the other terminus or a sidechain.

Exemplary peptide-vehicle compounds are provided in Table 4 below.

TABLE 4

Exemplary Peptide-Vehicle Compounds

| AMINO ACID SEQUENCE | SEQ ID NO: |
|---|---|
| HIREGPTLRQWLVALRMV-GGG(PEG)GGG-HIREGPTLRQWLVALRMV | 153 |
| Fc-TCEQGPTLRQWLLCRQGR-GGGKGGG-TCEQGPTLRQWLLCRqGR-Fc | 154 |
| Fc-QLGHGPTLRQWLSWYRGM-GPNG-ELRSGPTLKEWLVWRLAq | 155 |
| CSWGGPTLKQWLQCVRAK-Fc<br>\|<br>SWGGPTLKQWLQCVRAK | 156 |
| Fc-GGGKGGG-AVPQGPTLKQWLLWRRCA | 157 |
| PEG-CSSGGPTLREWLQCRRMQ<br>\|<br>CSSGGPTLREWLQCRRMQ | 158 |
| Fc-GGGGG-YCDEGPTLKQWLVCLGLQ-GGGGG-YCDEGPTLKQWLVCLGLQ | 159 |
| CSWGGPTLKQWLQCVRAK-GGGAGGG-CSWGGPTLKQWLQCVRAK-GGGAGGG-<br>CSWGGPTLKQWLQCVRAK-GGGAGGG-Fc | 160 |
| VGIEGPTLRQWLAQRLNP-GGGCGGG-VGIEGPTLRQWLAQRLNP-PEG | 161 |
| Fc-ELRSGPTLKEWLVWRLAq-GGGG-ELRSGPTLKEWLVWRLAQ | 162 |
| Fc-ALRDGPTLKQWLEYRRQA-GGGKGGG-ALRDGPTLKQWLEYRRQA-Fc | 163 |

Further, preferred embodiments of the present invention are listed in Table 5.

TABLE 5

Specific Preferred Embodiments

| AMINO ACID SEQUENCE | SEQ ID NO: |
|---|---|
| ALRDGPTLKQWLEYRRQA-ALRDGPTLKQWLEYRRQA | 164 |
| EALLGPTLREWLAWRPAQ-EALLGPTLREWLAWRRAQ | 165 |
| AVPQGPTLKQWLLWRRCA-AVPQGPTLKQWLLWRRCA | 166 |
| YCDEGPTLKQWLVCLGLQ-YCDEGPTLKQWLVCLGLQ | 167 |
| CSSGGPTLREWLQCRRMQ-CSSGGPTLREWLQCRRMQ | 168 |
| CSWGGPTLKQWLQCVRAK-CSWGGPTLKQWLQCVRAK | 169 |
| ALRDGPTLKQWLEYRRQA-GGGGG-ALRDGPTLKQWLEYRRQA | 170 |
| EALLGPTLREWLAWRRAQ-GGGGG-EALLGPTLREWLAWRRAQ | 171 |

TABLE 5-continued

Specific Preferred Embodiments

| AMINO ACID SEQUENCE | SEQ ID NO: |
|---|---|
| AVPQGPTLKQWLLWRRCA-GGGGG-AVPQGPTLKQWLLWRRCA | 172 |
| YCDEGPTLKQWLVCLGLQ-GGGGG-YCDEGPTLKQWLVCLGLQ | 173 |
| CSSGGPTLREWLQCRRMQ-GGGGG-CSSGGPTLREWLQCRRMQ | 174 |
| CSWGGPTLKQWLQCVRAK-GGGGG-CSWGGPTLKQWLQCVRAK | 175 |
| Fc-GGGGG-ALRDGPTLKQWLEYRRQA | 176 |
| Fc-GGGGG-EALLGPTLREWLAWRRAQ | 177 |
| Fc-GGGGG-AVPQGPTLKQWLLWRRCA | 178 |
| Fc-GGGGG-YCDEGPTLKQWLVCLGLQ | 179 |
| Fc-GGGGG-CSSGGPTLREWLQCRRMQ | 180 |
| Fc-GGGGG-CSWGCPTLKQWLQCVRAK | 181 |
| Fc-GGGGG-ALRDGPTLKQWLEYRRQA-GGGGG-ALRDGPTLKQWLEYRRQA | 182 |
| Fc-GGGGG-EALLGPTLREWLAWRRAQ-GGGGG-EALLGPTLREWLAWRRAQ | 183 |
| Fc-GGGGG-AVPQGPTLKQWLLWRRCA-GGGGG-AVPQGPTLKQWLLWRRCA | 184 |
| Fc-GGGGG-YCDEGPTLKQWLVCLGLQ-GGGGG-YCDEGPTLKQWLVCLGLQ | 185 |
| Fc-GGGGG-CSSGGPTLREWLQCRRMQ-GGGGC-CSSGGPTLREWLQCRRMQ | 186 |
| Fc-GGGGG-CSWGGPTLKQWLQCVRAK-GGGGG-CSWGGPTLKQWLQCVRAK | 187 |
| ALRDGPTLKQWLEYRRQA-GGGGG-ALRDGPTLKQWLEYRRQA-GGGGG-Fc | 188 |
| EALLGPTLREWLAWRRAQ-GGGGG-EALLGPTLREWLAWRRAQ-GGGGG-Fc | 189 |
| AVPQGPTLKQWLLWRRCA-GGGGG-AVPQGPTLKQWLLWRRCA-GGGGG-Fc | 190 |
| YCDEGPTLKQWLVCLGLQ-GGGGG-YCDEGPTLKQWLVCLGLQ-GGGGG-Fc | 191 |
| CSSGGPTLREWLQCRRMQ-GGGGG-CSSGGPTLREWLQCRPMQ-GGGGG-Fc | 192 |
| CSWGGPTLKQWLQCVRAK-GGGGG-CSWCGPTLKQWLQCVRAK-GGGGG-Fc | 193 |
| ALRDGPTLKQWLEYRRQA-GGGGG-Fc | 194 |
| EALLGPTLREWLAWRRAQ-GGGGG-Fc | 195 |
| AVPQGPTLKQWLLWRRCA-GGGGG-Fc | 196 |
| YCDEGPTLKQWLVCLGLQ-GGGGG-Fc | 197 |
| CSSGGPTLREWLQCRRMQ-GGGGG-Fc | 198 |
| CSWGGPTLKQWLQCVRAK-GGGGG-Fc | 199 |

III. Methods of Making

The compounds of this invention may be made in a variety of ways. Since many of the compounds are peptides, or include a peptide, methods for synthesizing peptides are of particular relevance here. Solid phase synthesis techniques may be used. Suitable techniques are well known in the art, and include those described in Merrifield, in Chem. Polypeptides, pp. 335-61 (Katsoyannis and Panayotis eds. 1973); Merrifield, J. Am. Chem. Soc. 85:2149 (1963); Davis et al., Biochem. Intl. 10:394-414 (1985); Stewart and Young, Solid Phase Peptide Synthesis (1969); U.S. Pat. No. 3,941,763; Finn et al., The Proteins, 3rd ed., vol. 2, pp. 105-253 (1976); and Erickson et al., The Proteins, 3rd ed., vol. 2, pp. 257-527 (1976). Solid phase synthesis is the preferred technique of making individual peptides since it is the most cost-effective method of making small peptides.

The peptides may also be made in transformed host cells using recombinant DNA techniques. To do so, a recombinant DNA molecule coding for the peptide is prepared. Methods of preparing such DNA and/or RNA molecules are well known in the art. For instance, sequences coding for the peptides could be excised from DNA using suitable restriction enzymes. The relevant sequences can be created using the polymerase chain reaction (PCR) with the inclusion of useful restriction sites for subsequent cloning. Alternatively, the DNA/RNA molecule could be synthesized using chemical synthesis techniques, such as the phosphoramidite method. Also, a combination of these or other techniques could be used.

The invention also includes a vector encoding the peptides in an appropriate host. The vector comprises the DNA molecule that encodes the peptides operatively linked to appropriate expression control sequences. Methods of effecting this operative linking, either before or after the peptide-encoding DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector comprising the peptide-encoding DNA molecule is used to transform an appropriate host. This transformation may be performed using methods well known in the art.

Any of a large number of available and well-known host cells may be used in the practice of this invention. The selection of a particular host is dependent upon a number of factors recognized by the art. These factors include, for example, compatibility with the chosen expression vector, toxicity to the host cell of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli*), yeast (such as *Saccharomyces* sp. and *Pichia pastoris*) and other fungi, insects, plants, mammalian (including human) cells in culture, or other hosts known in the art. The transformed host is cultured under conventional fermentation conditions so that the desired peptides are expressed. Such fermentation conditions are well known in the art. The peptides are then purified from the fermentation culture or from the host cells in which they are expressed. These purification methods are also well known in the art.

Compounds that contain derivatized peptides or which contain non-peptide groups may be synthesized by well-known organic chemistry techniques. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides.

IV. Uses of the Compounds

The compounds of this invention have the ability to bind to and/or activate the mpl receptor, and/or have the ability to stimulate the production (both in vivo and in vitro) of platelets ("thrombopoietic activity") and platelet precursors ("megakaryocytopoietic activity"). To measure the activity (-ies) of these compounds, one can utilize standard assays, such as those described in WO95/26746 entitled "Compositions and Methods for Stimulating Megakaryocyte Growth and Differentiation". In vivo assays are further described in the Examples section herein.

The conditions to be treated by the methods and compositions of the present invention are generally those which involve an existing megakaryocyte/platelet deficiency or an expected or anticipated megakaryocyte/platelet deficiency in the future (e.g., because of planned surgery or platelet donation). Such conditions may be the result of a deficiency (temporary or permanent) of active mpl ligand in vivo. The generic term for platelet deficiency is thrombocytopenia, and hence the methods and compositions of the present invention are generally available for prophylactically or therapeutically treating thrombocytopenia in patients in need thereof.

The World Health Organization has classified the degree of thrombocytopenia on the number of circulating platelets in the individual (Miller, et al., Cancer 47:210-211 (1981)). For example, an individual showing no signs of thrombocytopenia (Grade 0) will generally have at least 100,000 platelets/mm$^3$. Mild thrombocytopenia (Grade 1) indicates a circulating level of platelets between 79,000 and 99,000/mm$^3$. Moderate thrombocytopenia (Grade 2) shows between 50,000 and 74,000 platelets/mm$^3$ and severe thrombocytopenia is characterized by between 25,000 and 49,000 platelets/mm$^3$. Life-threatening or debilitating thrombocytopenia is characterized by a circulating concentration of platelets of less than 25,000/mm$^3$.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia; idiopathic or immune thrombocytopenia (ITP), including idiopathic thrombocytopenic purpura associated with breast cancer; HIV associated ITP and HIV-related thrombotic thrombocytopenic purpura; metastatic tumors which result in thrombocytopenia; systemic lupus erythematosus; including neonatal lupus syndrome splenomegaly; Fanconi's syndrome; vitamin B12 deficiency; folic acid deficiency; May-Hegglin anomaly; Wiskott-Aldrich syndrome; chronic liver disease; myelodysplastic syndrome associated with thrombocytopenia; paroxysmal nocturnal hemoglobinuria; acute profound thrombocytopenia following C7E3 Fab (Abciximab) therapy; alloimmune thrombocytopenia, including maternal alloimmune thrombocytopenia; thrombocytopenia associated with antiphospholipid antibodies and thrombosis; autoimmune thrombocytopenia; drug-induced immune thrombocytopenia, including carboplatin-induced thrombocytopenia, heparin-induced thrombocytopenia; fetal thrombocytopenia; gestational thrombocytopenia; Hughes' syndrome; lupoid thrombocytopenia; accidental and/or massive blood loss; myeloproliferative disorders; thrombocytopenia in patients with malignancies; thrombotic thrombocytopenia purpura, including thrombotic microangiopathy manifesting as thrombotic thrombocytopenic purpura/hemolytic uremic syndrome in cancer patients; autoimmune hemolytic anemia; occult jejunal diverticulum perforation; pure red cell aplasia; autoimmune thrombocytopenia; nephropathia epidemica; rifampicin-associated acute renal failure; Paris-Trousseau thrombocytopenia; neonatal alloimmune thrombocytopenia; paroxysmal nocturnal hemoglobinuria; hematologic changes in stomach cancer; hemolytic uremic syndromes in childhood; hematologic manifestations related to viral infection including hepatitis A virus and CMV-associated thrombocytopenia. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The compounds of this invention may also be useful in stimulating certain cell types other than megakaryocytes if such cells are found to express mpl receptor. Conditions associated with such cells that express the mpl receptor, which are responsive to stimulation by the mpl ligand, are also within the scope of this invention.

The compounds of this invention may be used in any situation in which production of platelets or platelet precursor cells is desired, or in which stimulation of the mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The compounds of this invention may also be useful in maintaining the viability or storage life of platelets and/or megakaryocytes and related cells. Accordingly, it could be useful to include an effective amount of one or more such compounds in a composition containing such cells.

By "mammal" is meant any mammal, including humans, domestic animals including dogs and cats; exotic and/or zoo animals including monkeys; laboratory animals including mice, rats, and guinea pigs; farm animals including horses, cattle, sheep, goats, and pigs; and the like. The preferred mammal is human.

V. Pharmaceutical Compositions

The present invention also provides pharmaceutical compositions and methods of using pharmaceutical compositions of the inventive compounds. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of theobroma. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K., Modern Pharmaceutics, Edited by G. S. Banker and C. T. Rhodes Chapter 10, 1979, herein incorporated by reference. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline (Abuchowski and Davis, Soluble Polymer-Enzyme Adducts, Enzymes as Drugs, Hocenberg and Roberts, eds., Wiley—Interscience, New York, N.Y., (1981), pp 367-383; Newmark, et al., J. Appl. Biochem. 4:185-189 (1982)). Other polymers that could be used are poly-1,3-dioxolane and poly-1,3,6-tioxocane. Preferred for pharmaceutical usage, as indicated above, are polyethylene glycol moieties.

For the oral delivery dosage forms, it is also possible to use a salt of a modified aliphatic amino acid, such as sodium N-(8-[2-hydroxybenzoyl] amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, -lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the compound are for instance the fatty acids oleic acid, linoleic acid and linolenic acid.

Controlled release formulation may be desirable. The drug could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl.5): s.143-146 (1989)(endothelin-1); Hubbard et al., Annals of Internal Medicine 3:206-212 (1989)(1-antitrypsin); Smith et al., J. Clin. Invest. 84:1145-1146 (1989)(1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140:3482-3488 (1988)(interferon- and tumor necrosis factor) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 µm (or microns), most preferably 0.5 to 5 µm, for most effective delivery to the distal lung.

Carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Dosages

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors.

The inventive compounds may be administered by an initial bolus followed by a continuous infusion to maintain therapeutic circulating levels of drug product. As another example, the inventive compound may be administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood levels dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

The therapeutic methods, compositions and compounds of the present invention may also be employed, alone or in combination with other cytokines, soluble mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, JL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor 1, glial cell line-derived neutrophic factor receptor 2, growth related protein, growth related protein, growth related protein, growth related protein, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor, platelet derived growth factor receptor, pre-B cell growth stimulating factor, stem cell factor receptor, TNF, including TNF0, TNF1, TNF2, transforming growth factor, transforming growth factor, transforming growth factor 1, transforming growth factor 1.2, transforming growth factor 2, transforming growth factor 3, transforming growth factor 5, latent transforming growth factor 1, transforming growth factor binding protein I, transforming growth factor binding protein II, transforming growth factor binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. It may further be useful to administer, either simultaneously or sequentially, an effective amount of a soluble mammalian mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

EXAMPLES

The following sets forth exemplary methods for making and characterizing some of the compounds disclosed herein.

Example 1

1. Construction of Secondary Peptide Libraries
    A. Preparation of Electrocompetent *E.coli* Cells:

Overnight *E. coli* (TG1 strain; Amersham Pharmacia Biotech, Piscataway, N.J.) culture was prepared in 10 ml of 2×YT medium (1.6% Bacto Tryptone, 1% Yeast Extract, 85.5 mM NaCl) at 37° C. One milliliter of this overnight culture was used to inoculate 1 liter of 2×YT medium containing 0.4% glucose and 10 mM $MgCl_2$, and this one liter culture was grown in a shaker at 37° C. until $OD_{600}$=0.8. The culture was chilled on ice for 15 min and centrifuged at 4000 rpm (Beckman JA-10 rotor) for 20 min at 4° C. The bacteria pellets were resuspended in 500 ml of ice-chilled 10% glycerol solution, and the resulting mixture was centrifuged at 4000 rpm for 20 min at 4° C. The bacteria pellets were resuspended again in 500 ml of ice-chilled 10% glycerol solution, and the resulting mixture again was centrifuged at 4000 rpm for 20 min at 4° C. The cell pellets were then resuspended in 25 ml of ice-chilled 10% glycerol solution. This concentrated bacteria sample was transferred to ice-chilled 50 ml conical tube and centrifuged at 3500 rpm in a tabletop centrifuge (Beckman CS-6R) for 15 min at 4° C. The cell pellets were resuspended in a small volume of ice-chilled glycerol solution, and 100 or 300 µl bacteria stocks were immediately frozen in an ethanol/dry-ice bath and stored in −80° C. freezer.

B. Modification of pCES1 Vector

PCR reaction was performed using Extend Long Template PCR Systems (Roche Diagnostics Corp., Indianapolis, Ind.) with 1 µg of pCES1 vector (TargetQuest Inc.) as a template. The volume of PCR mixture was 100 µl which contains 1×PCR buffer, 200 nM of each of the two primer 5'-CAAACGAATGGATCCTCATTAAAGCCAGA-3' and 5'-GGTGGTGCGGCCGCACTCGAGACTGT-TGAAAGTTGTTTAGCA-3', 200 nM dNTP, 3 U of Taq DNA polymerase. The TRIO-Thermoblock (Biometra) PCR system was used to run the following program: 94° C. for 5 min; 30 cycles of [94° C. for 30 second, 50° C. for 30 second, 72° C. for 45 second]; 72° C. for 10 min; cool to 4° C. The PCR products were run on a 1% agarose gel and purified with QIAGEN Spin Column (QIAGEN Inc., Valencia, Calif.) according to the manufacturer's protocols. A second PCR reaction was performed with 5 µl of PCR products and 200 nM of each of the two primer 5'-CAAAC-GAATGGATCCTCATTAAAGCCAGA-3' and 5'-AACA-CAAAAGTGCACAGGGTGGAGGTGGTGGT-GCGGCCGCACT-3' under the same PCR conditions as described above.

The PCR products and original pCES1 vector were digested separately in a 100 µl reaction containing 1×NEB2 buffer, 60 U of ApaLI (New England Biolabs, Beverly, Mass.), 60 U of BamHI (New England Biolabs) at 37° C. for 1 hr. Both digested DNA were purified with QIAGEN Spin Column and ligated together in a 40 µl reaction containing 1× ligation buffer and 40 U of T4 DNA ligase (New England Biolabs) at room temperature overnight.

The vectors were transfected into *E. coli* and incubated at 37° C. overnight. Isolated single colonies were selected and plasmid was purified with QIAGEN Spin Column. The correct insert was confirmed by DNA sequencing.

C. Preparation of Vector DNA

One microgram of the modified pCES1 vector DNA (section 1B) was transformed into 100 μl of electrocompetent TG1 *E.coli* (section 1A) using the Gene Pulser II (BIO-RAD, Hercules, Calif.) with the setting of 2500 V, 25° F., and 200 ohms. The transformed bacteria sample was then transferred immediately into a tube containing 900 μl of SOC (2% tryptone, 0.5% yeast extract, 10 mM NaCl, 2.5 mM KCl, 20 mM glucose, 10 mM $MgSO_4$, 10 mM $MgCl_2$), and this culture was allowed to grow at 37° C. with shaking for 1 hour. The cells were then spread onto the 2×YTAG (2×YT with 100 ug/ml ampicillin and 2% glucose) agar plate and incubated at 37° C. overnight. A single colony was used to inoculate 1 liter of 2×YTAG media at 37° C. with shaking overnight. The plasmid vector DNA was purified with QIAGEN Plasmid Maxi Kit according to the manufacturer's protocols.

D. Digestion of Vector DNA

Fifty microgram of vector DNA (section 1C) was digested in a 400 μl reaction containing 1×NEB buffer2, 200 U of ApaLI, and 200 U of XhoI at 37° C. overnight. This restriction digest reaction was incubated overnight at 37° C. and analyzed in a pre-made 1% agarose gel (Embi Tec, San Diego, Calif.). The linearized vector DNA was excised from the gel and extracted with QIAquick Gel Extraction Kit (QIAGEN Inc.) according to the manufacturer's directions.

E. Preparation of Library Oligonucleotides

Two library oligonucleotides (fixed and doped) were designed. The fixed library oligonucleotide 5'-CACAGTG-CACAGGGTNNKNNKNNKNNKGGTC-CTACTCTGMRKSARTGGCTGNNKNNKNNK NNKNNKNNKCATTCTCTCGAGATCG-3' and the doped library oligonucleo-tide 5'-CACAGTGCAC-AGGGTNN-KNNKNNKNNKggKcc-KacKctKNNKNNKtgKNNKNN-KNNKNNKNNKNNKNNKCATTCTCTCGAGATCG-3' (lower case letters represent a mixture of 70% of the indicated base and 10% of each of the other three nucleotides) were synthesized. Each of these oligonucleotides was used as templates in Polymerase Chain Reactions.

Expand High Fidelity PCR System kit (Roche Diagnostics Corp.) was used for the PCR reactions. Each PCR reaction was 100 μl in volume and contained 10 nM of a library oligonucleotide, 1×PCR buffer, 300 nM of each of the primers 5'-CACAGTGCACAGGGT-3' and 5'-TGATCTCGAGAGAATG-3', 200 nM dNTP, 2 mM $CaCl_2$, and 5 U of the Expand polymerase. The thermocycler (GeneAmp PCR System 9700, Applied Biosystem) was used to run the following program: 94° C. for 5 min; 30 cycles of [94° C. for 30 second, 55° C. for 30 second, 72° C. for 45 second]; 72° C. for 7 min; cool to 4° C. The free nucleotides were removed using the QIAquick Nucleotide Removal Kit (QIAGEN Inc.) according to the manufacturer's protocols.

F. Digestion of Library Oligonucleotides

Five microgram of the each of the PCR products (section 1E) was digested in a 400 μl reaction that contained 1×NEB buffer2, 200 U of ApaLI, and 200 U of XhoI at 37° C. overnight. The digested DNA was separated on a 3% agarose gel (Embi Tec). The DNA band of interest from each reaction was cut from the gel and extracted with QIAquick Gel Extraction Kit.

G. Ligation of Vector with Library Oligonucleotides

The linearized vector (section 1D, 25 μg) and each digested PCR product (section 1F, 5 ug) were ligated in a 400 μl reaction containing 1×NEB ligation buffer and 80 U of the T4 DNA ligase at 16° C. overnight. The ligated products were incubated at 65° C. for 20 minutes to inactivate the DNA ligase and further incubated with 8 U NotI at 37° C. for 2 hr to minimize vector self-ligation. The ligated products were then purified by a standard phenol/chloroform extraction (Molecular Cloning, Maniatis et al $3^{rd}$ Edition) and resuspended in 30 μl of $H_2O$.

H. Electroporation Transformation

For each library, ten electroporation reactions were performed. For each transformation, 3 μl of the ligated vector DNA (section 1G) and 300 μl of TG1 cells (section 1A) were mixed in a 0.2-cm cuvette (BIO-RAD). The resulting mixture was pulsed by the Gene Pulser II with the setting of 2500 V, 25 uF, and 200 ohms. The transformed bacteria samples from the ten electroporation reactions were combined and transferred into a flask containing 27 ml of SOC for incubation at 37° C. for 1 hr. The cells were then added to 170 ml 2×YTAG and grew at 37° C. with shaking for 3 hrs. The cells were centrifuged at 5000 rpm for 10 min at 4° C. The cell pellets were then resuspended in 10 ml of 15% glycerol/2×YT and stored at −80° C. This is the primary stock of the libraries. Titers showed library sizes of $1.0 \times 10^9$ independent transformants and $2.4 \times 10^9$ independent transformants for the fixed and doped library, respectively.

2. Amplification of the Libraries

A. Making Secondary Stock of the Libraries

The primary library cell stock (section 1H) was used to inoculate 1300 ml (for fixed library) and 2600 ml (for doped library) of 2×YTAG media so that the starting $OD_{600}=0.1$. The cultures were allowed to grow at 37° C. with shaking for several hours until $OD_{600}=0.5$. A 120 ml aliquot for the fixed library and a 240 ml aliquot for the doped library were taken out and grown up in separate flasks for another two hours at 37° C. These sub-cultures were centrifuged at 5000 rpm (Beckman JA-14 rotor) for 10 min at 4° C., and the bacteria pellets were resuspended in 10 ml (for each library) of 15% glycerol/2×YT for storage at −80° C.

B. Phage Induction

M13KO7 helper phage aliquots (Amersham Pharmacia Biotech) were added to the remaining bacteria cultures at $OD_{600}=0.5$ (section 2A) to the final concentration of $3 \times 10^9$ pfu/ml. The helper phages were allowed to infect bacteria at 37° C. for 30 min without shaking and 30 min with slow shaking. The infected cells were centrifuged with 5000 rpm for 10 min at 4° C. The cell pellets were resuspended with 1300 ml (fixed library) and 2600 ml (doped library) of 2×YTAK (2YT with 100 ug/ml ampicillin and 40 ug/ml kanamycin). The phagemid production was allowed to occur at 37° C. overnight while shaking.

C. Harvest of Phage

The bacteria cultures (section 2B) were centrifuged at 5000 rpm for 10 min at 4° C. The supernatants were transferred into new bottles, and 0.2 volume of 20% PEG/2.5M NaCl were added and incubated on ice for 1hr to precipitate the phagemids. Precipitated phagemids were centrifuged at 8000 rpm for 20 min at 4° C. and carefully resuspended with 100 ml of cold PBS. The phagemid solution was further purified by centrifuging away the remaining cells with 8000 rpm for 10 min at 4° C. and precipitating the phagemids by adding 0.2 volume of 20% PEG/2.5M NaCl. The phagemids were centrifuged at 8000 rpm for 20 min at 4° C., and the phagemid pellets were resuspended with 12 ml of cold PBS. Four milliliter of 60% glycerol solution was added to the phagemid solution for storage at −80° C. The phagemid titers were determined by a standard procedure (Molecular Cloning, Maniatis et al $3^{rd}$ Edition).

3. Selection of Human MPL Binding Phages

A. Biotinylation of Human MPL

One milligram of recombinant human MPL was biotinylated using the EZ-Link Sulfo-NHS-LC-Biotinylation Kit (PIERCE, Rockford, Ill.) according to the manufacturer's directions.

B. Immobilization of MPL on Magnetic Beads

The biotinylated MPL (section 3A) was immobilized on the Dynabead M-280 Streptavidin (DYNAL, Lake Success, N.Y.) at a concentration of 1 µg MPL per 100 µl of the bead stock from the manufacturer. After drawing the beads to one side of a tube using a magnet and pipetting away the liquid, the beads were washed twice with the phosphate buffer saline (PBS) and resuspended in PBS. The biotinylated MPL protein was added to the washed beads at the above concentration and incubated with rotation for 1 hour at room temperature. The MPL coated beads were then blocked by adding BSA to 2% final concentration and incubating overnight at 4° C. with rotation. The resulting MPL coated beads were then washed twice with PBST (PBS with 0.05% Tween-20) before being subjected to the selection procedures.

C. Selection Using the MPL Coated Beads

About 100 fold library equivalent phagemids (section 2C, $1 \times 10^{11}$ cfu for fixed library, $2.4 \times 10^{11}$ cfu for doped library) were blocked for one hour with 1 ml of PBS containing 2% BSA. The blocked phagemid sample was subjected to a negative selection step by adding it to blank beads (same beads as section 3B but no MPL coated), and this mixture was incubated at room temperature for 1 hr with rotation. The phagemid containing supernatant was drawn out using magnet and transferred to a new tube containing MPL coated beads (section 3B), and this mixture was incubated at room temperature for 1 hr with rotation. After the supernatant was discarded, the phagemid-bound-beads were washed 10 times with PBST and 10 times with PBS. The phagemids were then allowed to elute in 1 ml of 100 mM triethylamine solution (Sigma, St. Louis, Mo.) for 10 minutes on a rotator. The pH of the phagemid containing solution was neutralized by adding 0.5 ml of 1 M Tris-HCl (pH 7.5). The resulting phagemids were used to infect 5 ml of freshly grown TG1 bacteria ($OD_{600}$ about 0.5) at 37° C. for 30 minutes without shaking and 30 minutes with slow shaking. All the infected TG1 cells were plated on a large 2×YTAG plate and incubated at 30° C. overnight.

D. Induction and Harvesting of Phage

A 10 ml aliquot of 2×YTAG media was added to the plate (section 3C) to resuspend TG1 cells. All TG1 cells were collected in a tube, and a 250 µl aliquot of these cells was added to 25 ml of 2×YTAG and grown at 37° C. until $OD_{600}$=0.5. The M13KO7 helper phages were added to a final concentration of $3 \times 10^9$ cfu/ml and incubated at 37° C. for 30 minutes without shaking and 30 minutes with slow shaking. The cells were centrifuged with 5000 rpm for 10 minute at 4° C. and resuspended with 25 ml of 2×YTAK. These bacteria were allowed to grow at 30° C. overnight with shaking. The induced phagemids were harvest and purified as in section 2C.

E. Second Round Selection

The second round selection was performed as outlined in section 3B to 3C except the following. About 0.5 ml aliquot of phagemid solution resulting from section 3D was used as the input phagemid. Only 0.1 µg of biotinylated MPL (section 3A) was used to coat onto the Dynabead M-280 Streptavidin. The phage-bound-beads were washed 16 times with PBST, where the final wash involved 30 minutes incubation at room temperature in PBST. The beads were washed 10 more times with PBS.

4. Clonal Analysis

A. Preparation of Master Plate

Single colonies from the second round selection were picked and inoculated into 96 well plates containing 120 µl of 2×YTAG per well. The 96 well plates were incubated in 30° C. shaker for overnight. Forty microliters of 60% glycerol were added per well for storage at −80° C.

B. Phagemid ELISA

About 3 µl aliquots of cells from the master plate (section 4A) were inoculated into a fresh 96 well plate with containing 120 µl of 2×YTAG per well, and this new plate of cells were grown at 37° C. until approximate $OD_{600}$=0.5. Forty microliters of 2×YTAG containing M13KO7 helper phage ($1.2 \times 10^{10}$ cfu/ml) were added to each well, and the 96 well plate was incubated at 37° C. for 30 minutes without shaking and another 30 min with slow shaking. The plate was centrifuged at 2000 rpm (Beckman CS-6R tabletop centrifuge) for 10 min at 4° C. The supernatants were removed from the wells, and each cell pellet was resuspended using 160 µl of 2×YTAK per well. The plate was incubated at 30° C. overnight for phagemid expression.

Recombinant human MPL was coated onto the 96 well Maxisorp plate (NUNC) at 5 µg/ml in 0.1 M carbonate buffer pH9.6 at 4° C. overnight. As a control, BSA (Sigma) was coated onto a separate Maxisorp plate at 5 ug/ml.

On the following day, the overnight cell cultures were centrifuged at 2000 rpm for 10 min at 4° C. Twenty microliters of supernatant from each well were transferred to a new 96 well plate containing 180 µl of 2% BSA/PBS solution per well. The resulting mixtures were incubated for 1 hour at room temperature with shaking to block the phagemids. Meanwhile, the MPL coated plate was blocked with 200 µl of 2% BSA/PBS solution per well for 1 hour at room temperature while shaking. The BSA solution was discarded, and each well was washed three times with PBST solution. After the last washing step, 50 µl of blocked phagemid solutions was added to each well of the MPL coated plate as well as the control plate and incubated for 1 hour at room temperature with shaking. The liquid was discarded, and each well was washed three times with PBST solution. Fifty microliters of the HRP-conjugated anti-M13 mAb (Amersham Pharmacia Biotech) at 1:15,000 dilution were added to each well of the MPL coated and control plates, and these plates were incubated for 1 hour at room temperature with shaking. The liquids were discarded again, and each well was washed three times with PBST solution. Fifty microliters of LumiGLO chemiluminescent substrates (Kirkegaard & Perry Laboratories, Gaithersburg, Md.) were added to the wells, and each well was read by Luminoskan Ascent DLRearly machine (Labsystems, Franklin, Mass.).

C. Sequencing of the Phage Clones

PCR reaction was performed using 1 µl of bacteria from each well of the master plate (section 4A) as a template. The volume of each PCR mixture was 20 µl which contains 1×PCR buffer, 300 nM of each of the two primers 5'-GTAGCTCACTCATTAGGCAC-3' and 5'-GTACCGTAA-CACTGAGTTTCG-3', 200 nM dNTP, 2 mM $CaCl_2$, and 5 U taq DNA polymerase (Roche Molecular Biochemicals). The GeneAmp PCR System 9700 (Applied Biosystem) was used to run the following program: 94° C. for 5 min; 40 cycles of [94° C. for 45 second, 55° C. for 45 second, 72° C. for 90 second]; 72° C. for 10 min; cool to 4° C. The PCR products were purified with QIAquick 96 PCR Purification Kit (QIAGEN Inc.) according to the manufacturer's directions. All purified PCR products were sequenced with primer 5'-CGGATAACAATTTCACACAGG-3' using the ABI 3770 Sequencer (Perkin Elmer) according to the manufacturer's directions.

5. Sequence Ranking

The peptide sequences that were translated from nucleotide sequences above were correlated to ELISA data. The clones that showed high OD reading in the MPL coated wells and low OD reading in the BSA coated wells were considered as candidates for further study. The sequences that occur multiple times were also considered as candidates for further study. The phage clones selected based on these criteria were further characterized in ELISA titration experiments. See FIG. 9 (ELISA dose-response of selected phage clones).

Example 2

Preparation of Peptides

All peptides were prepared by the well-established stepwise solid phase synthesis method. Merrifield (1963), J. Am. Chem. Soc. 85:2149. Steward and Young (1969), Solid Phase Peptide Synthesis. Fmoc-protected amino acids were used as the building blocks and the peptide-chain was built-up using an ABI or Symphony peptide synthesizer. Typically, peptide synthesis began with a preloaded Wang resin to generate a peptide with a free carboxylic acid at the C-terminus (alternatively, Rink resin can be used to generate a peptide with a C-terminal amide functionality). Fmoc removal was carried out with the standard piperidine protocol. The coupling was effected using uronium (such as HBTU) or carbodiimide (such as DCC/HOBt) chemistry. Side-chain protecting groups were: Glu(O-t-Bu), Asp(O-t-Bu), Ser(t-Bu), Thr(t-Bu), Arg(Pbf), Asn(Trt), Gln(Trt), His (Trt), Lys(t-Boc), Trp(t-Boc) and Cys(Trt). The final deprotection and cleavage of all peptidyl-resins was effected at RT for 4 hr, using trifluoroacetic acid (TFA) containing 2.5% $H_2O$, 5% phenol, 2.5% triisopropylsilane and 2.5% thioanisole or mercaptoethanol. After removal of TFA, the cleaved peptide was precipitated with cold anhydrous ether. For those peptides that contain disulfide bonds, formation of the cyclic products was performed directly on the crude material by using 15% DMSO in $H_2O$ (pH 7.5). All crude peptides were purified by reverse phase HPLC and the structures of purified peptides were confirmed by ESI-MS and amino acid analysis.

Example 3

Preparation of TMP-Fc Peptibody Compounds

Several peptides were chosen for expression as peptide-Fc fusions (i.e., Fc attached to the C-terminus of the peptide) (C-terminal fusions). A DNA sequence coding for the Fc region of human IgG1 fused in-frame to each TPO-mimetic peptide was placed under control of the luxPR promoter in the plasmid expression vector pAMG21 as follows.

The plasmid encoding TMP1-Fc (Amgen strain #3788) was altered to contain an ApaLI site and a XhoI site to allow for easy cloning of short peptides from annealed oligonucleotides. The primer 2396-69 was used to add the ApaLI and XhoI restriction enzyme sites. PCR was performed with Expand Long polymerase using 2396-69 and the universal 3' primer 191-24 on the 3788 DNA template. The primer sequences are as follows:

```
2396-69   ACAAACAAACATATGGGTGCACAGAAAGCGGCCGCAAAAAAA
          CTCGAGGGTGGAGGCGGTGGGGACA 191-24    GGTCATTACTGGACCGGATC
```

The resulting PCR fragment was digested with NdeI and BsrGI, gel purified, and used as the insert. The plasmid from strain #3788 was also digested NdeI and BsrGI, gel purified, and used as the vector. Vector and insert were ligated together, and the resulting ligation mixture was electroporated into GM221 cells (see below). Single colonies were picked and plasmid DNA was prepared and DNA sequenced. One resulting plasmid, 200003180, was shown to have the correct DNA sequence and was used as the vector for constructing TMP-Fc fusions. This vector is shown in FIG. 6.

Plasmid 200003180 was digested with ApaLI and XhoI and served as the vector. Each pair of oligonucleotides (see FIG. 7) was annealed to form a duplex with ApaLI and XhoI sticky ends. These molecules were ligated into the vector to produce the fusion proteins of interest. The ApaLI to XhoI fragment for each corresponding pair of oligonucleotides is provided in FIG. 7.

TMPs 1-23, 25, 26 and 28 were expressed as C-terminal fusions.

Example 4

Preparation of FC-TMP Peptibody Compounds

Some of the peptides were expressed as Fc-peptide fusions (i.e., Fc attached to the N-terminus of peptide)(N-terminal fusions). The plasmid encoding Fc-TMP1 (Amgen strain #3728) was altered to contain an ApaLI site and an XhoI site to allow for easy cloning of short peptides from annealed oligonucleotides. A primer, 2396-70, was designed to add the ApaLI and XhoI restriction enzyme sites. PCR was performed with Expand Long polymerase using 2396-70 and the universal 5' primer 1209-85 on the 3728 DNA template. The primer sequences are as follows:

```
1209-85        CGTACAGGTTTACGCAAGAAAATGG 2396-70        TTTGTTGGATCCATTACTCGAGTTTTTTTGCGGCC
               GCTTTCTGTGCACCACCACCTCCACCTTTAC
```

The resulting PCR fragment was digested with BsrGI and BamHI, gel purified, and used as the insert. The plasmid from strain #3728 was also digested with BsrGI and BamHI, gel purified, and used as the vector. Vector and insert were ligated together, and the resulting ligation mixture was electroporated into GM221 cells. Single colonies were picked and plasmid DNA was prepared and DNA sequenced. One resulting plasmid, 200003182 (FIG. 8), was shown to have the correct DNA sequence and was used as the vector for constructing Fc-TMP fusions.

The 200003182 plasmid was digested with ApaLI and XhoI and served as the vector. Annealed oligos with ApaLI and XhoI sticky ends were ligated into the vector to produce the fusions of interest.

TMP20, TMP24, TMP27, TMP29 and TMP30 were produced as N-terminal fusions in this manner.

Transformation

Each of the above ligations were transformed by electroporation into the host strain GM221 described below. Clones were screened for the ability to produce the recombinant protein product and to possess the gene fusion having the correct nucleotide sequence.

pAMG21

The expression plasmid pAMG21 is available from the ATCC under accession number 98113, which was deposited on Jul. 24, 1996.

GM221 (Amgen Host Strain #2596)

The Amgen host strain #2596 is an E.coli K-12 strain that has been modified to contain both the temperature sensitive lambda repressor cI857s7 in the early ebg region and the lacI$^Q$ repressor in the late ebg region (68 minutes) The presence of these two repressor genes allows the use of this host with a variety of expression systems, however both of these repressors are irrelevant to the expression from LUXP$_R$. The untransformed host has no antibiotic resistances.

The ribosome binding site of the cI857s7 gene has been modified to include an enhanced RBS. It has been inserted into the ebg operon between nucleotide position 1170 and 1411 as numbered in Genbank accession number M64441Gb_Ba with deletion of the intervening ebg sequence.

The construct was delivered to the chromosome using a recombinant phage called MMebg-cI857s7 enhanced RBS #4 into F'tet/393. After recombination and resolution only the chromosomal insert described above remains in the cell. It was renamed F'tet/GM101.

F'tet/GM101 was then modified by the delivery of a lacI$^Q$ construct into the ebg operon between nucleotide position 2493 and 2937 as numbered in the Genbank accession number M64441Gb_Ba with the deletion of the intervening ebg sequence. The construct was delivered to the chromosome using a recombinant phage called AGebg-LacIQ#5 into F'tet/GM101. After recombination and resolution only the chromosomal insert described above remains in the cell. It was renamed F'tet/GM221. The F'tet episome was cured from the strain using acridine orange at a concentration of 25 ug/ml in LB. The cured strain was identified as tetracyline sensitive and was stored as GM221.

Expression

Cultures of GM221 expressing each of the fusion proteins were grown at 37° C. in Luria Broth medium. Induction of gene product expression from the luxPR promoter was achieved following the addition of the synthetic autoinducer N-(3-oxohexanoyl)-DL-homoserine lactone to the culture media to a final concentration of 20 ng/ml and incubation at 37° C. for a further 3 hours. After 3 hours, the bacterial cultures were examined by microscopy for the presence of inclusion bodies and were then collected by centrifugation. Refractile inclusion bodies were observed in induced cultures indicating that the fusion protein was most likely produced in the insoluble fraction in E. coli. Cell pellets were lysed directly by resuspension in Laemmli sample buffer containing 10% β-mercaptoethanol and were analyzed by SDS-PAGE. An intense Coomassie stained band of the appropriate size (approximately 30 kDa) was observed for each protein.

Example 5

Purification of Peptibody Compounds

Cells were broken in water (1/10) by high pressure homogenization (2 passes at 14,000 PSI) and inclusion bodies were harvested by centrifugation (4200 RPM in J-6B for 1 hour). Inclusion bodies were solubilized in 6 M guanidine, 50 mM Tris, 8 mM DTT, pH 8.7 for 1 hour at a 1/10 ratio. The solubilized mixture was diluted 20 times into 2 M urea, 50 mM Tris, 160 mM arginine, 3 mM cysteine, pH 8.5. The mixture was stirred overnight in the cold. The mixture was then concentrated about 10 fold by ultrafiltration. It was then diluted 3 fold with 10 mM Tris, 1.5 M urea, pH 9. The pH of this mixture was then adjusted to pH 5 with acetic acid. The precipitate was removed by centrifugation and the supernatant was loaded onto a SP-Sepharose Fast Flow column equilibrated in 20 mM NaAc, 100 mM NaCl, pH 5 (10 mg/ml protein load, room temperature). The protein was eluted using a 20 column volume gradient in the same buffer ranging from 100 mM NaCl to 500 mM NaCl. The pool from the column was diluted 3 fold and loaded onto a SP-Sepharose HP column in 20 mM NaAc, 150 mM NaCl, pH 5 (10 mg/ml protein load, room temperature). The protein was eluted using a 20 column volume gradient in the same buffer ranging from 150 mM NaCl to 400 mM NaCl. The peak was pooled and filtered.

Example 6

Peptide Affinity Binding Studies

Experment were carried out using BIACORE 3000 at room temperature to determine the binding affinity for several TMP peptides (TMP1-TMP23). Hu-mpl was immobilized on the sensor chip (CM5) surface using amine coupling procedure (activation by NHS/EDC and blocking by ethanolamine). 0.78 nM to 100 nM of TMP peptides were injected over the hu-mpl surface. BIACORE running buffer was PBS with 0.005% Surfactant P20. Samples were also injected over a blank surface for a control. The experimental data were analyzed using BIAEVALUATION 3.1 software package.

As previously discussed, to better mimic the phage environment from which the peptides were selected and to conceal from the receptor the charged amino- and carboxy-terminus ends of the 18 amino acid preferred peptides (TMP2-TMP30), two amino acid "caps" were added to each of the carboxy terminus and the amino terminus of each peptide: glutamine-cysteine (QC) to the amino terminus and histadine-serine (HS) to the carboxy terminus, bringing the length of each peptide to 22 amino acids. Since peptide affinity is known to increase with peptide lentgh, the benchmark bioactive 14 amino acid peptide sequence (SEQ ID NO 1) was also increased to a total of 22 amino acids. The bioactive region of each peptide, however, remains the same and is indicated in bold below.

| TMP No. | Peptide Sequence | K$_D$ (nM) | Affinity relative to TMP1 |
|---|---|---|---|
| TMP1 | SAQGIEGPTLRQWLAARALETV | 5.40 | — |
| TMP2 | QGGAREGPTLRQWLEWVRVGHS | 1.60 | 3.38 |
| TMP3 | QGRDLDGPTLRQWLPLPSVQHS | 45.00 | 0.12 |
| TMP4 | QGALRDGPTLKQWLEYRRQAHS | 0.86 | 6.28 |
| TMP5 | QGARQEGPTLKEWLFWVRMGHS | 6.66 | 0.81 |
| TMP6 | QGEALLGPTLREWLAWRRAQHS | 0.37 | 14.59 |
| TMP7 | QGMARDGPTLREWLRTYRMMHS | 1.20 | 4.50 |
| TMP8 | QGWMPEGPTLKQWLFHGRGQHS | 23.20 | 0.23 |
| TMP9 | QGHIREGPTLRQWLVALRMVHS | 1.67 | 3.23 |
| TMP10 | QGQLGHGPTLRQWLSWYRGMHS | 1.22 | 4.43 |
| TMP11 | QGELRQGPTLHEWLQHLASKHS | 35.90 | 0.15 |
| TMP12 | QGVGIEGPTLRQWLAQRLNPHS | 5.20 | 1.04 |
| TMP13 | QGWSRDGPTLREWLAWRAVGHS | 4.44 | 1.22 |
| TMP14 | QGAVPQGPTLKQWLLWRRCAHS | 0.88 | 6.14 |
| TMP15 | QGRIREGPTLKEWLAQRRGFHS | 1.03 | 5.24 |
| TMP16 | QGRFAEGPTLREWLEQRKLVHS | 6.58 | 0.82 |

-continued

| TMP No. | Peptide Sequence | $K_D$ (nM) | Affinity relative to TMP1 |
|---|---|---|---|
| TMP17 | QGDRFQGPTLREWLAAIRSVHS | 12.90 | 0.42 |
| TMP18 | QGAGREGPTLREWLNMRVWQHS | 12.80 | 0.42 |
| TMP19 | QGALQEGPTLRQWLGWGQWGHS | 78.50 | 0.07 |
| TMP20 | QGYCDEGPTLKQWLVCLGLQHS | 0.56 | 9.64 |
| TMP21 | QGWCKEGPTLREWLRWGFLCHS | 1.53 | 3.53 |
| TMP22 | QGCSSGGPTLREWLQCRRMQHS | <0.1 | >54 |
| TMP23 | QGCSWGGPTLKQWLQCVRAKHS | <0.1 | >54 |

Example 7

Peptide Bioactivity Studies

Cell-based assays were used to determine the bioactivity of the peptides TMP1-TMP23.

The murine 32D cell proliferation assay involves the use of murine 32D cells that have been transfected with a human mpl receptor. The results below are reported relative to TMP1.

The CD61 cell assay involves the use of primary human CD34+ cells, which were cultured for several days in the presence of peptides TMP1-TMP23. These cells were then sorted to determine the percentage of cells expressing a megakaryocyte specific marker (CD61) on the cell surface.

While active compounds stimulated the appearance of these platelet precursors cells in a dose-dependent fashion, markers for erythroid precursors (CD36+) and neutrophil precursors (CD15+) remained at baseline. Qualitative results of the CD61 cell assay, which represent the average of three different concentrations, are shown below.

| Peptide | Murine 32D Cell Proliferation Assay (relative to TMP1) | CD61 Cell Assay (relative to TMP1 |
|---|---|---|
| TMP01 | 100% | −/+ |
| TMP02 | 290% | + |
| TMP03 | 39% | ++ |
| TMP04 | 42% | − |
| TMP05 | 85% | ++ |
| TMP06 | 569% | ++ |
| TMP07 | 289% | ++ |
| TMP08 | 39% | + |
| TMP09 | 2% | − |
| TMP10 | 12% | − |
| TMP11 | 21% | − |
| TMP12 | 10% | − |
| TMP13 | 328% | ++ |
| TMP14 | 635% | +++ |
| TMP15 | 35% | − |
| TMP16 | 32% | + |
| TMP17 | 21% | − |
| TMP18 | 337% | ++ |
| TMP19 | 27% | + |
| TMP20 | Not Detectable | −/+ |
| TMP21 | 312% | −/+ |
| TMP22 | Not Detectable | − |
| TMP23 | Not Detectable | +++ |

Example 8

Peptibody Binding Studies

Several TMP peptibodies were tested for their binding activities to hu-MPL in a direct binding analysis on BIAcore. The experiments were carried out using BIAcore 2000 (BIACORE Inc.) at 25C. The running buffer was PBS with 0.005% Surfactant P20. Recombinant Protein G (Pierce 21193ZZ) was immobilized onto a CM5 chip following a standard amine coupling procedure (activation by NHS/EDC and blocking by ethanolamine) to capture the TMP peptibodies to approximate 400 RU. Recombinant hu-MPL (Lot 27315-53) was serially diluted from 1 uM to 0.15 nM in sample buffer (PBS with 0.005% Surfactant P20 and 100 ug/ml BSA) before injection over the captured peptibody surfaces at 50 ul/min for 3 minutes. rhu-MPL samples were also injected over a blank protein G surface to subtract any non-specific binding background. The protein G surface was regenerated with sequential injection of 100 ul of ImmunoPure IgG elution buffer (Pierce 21009ZZ, pH 2) and 100 ul of 8 mM Glycine pH 1.5, 1 M NaCl at 50 ul/min between two cycles. Binding affinities ($K_D$) of the peptibodies to rhu-MPL were determined by nonlinear regression analysis of the data using BIAevaluation 3.1 (BIACORE Inc.). The results are summarized as follows:

| Peptibody (TMP-Fc) | $k_a$ (1/Ms) | $k_d$ (1/s) | $K_D$ (M) |
|---|---|---|---|
| TMP20-Fc | $5.06 \times 10^4$ | $7.34 \times 10^{-3}$ | $1.45 \times 10^{-7}$ |
| Fc-TMP24 | $4.01 \times 10^4$ | $8.75 \times 10^{-3}$ | $2.18 \times 10^{-7}$ |
| TMP25-Fc | $2.35 \times 10^4$ | $1.40 \times 10^{-3}$ | $5.97 \times 10^{-8}$ |
| TMP26-Fc | $2.58 \times 10^4$ | $5.72 \times 10^{-3}$ | $2.22 \times 10^{-7}$ |
| Fc-TMP27 | $1.3 \times 10^5$ | $8.42 \times 10^{-3}$ | $6.49 \times 10^{-8}$ |
| TMP28-Fc | $6.78 \times 10^4$ | $2.52 \times 10^{-2}$ | $3.71 \times 10^{-7}$ |

Example 9

Peptibody Activity Assays

Figure 10:
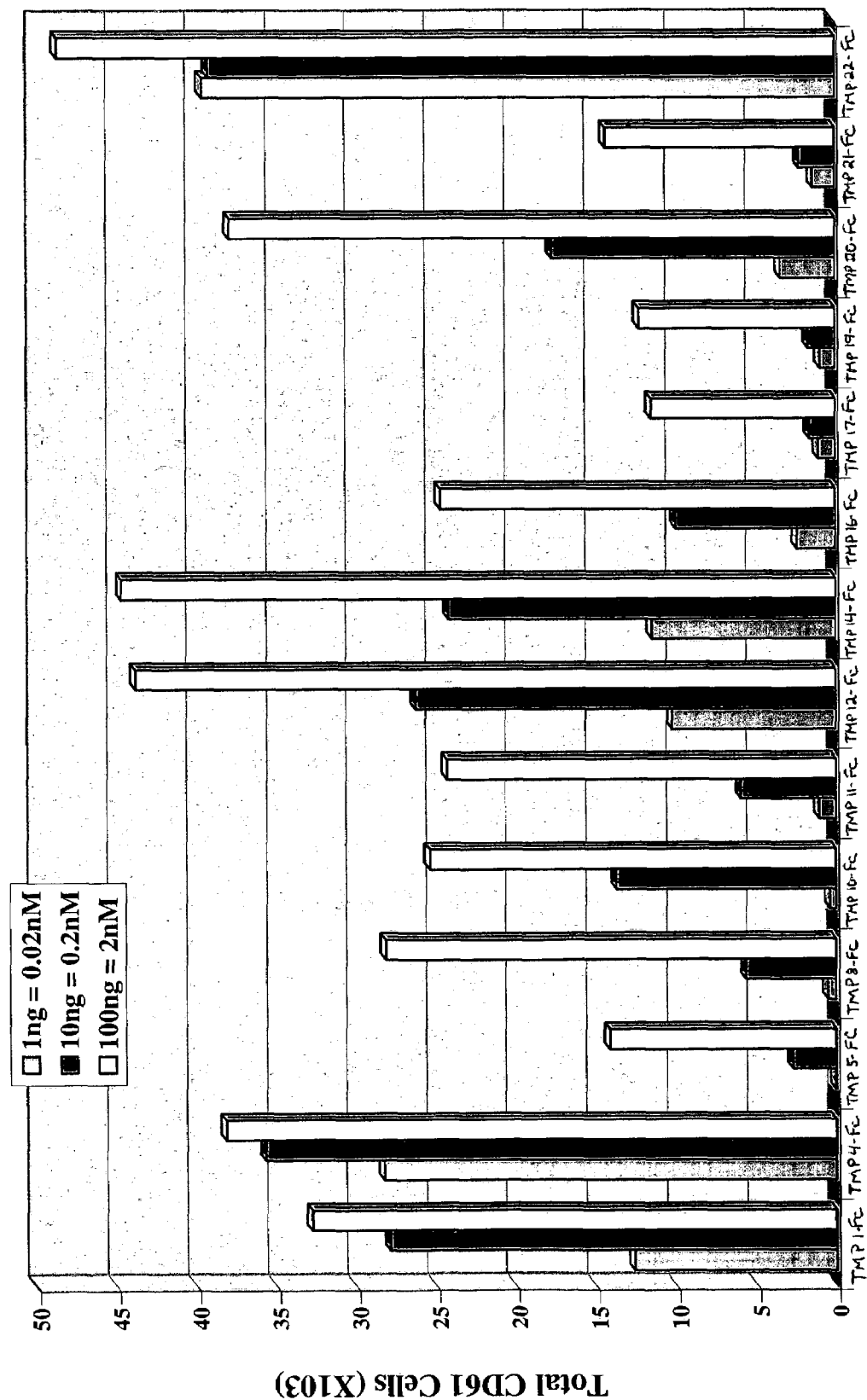
FIGS. 10, 11 and 12 show the bioactivity of select compounds of the present invention.
Figure 11:
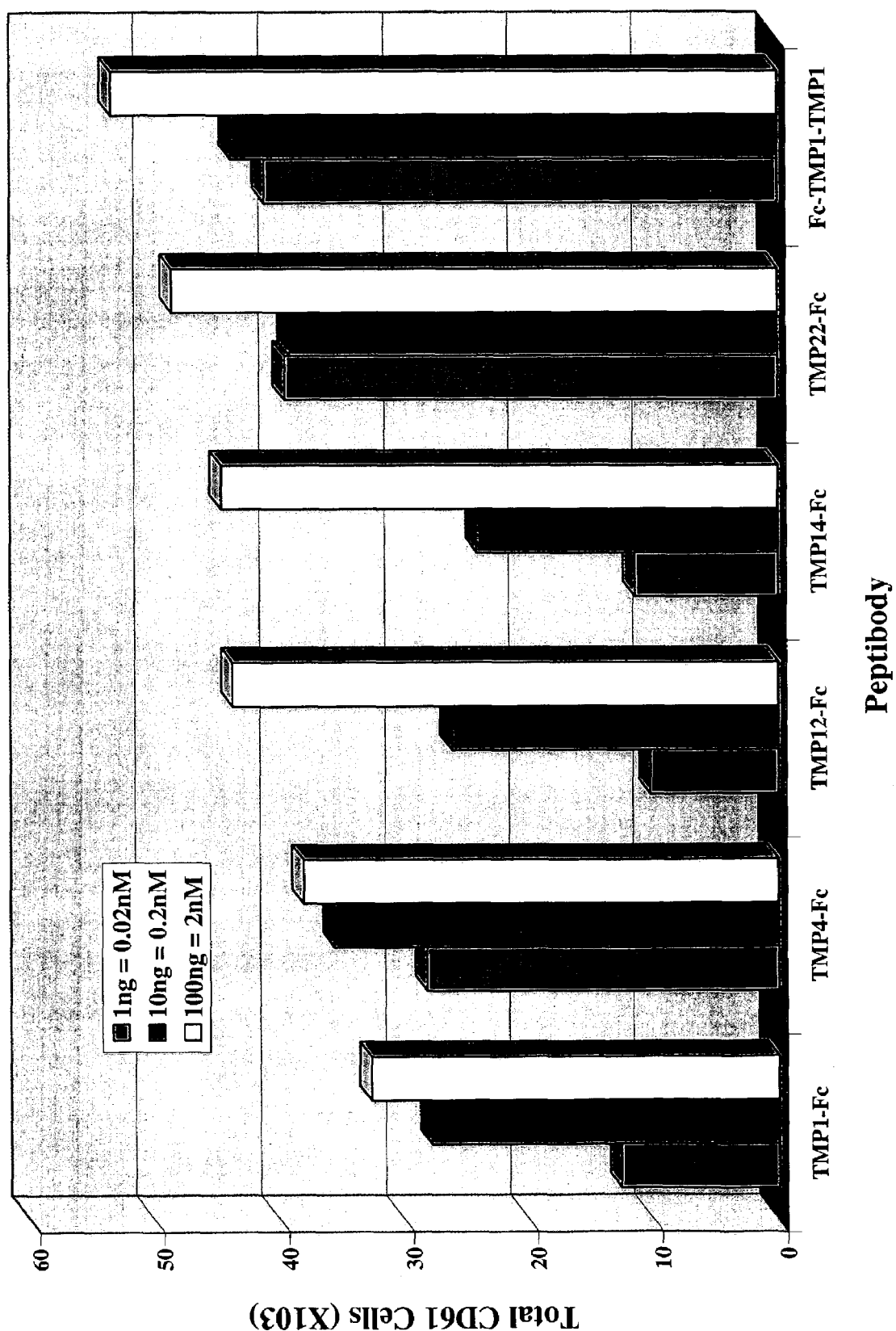
Figure 12:
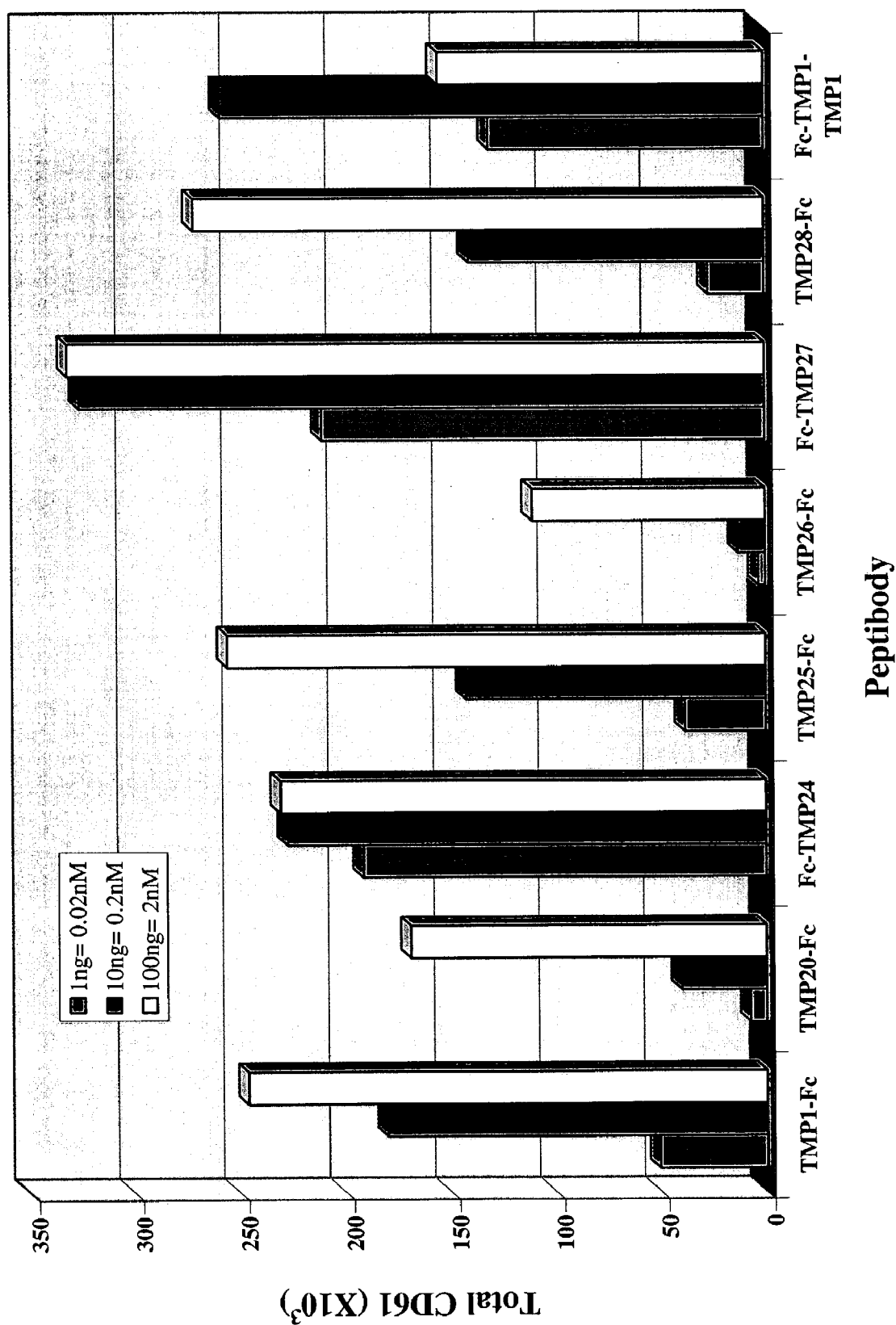

Primary human CD34+ cells were cultured for several days in the presence of several TMP-Fc fusion proteins. These cells were then sorted to determine the percentage of cells expressing a megakaryocyte specific marker (CD61) on the cell surface. While active compounds stimulated the appearance of these platelet precursor cells in a dose-dependent fashion, markers for erythroid precursors (CD36+)(not shown) and neutrophil precursors (CD15+)(not shown) remained at baseline. See FIGS. 10, 11 and 12 (CD61 cell assay).

Example 10

In Vivo Activity

Normal female BDF1 mice, approximately 10-12 weeks of age, were used for in vivo activity studies.

Mice were injected subcutaneously for a bolus treatment. Subcutaneous injections were delivered in a volume of 0.2 ml. Compounds were diluted in PBS with 0.1% BSA. All experiments included one control group, labeled "carrier" that were treated with this diluent only.

Figure 13:
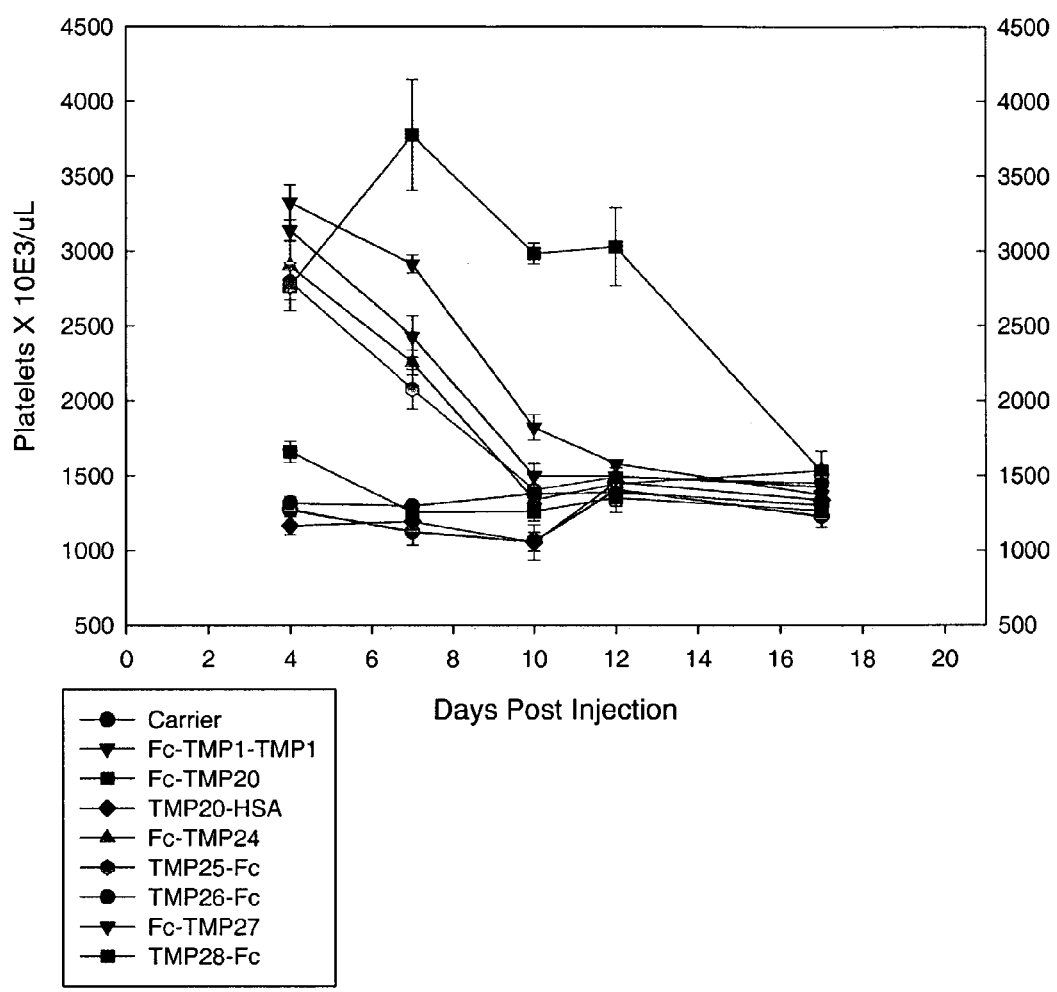

Ten mice per group treated on day 0, two groups started 4 days apart for a total of 20 mice per group. Five mice bled at each time point, mice were bled a minimum of three times a week. Mice were anesthetized with isoflurane and a total volume of 140-160 ul of blood was obtained by puncture of the orbital sinus. Blood was counted on a Technicon H1E blood analyzer running software for murine blood. Parameters measured were white blood cells, red blood cells, hematocrit, hemoglobin, platelets, neutrophils. See FIGS. 13 and 14.

The invention now being fully described, it will be apparent to one of ordinary skill in the art that many changes and modifications can be made thereto, without departing from the spirit and scope of the invention as set forth herein.

What is claimed is:

1. A compound that binds to an mpl receptor comprising a sequence which is selected from the group consisting of SEQ ID NO 2 to SEQ ID NO 30, inclusive

| PEPTIDE SEQUENCE | SEQ ID NO: |
|---|---|
| GAREGPTLRQWLEWVRVG | 2 |
| RDLDGPTLRQWLPLPSVQ | 3 |
| ALRDGPTLKQWLEYRRQA | 4 |
| ARQEGPTLKEWLFWVRMG | 5 |
| EALLGPTLREWLAWRRAQ | 6 |
| MARDGPTLREWLRTYRMM | 7 |
| WMPEGPTLKQWLFHGRGQ | 8 |
| HIREGPTLRQWLVALRMV | 9 |
| QLGHGPTLRQWLSWYRGM | 10 |
| ELRQGPTLHEWLQHLASK | 11 |
| VGIEGPTLRQWLAQRLNP | 12 |
| WSRDGPTLREWLAWRAVG | 13 |

-continued

| PEPTIDE SEQUENCE | SEQ ID NO: |
| --- | --- |
| AVPQGPTLKQWLLWRRCA | 14 |
| RIREGPTLKEWLAQRROF | 15 |
| RFAEGPTLREWLEQRKLV | 16 |
| DRFQGPTLREWLAAIRSV | 17 |
| AGREGPTLREWLNMRVWQ | 18 |
| ALQEGPTLRQWLGWGQWG | 19 |
| YCDEGPTLKQWLVCLGLQ | 20 |
| WCKEGPTLREWLRWGFLC | 21 |
| CSSGGPTLREWLQCRRMQ | 22 |
| CSWGGPTLKQWLQCVRAK | 23 |
| CQLGGPTLREWLACRLGA | 24 |
| CWEGGPTLKEWLQCLVER | 25 |

-continued

| PEPTIDE SEQUENCE | SEQ ID NO: |
| --- | --- |
| CRGGGPTLHQWLSCFRWQ | 26 |
| CRDGGPTLRQWLACLQQK | 27 |
| ELRSGPTLKEWLVWRLAQ | 28 |
| GCRSGPTLREWLACREVQ | 29 |
| TCEQGPTLRQWLLCRQGR | 30. |

2. The compound according to claim 1 which is cyclic.

3. The compound according to claim 1 wherein at least one of the amino acid residues has a D configuration.

4. The compound according to claim 1 wherein all of the amino acid residues have a D configuration.

5. A dimer or multimer of the compounds according to claim 1.

* * * * *

```
                           SEQUENCE LISTING

<160> NUMBER OF SEQ ID NOS: 199

<210> SEQ ID NO 1
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 1

Gln Gly Ile Glu Gly Pro Thr Leu Arg Gln Trp Leu Ala Ala Arg Ala
1               5                   10                  15

Leu Glu

<210> SEQ ID NO 2
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 2

Gly Ala Arg Glu Gly Pro Thr Leu Arg Gln Trp Leu Glu Trp Val Arg
1               5                   10                  15

Val Gly

<210> SEQ ID NO 3
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 3

Arg Asp Leu Asp Gly Pro Thr Leu Arg Gln Trp Leu Pro Leu Pro Ser
1               5                   10                  15

Val Gln

<210> SEQ ID NO 4
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 4

Ala Leu Arg Asp Gly Pro Thr Leu Lys Gln Trp Leu Glu Tyr Arg Arg
1               5                   10                  15

Gln Ala

<210> SEQ ID NO 5
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 5

Ala Arg Gln Glu Gly Pro Thr Leu Lys Glu Trp Leu Phe Trp Val Arg
```

```
1               5                   10                  15
Met Gly

<210> SEQ ID NO 6
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 6

Glu Ala Leu Leu Gly Pro Thr Leu Arg Glu Trp Leu Ala Trp Arg Arg
1               5                   10                  15

Ala Gln

<210> SEQ ID NO 7
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 7

Met Ala Arg Asp Gly Pro Thr Leu Arg Glu Trp Leu Arg Thr Tyr Arg
1               5                   10                  15

Met Met

<210> SEQ ID NO 8
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 8

Trp Met Pro Glu Gly Pro Thr Leu Lys Gln Trp Leu Phe His Gly Arg
1               5                   10                  15

Gly Gln

<210> SEQ ID NO 9
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 9

His Ile Arg Glu Gly Pro Thr Leu Arg Gln Trp Leu Val Ala Leu Arg
1               5                   10                  15

Met Val

<210> SEQ ID NO 10
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 10

Gln Leu Gly His Gly Pro Thr Leu Arg Gln Trp Leu Ser Trp Tyr Arg
1               5                   10                  15

Gly Met
```

-continued

```
<210> SEQ ID NO 11
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 11

Glu Leu Arg Gln Gly Pro Thr Leu His Glu Trp Leu Gln His Leu Ala
1               5                   10                  15

Ser Lys

<210> SEQ ID NO 12
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 12

Val Gly Ile Glu Gly Pro Thr Leu Arg Gln Trp Leu Ala Gln Arg Leu
1               5                   10                  15

Asn Pro

<210> SEQ ID NO 13
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 13

Trp Ser Arg Asp Gly Pro Thr Leu Arg Glu Trp Leu Ala Trp Arg Ala
1               5                   10                  15

Val Gly

<210> SEQ ID NO 14
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 14

Ala Val Pro Gln Gly Pro Thr Leu Lys Gln Trp Leu Leu Trp Arg Arg
1               5                   10                  15

Cys Ala

<210> SEQ ID NO 15
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 15

Arg Ile Arg Glu Gly Pro Thr Leu Lys Glu Trp Leu Ala Gln Arg Arg
1               5                   10                  15

Gly Phe

<210> SEQ ID NO 16
<211> LENGTH: 18
<212> TYPE: PRT
```

-continued

<213> ORGANISM: Artificial Sequence
<220> FEATURE:
<223> OTHER INFORMATION: Synthesized Peptide Sequence

<400> SEQUENCE: 16

Arg Phe Ala Glu Gly Pro Thr Leu Arg Glu Trp Leu Glu Gln Arg Lys
1               5                   10                  15

Leu Val

<210> SEQ ID NO 17
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 17

Asp Arg Phe Gln Gly Pro Thr Leu Arg Glu Trp Leu Ala Ala Ile Arg
1               5                   10                  15

Ser Val

<210> SEQ ID NO 18
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 18

Ala Gly Arg Glu Gly Pro Thr Leu Arg Glu Trp Leu Asn Met Arg Val
1               5                   10                  15

Trp Gln

<210> SEQ ID NO 19
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 19

Ala Leu Gln Glu Gly Pro Thr Leu Arg Gln Trp Leu Gly Trp Gly Gln
1               5                   10                  15

Trp Gly

<210> SEQ ID NO 20
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 20

Tyr Cys Asp Glu Gly Pro Thr Leu Lys Gln Trp Leu Val Cys Leu Gly
1               5                   10                  15

Leu Gln

<210> SEQ ID NO 21
<211> LENGTH: 18
<212> TYPE: PRT
<213> ORGANISM: Artificial Sequence
<220> FEATURE:
<223> OTHER INFORMATION: Synthesized Peptide Sequence -continued

```
<400> SEQUENCE: 21

Trp Cys Lys Glu Gly Pro Thr Leu Arg Glu Trp Leu Arg Trp Gly Phe
1               5                   10                  15

Leu Cys

<210> SEQ ID NO 22
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 22

Cys Ser Ser Gly Gly Pro Thr Leu Arg Glu Trp Leu Gln Cys Arg Arg
1               5                   10                  15

Met Gln

<210> SEQ ID NO 23
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 23

Cys Ser Trp Gly Gly Pro Thr Leu Lys Gln Trp Leu Gln Cys Val Arg
1               5                   10                  15

Ala Lys

<210> SEQ ID NO 24
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 24

Cys Gln Leu Gly Gly Pro Thr Leu Arg Glu Trp Leu Ala Cys Arg Leu
1               5                   10                  15

Gly Ala

<210> SEQ ID NO 25
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 25

Cys Trp Glu Gly Gly Pro Thr Leu Lys Glu Trp Leu Gln Cys Leu Val
1               5                   10                  15

Glu Arg

<210> SEQ ID NO 26
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 26

Cys Arg Gly Gly Gly Pro Thr Leu His Gln Trp Leu Ser Cys Phe Arg
1               5                   10                  15
```

<210> SEQ ID NO 27
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 27

```
Cys Arg Asp Gly Gly Pro Thr Leu Arg Gln Trp Leu Ala Cys Leu Gln
1               5                   10                  15

Gln Lys
```

<210> SEQ ID NO 28
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 28

```
Glu Leu Arg Ser Gly Pro Thr Leu Lys Glu Trp Leu Val Trp Arg Leu
1               5                   10                  15

Ala Gln
```

<210> SEQ ID NO 29
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 29

```
Gly Cys Arg Ser Gly Pro Thr Leu Arg Glu Trp Leu Ala Cys Arg Glu
1               5                   10                  15

Val Gln
```

<210> SEQ ID NO 30
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 30

```
Thr Cys Glu Gln Gly Pro Thr Leu Arg Gln Trp Leu Leu Cys Arg Gln
1               5                   10                  15

Gly Arg
```

<210> SEQ ID NO 31
<211> LENGTH: 684
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (1)..(684)
<223> OTHER INFORMATION:

<400> SEQUENCE: 31

```
atg gac aaa act cac aca tgt cca cct tgt cca gct ccg gaa ctc ctg       48
Met Asp Lys Thr His Thr Cys Pro Pro Cys Pro Ala Pro Glu Leu Leu
```

```
ggg gga ccg tca gtc ttc ctc ttc ccc cca aaa ccc aag gac acc ctc      96
Gly Gly Pro Ser Val Phe Leu Phe Pro Pro Lys Pro Lys Asp Thr Leu
             20                  25                  30 atg atc tcc cgg acc cct gag gtc aca tgc gtg gtg gtg gac gtg agc     144
Met Ile Ser Arg Thr Pro Glu Val Thr Cys Val Val Val Asp Val Ser
         35                  40                  45 cac gaa gac cct gag gtc aag ttc aac tgg tac gtg gac ggc gtg gag     192
His Glu Asp Pro Glu Val Lys Phe Asn Trp Tyr Val Asp Gly Val Glu
     50                  55                  60 gtg cat aat gcc aag aca aag ccg cgg gag gag cag tac aac agc acg     240
Val His Asn Ala Lys Thr Lys Pro Arg Glu Glu Gln Tyr Asn Ser Thr
 65                  70                  75                  80 tac cgt gtg gtc agc gtc ctc acc gtc ctg cac cag gac tgg ctg aat     288
Tyr Arg Val Val Ser Val Leu Thr Val Leu His Gln Asp Trp Leu Asn
                 85                  90                  95 ggc aag gag tac aag tgc aag gtc tcc aac aaa gcc ctc cca gcc ccc     336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gaa cca cag     384
Ile Glu Lys Thr Ile Ser Lys Ala Lys Gly Gln Pro Arg Glu Pro Gln
        115                 120                 125 gtg tac acc ctg ccc cca tcc cgg gat gag ctg acc aag aac cag gtc     432
Val Tyr Thr Leu Pro Pro Ser Arg Asp Glu Leu Thr Lys Asn Gln Val
    130                 135                 140 agc ctg acc tgc ctg gtc aaa ggc ttc tat ccc agc gac atc gcc gtg     480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct     528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc     576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg     624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg     672
Met His Glu Ala Leu His Asn His Tyr Thr Gln Lys Ser Leu Ser Leu
    210                 215                 220 tct ccg ggt aaa                                                     684
Ser Pro Gly Lys
225

<210> SEQ ID NO 32
<211> LENGTH: 228
<212> TYPE: PRT
<213> ORGANISM: Artificial Sequence
<220> FEATURE:
<223> OTHER INFORMATION: Synthesized Peptide Sequence

<400> SEQUENCE: 32

Met Asp Lys Thr His Thr Cys Pro Pro Cys Pro Ala Pro Glu Leu Leu
  1               5                  10                  15

Gly Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Lys Phe Asn Trp Tyr Val Asp Gly Val Glu
     50                  55                  60
```

```
Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 33
<211> LENGTH: 835
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (60)..(791)
<223> OTHER INFORMATION:

<400> SEQUENCE: 33
tagtcgatta atcgatttga ttctagattt gttttaacta attaaaggag gaataacat     59 atg ggt gca cag aaa gcg gcc gca aaa aaa ctc gag ggt gga ggc ggt    107
Met Gly Ala Gln Lys Ala Ala Ala Lys Lys Leu Glu Gly Gly Gly Gly
1               5                  10                  15 ggg gac aaa act cac aca tgt cca cct tgc cca gca cct gaa ctc ctg    155
Gly Asp Lys Thr His Thr Cys Pro Pro Cys Pro Ala Pro Glu Leu Leu
            20                  25                  30 ggg gga ccg tca gtt ttc ctc ttc ccc cca aaa ccc aag gac acc ctc    203
Gly Gly Pro Ser Val Phe Leu Phe Pro Pro Lys Pro Lys Asp Thr Leu
        35                  40                  45 atg atc tcc cgg acc cct gag gtc aca tgc gtg gtg gtg gac gtg agc    251
Met Ile Ser Arg Thr Pro Glu Val Thr Cys Val Val Val Asp Val Ser
    50                  55                  60 cac gaa gac cct gag gtc aag ttc aac tgg tac gtg gac ggc gtg gag    299
His Glu Asp Pro Glu Val Lys Phe Asn Trp Tyr Val Asp Gly Val Glu
65                  70                  75                  80 gtg cat aat gcc aag aca aag ccg cgg gag gag cag tac aac agc acg    347
Val His Asn Ala Lys Thr Lys Pro Arg Glu Glu Gln Tyr Asn Ser Thr
                85                  90                  95 tac cgt gtg gtc agc gtc ctc acc gtc ctg cac cag gac tgg ctg aat    395
Tyr Arg Val Val Ser Val Leu Thr Val Leu His Gln Asp Trp Leu Asn
            100                 105                 110 ggc aag gag tac aag tgc aag gtc tcc aac aaa gcc ctc cca gcc ccc    443
```

-continued

```
Gly Lys Glu Tyr Lys Cys Lys Val Ser Asn Lys Ala Leu Pro Ala Pro
            115                 120                 125 atc gag aaa acc atc tcc aaa gcc aaa ggg cag ccc cga gaa cca cag        491
Ile Glu Lys Thr Ile Ser Lys Ala Lys Gly Gln Pro Arg Glu Pro Gln
130                 135                 140 gtg tac acc ctg ccc cca tcc cgg gat gag ctg acc aag aac cag gtc        539
Val Tyr Thr Leu Pro Pro Ser Arg Asp Glu Leu Thr Lys Asn Gln Val
145                 150                 155                 160 agc ctg acc tgc ctg gtc aaa ggc ttc tat ccc agc gac atc gcc gtg        587
Ser Leu Thr Cys Leu Val Lys Gly Phe Tyr Pro Ser Asp Ile Ala Val
                165                 170                 175 gag tgg gag agc aat ggg cag ccg gag aac aac tac aag acc acg cct        635
Glu Trp Glu Ser Asn Gly Gln Pro Glu Asn Asn Tyr Lys Thr Thr Pro
            180                 185                 190 ccc gtg ctg gac tcc gac ggc tcc ttc ttc ctc tac agc aag ctc acc        683
Pro Val Leu Asp Ser Asp Gly Ser Phe Phe Leu Tyr Ser Lys Leu Thr
        195                 200                 205 gtg gac aag agc agg tgg cag cag ggg aac gtc ttc tca tgc tcc gtg        731
Val Asp Lys Ser Arg Trp Gln Gln Gly Asn Val Phe Ser Cys Ser Val
    210                 215                 220 atg cat gag gct ctg cac aac cac tac acg cag aag agc ctc tcc ctg        779
Met His Glu Ala Leu His Asn His Tyr Thr Gln Lys Ser Leu Ser Leu
225                 230                 235                 240 tct ccg ggt aaa taatggatcc gcggaaagaa gaagaagaag aagaaagccc gaaa       835
Ser Pro Gly Lys
```

<210> SEQ ID NO 34
<211> LENGTH: 244
<212> TYPE: PRT
<213> ORGANISM: Artificial Sequence
<220> FEATURE:
<223> OTHER INFORMATION: Synthesized Peptide Sequence

<400> SEQUENCE: 34

```
Met Gly Ala Gln Lys Ala Ala Lys Lys Leu Glu Gly Gly Gly Gly
1               5                   10                  15

Gly Asp Lys Thr His Thr Cys Pro Pro Cys Pro Ala Pro Glu Leu Leu
            20                  25                  30

Gly Gly Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Lys Phe Asn Trp Tyr Val Asp Gly Val Glu
65                  70                  75                  80

Val His Asn Ala Lys Thr Lys Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Gly Gln Pro Arg Glu Pro Gln
    130                 135                 140

Val Tyr Thr Leu Pro Pro Ser Arg Asp Glu Leu Thr Lys Asn Gln Val
145                 150                 155                 160

Ser Leu Thr Cys Leu Val Lys Gly Phe Tyr Pro Ser Asp Ile Ala Val
                165                 170                 175

Glu Trp Glu Ser Asn Gly Gln Pro Glu Asn Asn Tyr Lys Thr Thr Pro
            180                 185                 190
```

```
Pro Val Leu Asp Ser Asp Gly Ser Phe Phe Leu Tyr Ser Lys Leu Thr
        195                 200                 205

Val Asp Lys Ser Arg Trp Gln Gln Gly Asn Val Phe Ser Cys Ser Val
    210                 215                 220

Met His Glu Ala Leu His Asn His Tyr Thr Gln Lys Ser Leu Ser Leu
225                 230                 235                 240

Ser Pro Gly Lys

<210> SEQ ID NO 35
<211> LENGTH: 66
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (4)..(66)
<223> OTHER INFORMATION:

<400> SEQUENCE: 35 cat atg ggt gca cag ggt atc gaa ggt ccg act ctg cgt cag tgg ctg      48
    Met Gly Ala Gln Gly Ile Glu Gly Pro Thr Leu Arg Gln Trp Leu
    1               5                   10                  15 gct gct cgt gct ctc gag                                              66
Ala Ala Arg Ala Leu Glu
            20

<210> SEQ ID NO 36
<211> LENGTH: 21
<212> TYPE: PRT
<213> ORGANISM: Artificial Sequence
<220> FEATURE:
<223> OTHER INFORMATION: Synthesized Peptide Sequence

<400> SEQUENCE: 36

Met Gly Ala Gln Gly Ile Glu Gly Pro Thr Leu Arg Gln Trp Leu Ala
1               5                   10                  15

Ala Arg Ala Leu Glu
            20

<210> SEQ ID NO 37
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 37

Thr Gly Cys Ala Cys Ala Ala Gly Gly Thr Gly Gly Ala Gly Cys Ala
1               5                   10                  15

Cys Gly Thr Gly Ala Ala Gly Gly Ala Cys Cys Ala Ala Cys Thr Cys
                20                  25                  30

Thr Thr Cys Gly Thr Cys Ala Ala Thr Gly Gly Cys Thr Thr Gly Ala
        35                  40                  45

Ala Thr Gly Gly Gly Thr Thr Cys Gly Thr Gly Thr Thr Gly Gly Thr
    50                  55                  60

Cys Ala Thr Thr Cys Thr Cys
65                  70

<210> SEQ ID NO 38
<211> LENGTH: 71
<212> TYPE: PRT
```

```
<213> ORGANISM: Artificial Sequence
<220> FEATURE:
<223> OTHER INFORMATION: Synthesized Peptide Sequence

<400> SEQUENCE: 38

Thr Cys Gly Ala Gly Ala Gly Ala Ala Thr Gly Ala Cys Cys Ala Ala
1               5                   10                  15

Cys Ala Cys Gly Ala Ala Cys Cys Ala Thr Thr Cys Ala Ala Gly
            20                  25                  30

Cys Cys Ala Thr Thr Gly Ala Cys Gly Ala Ala Gly Ala Gly Thr Thr
        35                  40                  45

Gly Gly Thr Cys Cys Thr Thr Cys Ala Cys Gly Thr Gly Cys Thr Cys
    50                  55                  60

Cys Ala Cys Cys Thr Thr Gly
65                  70

<210> SEQ ID NO 39
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 39 gt gca caa ggt gga gca cgt gaa gga cca act ctt cgt caa tgg ctt      47
   Ala Gln Gly Gly Ala Arg Glu Gly Pro Thr Leu Arg Gln Trp Leu
   1               5                   10                  15 gaa tgg gtt cgt gtt ggt cat tct ctc gag                              77
Glu Trp Val Arg Val Gly His Ser Leu Glu
                20                  25

<210> SEQ ID NO 40
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 40

Ala Gln Gly Gly Ala Arg Glu Gly Pro Thr Leu Arg Gln Trp Leu Glu
1               5                   10                  15

Trp Val Arg Val Gly His Ser Leu Glu
            20                  25

<210> SEQ ID NO 41
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 41

Thr Gly Cys Ala Cys Ala Ala Gly Gly Ala Cys Gly Thr Gly Ala Thr
1               5                   10                  15

Cys Thr Thr Gly Ala Thr Gly Gly Thr Cys Ala Ala Cys Thr Cys
            20                  25                  30

Thr Thr Cys Gly Thr Cys Ala Ala Thr Gly Gly Cys Thr Thr Cys Cys
        35                  40                  45

Ala Cys Thr Thr Cys Cys Ala Thr Cys Thr Gly Thr Thr Cys Ala Ala
```

```
                  50                  55                  60
Cys Ala Thr Thr Cys Thr Cys
 65                  70

<210> SEQ ID NO 42
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 42

Thr Cys Gly Ala Gly Ala Gly Ala Ala Thr Gly Thr Gly Ala Ala
 1               5                  10                  15

Cys Ala Gly Ala Thr Gly Gly Ala Ala Gly Thr Gly Ala Ala Gly
                20                  25                  30

Cys Cys Ala Thr Thr Gly Ala Cys Gly Ala Ala Gly Ala Gly Thr Thr
         35                  40                  45

Gly Gly Ala Cys Cys Ala Thr Cys Ala Ala Gly Ala Thr Cys Ala Cys
     50                  55                  60

Gly Thr Cys Cys Thr Thr Gly
 65                  70

<210> SEQ ID NO 43
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 43 gt gca caa gga cgt gat ctt gat ggt cca act ctt cgt caa tgg ctt      47
   Ala Gln Gly Arg Asp Leu Asp Gly Pro Thr Leu Arg Gln Trp Leu
    1               5                  10                  15 cca ctt cca tct gtt caa cat tct ctc gag                             77
Pro Leu Pro Ser Val Gln His Ser Leu Glu
                20                  25

<210> SEQ ID NO 44
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 44

Ala Gln Gly Arg Asp Leu Asp Gly Pro Thr Leu Arg Gln Trp Leu Pro
 1               5                  10                  15

Leu Pro Ser Val Gln His Ser Leu Glu
                20                  25

<210> SEQ ID NO 45
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 45

Thr Gly Cys Ala Cys Ala Ala Gly Gly Ala Gly Cys Thr Thr Thr Ala
```

```
                1               5                   10                  15
Cys Gly Thr Gly Ala Thr Gly Gly Thr Cys Cys Ala Ala Cys Thr Cys
                    20                  25                  30

Thr Thr Ala Ala Ala Cys Ala Ala Thr Gly Gly Thr Thr Ala Gly Ala
            35                  40                  45

Ala Thr Ala Thr Cys Gly Thr Cys Gly Thr Cys Ala Ala Gly Cys Thr
        50                  55                  60

Cys Ala Thr Thr Cys Ala Cys
65                  70

<210> SEQ ID NO 46
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 46

Thr Cys Gly Ala Gly Thr Gly Ala Ala Thr Gly Ala Gly Cys Thr Thr
1               5                   10                  15

Gly Ala Cys Gly Ala Cys Gly Ala Thr Ala Thr Cys Thr Ala Ala
                    20                  25                  30

Cys Cys Ala Thr Thr Gly Thr Thr Thr Ala Ala Gly Ala Gly Thr Thr
            35                  40                  45

Gly Gly Ala Cys Cys Ala Thr Cys Ala Cys Gly Thr Ala Ala Ala Gly
        50                  55                  60

Cys Thr Cys Cys Thr Thr Gly
65                  70

<210> SEQ ID NO 47
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 47 gt gca caa gga gct tta cgt gat ggt cca act ctt aaa caa tgg tta      47
   Ala Gln Gly Ala Leu Arg Asp Gly Pro Thr Leu Lys Gln Trp Leu
   1               5                   10                  15 gaa tat cgt cgt caa gct cat tca ctc gag                             77
Glu Tyr Arg Arg Gln Ala His Ser Leu Glu
                20                  25

<210> SEQ ID NO 48
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 48

Ala Gln Gly Ala Leu Arg Asp Gly Pro Thr Leu Lys Gln Trp Leu Glu
1               5                   10                  15

Tyr Arg Arg Gln Ala His Ser Leu Glu
            20                  25

<210> SEQ ID NO 49
```

<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 49

Thr Gly Cys Ala Cys Ala Ala Gly Gly Ala Gly Cys Ala Cys Gly Thr
1               5                   10                  15

Cys Ala Ala Gly Ala Ala Gly Gly Ala Cys Cys Ala Ala Cys Thr Cys
                20                  25                  30

Thr Thr Ala Ala Ala Gly Ala Ala Thr Gly Gly Thr Thr Ala Thr Thr
            35                  40                  45

Thr Thr Gly Gly Gly Thr Thr Cys Gly Thr Ala Thr Gly Gly Gly Thr
        50                  55                  60

Cys Ala Thr Thr Cys Ala Cys
65                  70

<210> SEQ ID NO 50
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 50

Thr Cys Gly Ala Gly Thr Gly Ala Ala Thr Gly Ala Cys Cys Cys Ala
1               5                   10                  15

Thr Ala Cys Gly Ala Ala Cys Cys Cys Ala Ala Ala Ala Thr Ala Ala
                20                  25                  30

Cys Cys Ala Thr Thr Cys Thr Thr Thr Ala Ala Gly Ala Gly Thr Thr
            35                  40                  45

Gly Gly Thr Cys Cys Thr Thr Cys Thr Thr Gly Ala Cys Gly Thr Gly
        50                  55                  60

Cys Thr Cys Cys Thr Thr Gly
65                  70

<210> SEQ ID NO 51
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 51 gt gca caa gga gca cgt caa gaa gga cca act ctt aaa gaa tgg tta      47
   Ala Gln Gly Ala Arg Gln Glu Gly Pro Thr Leu Lys Glu Trp Leu
   1               5                   10                  15 ttt tgg gtt cgt atg ggt cat tca ctc gag                             77
Phe Trp Val Arg Met Gly His Ser Leu Glu
            20                  25

<210> SEQ ID NO 52
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 52

-continued

```
Ala Gln Gly Ala Arg Gln Glu Gly Pro Thr Leu Lys Glu Trp Leu Phe
1               5                   10                  15

Trp Val Arg Met Gly His Ser Leu Glu
            20                  25

<210> SEQ ID NO 53
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 53

Thr Gly Cys Ala Cys Ala Ala Gly Gly Ala Gly Ala Ala Gly Cys Thr
1               5                   10                  15

Thr Thr Ala Thr Thr Ala Gly Gly Thr Cys Cys Ala Ala Cys Thr Thr
            20                  25                  30

Thr Ala Cys Gly Thr Gly Ala Ala Thr Gly Gly Cys Thr Thr Gly Cys
        35                  40                  45

Thr Thr Gly Gly Cys Gly Thr Cys Gly Thr Gly Cys Ala Cys Ala Ala
    50                  55                  60

Cys Ala Thr Thr Cys Thr Cys
65                  70

<210> SEQ ID NO 54
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 54

Thr Cys Gly Ala Gly Ala Gly Ala Ala Thr Gly Thr Thr Gly Thr Gly
1               5                   10                  15

Cys Ala Cys Gly Ala Cys Gly Cys Cys Ala Ala Gly Cys Ala Ala Gly
            20                  25                  30

Cys Cys Ala Thr Thr Cys Ala Cys Gly Thr Ala Ala Ala Gly Thr Thr
        35                  40                  45

Gly Gly Ala Cys Cys Thr Ala Ala Thr Ala Ala Ala Gly Cys Thr Thr
    50                  55                  60

Cys Thr Cys Cys Thr Thr Gly
65                  70

<210> SEQ ID NO 55
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 55 gt gca caa gga gaa gct tta tta ggt cca act tta cgt gaa tgg ctt     47
   Ala Gln Gly Glu Ala Leu Leu Gly Pro Thr Leu Arg Glu Trp Leu
   1               5                   10                  15 gct tgg cgt cgt gca caa cat tct ctc gag                            77
Ala Trp Arg Arg Ala Gln His Ser Leu Glu
                20                  25
```

<210> SEQ ID NO 56
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 56

Ala Gln Gly Glu Ala Leu Leu Gly Pro Thr Leu Arg Glu Trp Leu Ala
1               5                   10                  15

Trp Arg Arg Ala Gln His Ser Leu Glu
            20                  25

<210> SEQ ID NO 57
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 57

Thr Gly Cys Ala Cys Ala Ala Gly Gly Thr Ala Thr Gly Gly Cys Ala
1               5                   10                  15

Cys Gly Thr Gly Ala Thr Gly Gly Thr Cys Cys Ala Ala Cys Thr Cys
            20                  25                  30

Thr Thr Cys Gly Thr Gly Ala Ala Thr Gly Gly Cys Thr Thr Cys Gly
        35                  40                  45

Thr Ala Cys Thr Thr Ala Thr Cys Gly Thr Ala Thr Gly Ala Thr Gly
    50                  55                  60

Cys Ala Thr Thr Cys Thr Cys
65                  70

<210> SEQ ID NO 58
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 58

Thr Cys Gly Ala Gly Ala Gly Ala Ala Thr Gly Cys Ala Thr Cys Ala
1               5                   10                  15

Thr Ala Cys Gly Ala Thr Ala Ala Gly Thr Ala Cys Gly Ala Ala Gly
            20                  25                  30

Cys Cys Ala Thr Thr Cys Ala Cys Gly Ala Ala Gly Ala Gly Thr Thr
        35                  40                  45

Gly Gly Ala Cys Cys Ala Thr Cys Ala Cys Gly Thr Gly Cys Cys Ala
    50                  55                  60

Thr Ala Cys Cys Thr Thr Gly
65                  70

<210> SEQ ID NO 59
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 59

```
gt gca caa ggt atg gca cgt gat ggt cca act ctt cgt gaa tgg ctt      47
   Ala Gln Gly Met Ala Arg Asp Gly Pro Thr Leu Arg Glu Trp Leu
   1               5                  10                  15 cgt act tat cgt atg atg cat tct ctc gag                             77
Arg Thr Tyr Arg Met Met His Ser Leu Glu
                20                  25
```

<210> SEQ ID NO 60
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 60

```
Ala Gln Gly Met Ala Arg Asp Gly Pro Thr Leu Arg Glu Trp Leu Arg
1               5                   10                  15

Thr Tyr Arg Met Met His Ser Leu Glu
            20                  25
```

<210> SEQ ID NO 61
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 61

```
Thr Gly Cys Ala Cys Ala Ala Gly Gly Ala Thr Gly Gly Ala Thr Gly
1               5                   10                  15

Cys Cys Ala Gly Ala Ala Gly Gly Ala Cys Cys Ala Ala Cys Ala Thr
                20                  25                  30

Thr Ala Ala Ala Ala Cys Ala Ala Thr Gly Gly Cys Thr Thr Thr
            35                  40                  45

Thr Cys Ala Thr Gly Gly Thr Cys Gly Thr Gly Gly Thr Cys Ala Ala
    50                  55                  60

Cys Ala Thr Thr Cys Thr Cys
65                  70
```

<210> SEQ ID NO 62
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 62

```
Thr Cys Gly Ala Gly Ala Gly Ala Ala Thr Gly Thr Thr Gly Ala Cys
1               5                   10                  15

Cys Ala Cys Gly Ala Cys Cys Ala Thr Gly Ala Ala Ala Ala Gly
                20                  25                  30

Cys Cys Ala Thr Thr Gly Thr Thr Thr Thr Ala Ala Thr Gly Thr Thr
            35                  40                  45

Gly Gly Thr Cys Cys Thr Thr Cys Thr Gly Gly Cys Ala Thr Cys Cys
    50                  55                  60

Ala Thr Cys Cys Thr Thr Gly
65                  70
```

<210> SEQ ID NO 63
<211> LENGTH: 77
<212> TYPE: DNA

```
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 63 gt gca caa gga tgg atg cca gaa gga cca aca tta aaa caa tgg ctt          47
   Ala Gln Gly Trp Met Pro Glu Gly Pro Thr Leu Lys Gln Trp Leu
    1               5                  10                  15 ttt cat ggt cgt ggt caa cat tct ctc gag                                 77
Phe His Gly Arg Gly Gln His Ser Leu Glu
            20                  25

<210> SEQ ID NO 64
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 64

Ala Gln Gly Trp Met Pro Glu Gly Pro Thr Leu Lys Gln Trp Leu Phe
 1               5                  10                  15

His Gly Arg Gly Gln His Ser Leu Glu
            20                  25

<210> SEQ ID NO 65
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 65

Thr Gly Cys Ala Cys Ala Ala Gly Gly Ala Cys Ala Thr Ala Thr Thr
 1               5                  10                  15

Cys Gly Thr Gly Ala Ala Gly Gly Thr Cys Cys Ala Ala Cys Ala Thr
            20                  25                  30

Thr Ala Cys Gly Thr Cys Ala Ala Thr Gly Gly Cys Thr Thr Gly Thr
        35                  40                  45

Thr Gly Cys Thr Cys Thr Thr Cys Gly Thr Ala Thr Gly Gly Thr Thr
    50                  55                  60

Cys Ala Thr Thr Cys Thr Cys
65                  70

<210> SEQ ID NO 66
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 66

Thr Cys Gly Ala Gly Ala Gly Ala Ala Thr Gly Ala Ala Cys Cys Ala
 1               5                  10                  15

Thr Ala Cys Gly Ala Ala Gly Ala Gly Cys Ala Ala Cys Ala Ala Gly
            20                  25                  30

Cys Cys Ala Thr Thr Gly Ala Cys Gly Thr Ala Ala Thr Gly Thr Thr
        35                  40                  45

Gly Gly Ala Cys Cys Thr Thr Cys Ala Cys Gly Ala Ala Thr Ala Thr
```

```
                          50                  55                  60
Gly Thr Cys Cys Thr Thr Gly
 65                  70

<210> SEQ ID NO 67
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 67 gt gca caa gga cat att cgt gaa ggt cca aca tta cgt caa tgg ctt        47
   Ala Gln Gly His Ile Arg Glu Gly Pro Thr Leu Arg Gln Trp Leu
    1               5                  10                  15 gtt gct ctt cgt atg gtt cat tct ctc gag                               77
Val Ala Leu Arg Met Val His Ser Leu Glu
                 20                  25

<210> SEQ ID NO 68
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 68

Ala Gln Gly His Ile Arg Glu Gly Pro Thr Leu Arg Gln Trp Leu Val
 1               5                  10                  15

Ala Leu Arg Met Val His Ser Leu Glu
             20                  25

<210> SEQ ID NO 69
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 69

Thr Gly Cys Ala Cys Ala Ala Gly Gly Thr Cys Ala Ala Thr Thr Ala
 1               5                  10                  15

Gly Gly Ala Cys Ala Thr Gly Gly Thr Cys Cys Ala Ala Cys Thr Cys
             20                  25                  30

Thr Thr Cys Gly Thr Cys Ala Ala Thr Gly Gly Cys Thr Thr Thr Cys
         35                  40                  45

Thr Thr Gly Gly Thr Ala Thr Cys Gly Thr Gly Thr Ala Thr Gly
         50                  55                  60

Cys Ala Thr Thr Cys Thr Cys
 65                  70

<210> SEQ ID NO 70
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 70

Thr Cys Gly Ala Gly Ala Gly Ala Ala Thr Gly Cys Ala Thr Ala Cys
```

```
                1               5                   10                  15
Cys Ala Cys Gly Ala Thr Ala Cys Cys Ala Ala Gly Ala Ala Ala Gly
                20                  25                  30

Cys Cys Ala Thr Thr Gly Ala Cys Gly Ala Ala Gly Ala Gly Thr Thr
                35                  40                  45

Gly Gly Ala Cys Cys Ala Thr Gly Thr Cys Thr Ala Ala Thr Thr
        50                  55                  60

Gly Ala Cys Cys Thr Thr Gly
65                  70

<210> SEQ ID NO 71
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 71 gt gca caa ggt caa tta gga cat ggt cca act ctt cgt caa tgg ctt        47
   Ala Gln Gly Gln Leu Gly His Gly Pro Thr Leu Arg Gln Trp Leu
   1               5                   10                  15 tct tgg tat cgt ggt atg cat tct ctc gag                               77
Ser Trp Tyr Arg Gly Met His Ser Leu Glu
                20                  25

<210> SEQ ID NO 72
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 72

Ala Gln Gly Gln Leu Gly His Gly Pro Thr Leu Arg Gln Trp Leu Ser
1               5                   10                  15

Trp Tyr Arg Gly Met His Ser Leu Glu
            20                  25

<210> SEQ ID NO 73
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 73

Thr Gly Cys Ala Cys Ala Ala Gly Gly Ala Gly Ala Ala Thr Thr Ala
1               5                   10                  15

Cys Gly Thr Cys Ala Ala Gly Gly Ala Cys Cys Ala Ala Thr Cys
                20                  25                  30

Thr Thr Cys Ala Thr Gly Ala Ala Thr Gly Gly Cys Thr Thr Cys Ala
            35                  40                  45

Ala Cys Ala Thr Thr Ala Gly Cys Ala Ala Gly Cys Ala Ala Ala
        50                  55                  60

Cys Ala Thr Thr Cys Thr Cys
65                  70

<210> SEQ ID NO 74
```

```
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 74

Thr Cys Gly Ala Gly Ala Gly Ala Ala Thr Gly Thr Thr Thr Gly Cys
1               5                   10                  15

Thr Thr Gly Cys Thr Ala Ala Ala Thr Gly Thr Thr Gly Ala Ala Gly
                20                  25                  30

Cys Cys Ala Thr Thr Cys Ala Thr Gly Ala Ala Gly Ala Gly Thr Thr
            35                  40                  45

Gly Gly Thr Cys Cys Thr Thr Gly Ala Cys Gly Thr Ala Ala Thr Thr
        50                  55                  60

Cys Thr Cys Cys Thr Thr Gly
65                  70

<210> SEQ ID NO 75
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 75 gt gca caa gga gaa tta cgt caa gga cca act ctt cat gaa tgg ctt       47
   Ala Gln Gly Glu Leu Arg Gln Gly Pro Thr Leu His Glu Trp Leu
   1               5                   10                  15 caa cat tta gca agc aaa cat tct ctc gag                              77
Gln His Leu Ala Ser Lys His Ser Leu Glu
                20                  25

<210> SEQ ID NO 76
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 76

Ala Gln Gly Glu Leu Arg Gln Gly Pro Thr Leu His Glu Trp Leu Gln
1               5                   10                  15

His Leu Ala Ser Lys His Ser Leu Glu
                20                  25

<210> SEQ ID NO 77
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 77

Thr Gly Cys Ala Cys Ala Ala Gly Gly Ala Gly Thr Ala Gly Gly Thr
1               5                   10                  15

Ala Thr Thr Gly Ala Ala Gly Gly Thr Cys Cys Ala Ala Cys Ala Thr
                20                  25                  30

Thr Ala Cys Gly Thr Cys Ala Ala Thr Gly Gly Thr Thr Ala Gly Cys
            35                  40                  45
```

```
Thr Cys Ala Ala Cys Gly Thr Cys Thr Thr Ala Thr Cys Cys Ala
        50                  55                  60
Cys Ala Thr Thr Cys Thr Cys
 65                  70
```

<210> SEQ ID NO 78
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 78

```
Thr Cys Gly Ala Gly Ala Gly Ala Ala Thr Gly Thr Gly Gly Ala Thr
 1               5                  10                  15
Thr Ala Ala Gly Ala Cys Gly Thr Thr Gly Ala Gly Cys Thr Ala Ala
                20                  25                  30
Cys Cys Ala Thr Thr Gly Ala Cys Gly Thr Ala Ala Thr Gly Thr Thr
                35                  40                  45
Gly Gly Ala Cys Cys Thr Thr Cys Ala Ala Thr Ala Cys Cys Thr Ala
        50                  55                  60
Cys Thr Cys Cys Thr Thr Gly
 65                  70
```

<210> SEQ ID NO 79
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 79

```
gt gca caa gga gta ggt att gaa ggt cca aca tta cgt caa tgg tta       47
   Ala Gln Gly Val Gly Ile Glu Gly Pro Thr Leu Arg Gln Trp Leu
    1               5                  10                  15
gct caa cgt ctt aat cca cat tct ctc gag                              77
Ala Gln Arg Leu Asn Pro His Ser Leu Glu
                20                  25
```

<210> SEQ ID NO 80
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 80

```
Ala Gln Gly Val Gly Ile Glu Gly Pro Thr Leu Arg Gln Trp Leu Ala
 1               5                  10                  15
Gln Arg Leu Asn Pro His Ser Leu Glu
                20                  25
```

<210> SEQ ID NO 81
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 81

-continued

Thr Gly Cys Ala Cys Ala Ala Gly Gly Ala Thr Gly Gly Thr Cys Ala
1               5                   10                  15

Cys Gly Thr Gly Ala Thr Gly Gly Thr Cys Cys Ala Ala Cys Ala Cys
            20                  25                  30

Thr Thr Cys Gly Thr Gly Ala Ala Thr Gly Gly Cys Thr Thr Gly Cys
        35                  40                  45

Thr Thr Gly Gly Cys Gly Thr Gly Cys Thr Gly Thr Thr Gly Gly Ala
        50                  55                  60

Cys Ala Thr Ala Gly Thr Cys
65                  70

<210> SEQ ID NO 82
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 82

Thr Cys Gly Ala Gly Ala Cys Thr Ala Thr Gly Thr Cys Cys Ala Ala
1               5                   10                  15

Cys Ala Gly Cys Ala Cys Gly Cys Cys Ala Ala Gly Cys Ala Ala Gly
            20                  25                  30

Cys Cys Ala Thr Thr Cys Ala Cys Gly Ala Ala Gly Thr Gly Thr Thr
        35                  40                  45

Gly Gly Ala Cys Cys Ala Thr Cys Ala Cys Gly Thr Gly Ala Cys Cys
        50                  55                  60

Ala Thr Cys Cys Thr Thr Gly
65                  70

<210> SEQ ID NO 83
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 83 gt gca caa gga tgg tca cgt gat ggt cca aca ctt cgt gaa tgg ctt      47
   Ala Gln Gly Trp Ser Arg Asp Gly Pro Thr Leu Arg Glu Trp Leu
   1               5                   10                  15 gct tgg cgt gct gtt gga cat agt ctc gag                            77
Ala Trp Arg Ala Val Gly His Ser Leu Glu
                20                  25

<210> SEQ ID NO 84
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 84

Ala Gln Gly Trp Ser Arg Asp Gly Pro Thr Leu Arg Glu Trp Leu Ala
1               5                   10                  15

Trp Arg Ala Val Gly His Ser Leu Glu
            20                  25

<210> SEQ ID NO 85
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 85

```
Thr Gly Cys Ala Cys Ala Ala Gly Gly Ala Gly Cys Ala Gly Thr Thr
1               5                   10                  15

Cys Cys Ala Cys Ala Ala Gly Gly Ala Cys Cys Ala Ala Cys Thr Cys
            20                  25                  30

Thr Thr Ala Ala Ala Cys Ala Gly Thr Gly Gly Thr Thr Ala Thr Thr
        35                  40                  45

Ala Thr Gly Gly Cys Gly Thr Cys Gly Thr Thr Gly Thr Gly Cys Ala
    50                  55                  60

Cys Ala Thr Thr Cys Thr Cys
65                  70
```

<210> SEQ ID NO 86
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 86

```
Thr Cys Gly Ala Gly Ala Gly Ala Ala Thr Gly Thr Gly Cys Ala Cys
1               5                   10                  15

Ala Ala Cys Gly Ala Cys Gly Cys Cys Ala Thr Ala Ala Thr Ala Ala
            20                  25                  30

Cys Cys Ala Cys Thr Gly Thr Thr Thr Ala Ala Gly Ala Gly Thr Thr
        35                  40                  45

Gly Gly Thr Cys Cys Thr Thr Gly Thr Gly Gly Ala Ala Cys Thr Gly
    50                  55                  60

Cys Thr Cys Cys Thr Thr Gly
65                  70
```

<210> SEQ ID NO 87
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 87

```
gt gca caa gga gca gtt cca caa gga cca act ctt aaa cag tgg tta      47
   Ala Gln Gly Ala Val Pro Gln Gly Pro Thr Leu Lys Gln Trp Leu
   1               5                   10                  15 tta tgg cgt cgt tgt gca cat tct ctc gag                             77
Leu Trp Arg Arg Cys Ala His Ser Leu Glu
                20                  25
```

<210> SEQ ID NO 88
<211> LENGTH: 25
<212> TYPE: PRT
<213> ORGANISM: Artificial Sequence
<220> FEATURE:
<223> OTHER INFORMATION: Synthesized Peptide Sequence

```
<400> SEQUENCE: 88

Ala Gln Gly Ala Val Pro Gln Gly Pro Thr Leu Lys Gln Trp Leu Leu
1               5                  10                  15

Trp Arg Arg Cys Ala His Ser Leu Glu
            20                  25

<210> SEQ ID NO 89
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 89

Thr Gly Cys Ala Cys Ala Ala Gly Gly Thr Cys Gly Thr Ala Thr Thr
1               5                  10                  15

Cys Gly Thr Gly Ala Ala Gly Gly Thr Cys Cys Ala Ala Cys Thr Cys
                20                  25                  30

Thr Thr Ala Ala Ala Gly Ala Ala Thr Gly Gly Cys Thr Thr Gly Cys
            35                  40                  45

Thr Cys Ala Ala Cys Gly Thr Cys Gly Thr Gly Thr Thr Thr Thr
        50                  55                  60

Cys Ala Thr Ala Gly Thr Cys
65                  70

<210> SEQ ID NO 90
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 90

Thr Cys Gly Ala Gly Ala Cys Thr Ala Thr Gly Ala Ala Ala Ala Cys
1               5                  10                  15

Cys Ala Cys Gly Ala Cys Gly Thr Thr Gly Ala Gly Cys Ala Ala Gly
                20                  25                  30

Cys Cys Ala Thr Thr Cys Thr Thr Thr Ala Ala Gly Ala Gly Thr Thr
            35                  40                  45

Gly Gly Ala Cys Cys Thr Thr Cys Ala Cys Gly Ala Ala Thr Ala Cys
        50                  55                  60

Gly Ala Cys Cys Thr Thr Gly
65                  70

<210> SEQ ID NO 91
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 91 gt gca caa ggt cgt att cgt gaa ggt cca act ctt aaa gaa tgg ctt      47
   Ala Gln Gly Arg Ile Arg Glu Gly Pro Thr Leu Lys Glu Trp Leu
   1               5                  10                  15 gct caa cgt cgt ggt ttt cat agt ctc gag                             77
Ala Gln Arg Arg Gly Phe His Ser Leu Glu
```

<210> SEQ ID NO 92
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 92

Ala Gln Gly Arg Ile Arg Glu Gly Pro Thr Leu Lys Glu Trp Leu Ala
1               5                   10                  15

Gln Arg Arg Gly Phe His Ser Leu Glu
            20                  25

<210> SEQ ID NO 93
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 93

Thr Gly Cys Ala Cys Ala Ala Gly Gly Thr Cys Gly Thr Thr Thr Cys
1               5                   10                  15

Gly Cys Thr Gly Ala Ala Gly Gly Thr Cys Cys Ala Ala Cys Ala Cys
            20                  25                  30

Thr Thr Cys Gly Thr Gly Ala Ala Thr Gly Gly Thr Thr Ala Gly Ala
        35                  40                  45

Ala Cys Ala Ala Cys Gly Thr Ala Ala Cys Thr Thr Gly Thr Thr
    50                  55                  60

Cys Ala Thr Ala Gly Thr Cys
65                  70

<210> SEQ ID NO 94
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 94

Thr Cys Gly Ala Gly Ala Cys Thr Ala Thr Gly Ala Ala Cys Ala Ala
1               5                   10                  15

Gly Thr Thr Thr Ala Cys Gly Thr Thr Gly Thr Thr Cys Thr Ala Ala
            20                  25                  30

Cys Cys Ala Thr Thr Cys Ala Cys Gly Ala Ala Gly Thr Gly Thr Thr
        35                  40                  45

Gly Gly Ala Cys Cys Thr Thr Cys Ala Gly Cys Gly Ala Ala Ala Cys
    50                  55                  60

Gly Ala Cys Cys Thr Thr Gly
65                  70

<210> SEQ ID NO 95
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

```
<400> SEQUENCE: 95 gt gca caa ggt cgt ttc gct gaa ggt cca aca ctt cgt gaa tgg tta       47
   Ala Gln Gly Arg Phe Ala Glu Gly Pro Thr Leu Arg Glu Trp Leu
   1               5                  10                  15 gaa caa cgt aaa ctt gtt cat agt ctc gag                              77
Glu Gln Arg Lys Leu Val His Ser Leu Glu
             20                  25

<210> SEQ ID NO 96
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 96

Ala Gln Gly Arg Phe Ala Glu Gly Pro Thr Leu Arg Glu Trp Leu
1               5                  10                  15

Gln Arg Lys Leu Val His Ser Leu Glu
            20                  25

<210> SEQ ID NO 97
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 97

Thr Gly Cys Ala Cys Ala Ala Gly Gly Thr Gly Ala Thr Cys Gly Thr
1               5                  10                  15

Thr Thr Cys Cys Ala Ala Gly Gly Thr Cys Cys Ala Ala Cys Thr Cys
                20                  25                  30

Thr Thr Cys Gly Thr Gly Ala Ala Thr Gly Gly Cys Thr Thr Gly Cys
        35                  40                  45

Thr Gly Cys Ala Ala Thr Cys Cys Gly Thr Ala Gly Cys Gly Thr Ala
    50                  55                  60

Cys Ala Thr Ala Gly Thr Cys
65                  70

<210> SEQ ID NO 98
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 98

Thr Cys Gly Ala Gly Ala Cys Thr Ala Thr Gly Thr Ala Cys Gly Cys
1               5                  10                  15

Thr Ala Cys Gly Gly Ala Thr Thr Gly Cys Ala Gly Cys Ala Ala Gly
                20                  25                  30

Cys Cys Ala Thr Thr Cys Ala Cys Gly Ala Ala Gly Ala Gly Thr Thr
        35                  40                  45

Gly Gly Ala Cys Cys Thr Thr Gly Gly Ala Ala Ala Cys Gly Ala Thr
    50                  55                  60

Cys Ala Cys Cys Thr Thr Gly
65                  70

<210> SEQ ID NO 99
```

<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 99

```
gt gca caa ggt gat cgt ttc caa ggt cca act ctt cgt gaa tgg ctt      47
   Ala Gln Gly Asp Arg Phe Gln Gly Pro Thr Leu Arg Glu Trp Leu
   1               5                  10                  15 gct gca atc cgt agc gta cat agt ctc gag                              77
Ala Ala Ile Arg Ser Val His Ser Leu Glu
            20                  25
```

<210> SEQ ID NO 100
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 100

Ala Gln Gly Asp Arg Phe Gln Gly Pro Thr Leu Arg Glu Trp Leu Ala
1               5                  10                  15

Ala Ile Arg Ser Val His Ser Leu Glu
            20                  25

<210> SEQ ID NO 101
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 101

Thr Gly Cys Ala Cys Ala Ala Gly Gly Thr Gly Cys Thr Gly Gly Thr
1               5                  10                  15

Cys Gly Thr Gly Ala Ala Gly Gly Thr Cys Cys Ala Ala Cys Thr Cys
            20                  25                  30

Thr Ala Cys Gly Thr Gly Ala Ala Thr Gly Gly Cys Thr Thr Ala Ala
        35                  40                  45

Thr Ala Thr Gly Cys Gly Thr Gly Thr Thr Gly Gly Cys Ala Ala
    50                  55                  60

Cys Ala Thr Thr Cys Thr Cys
65                  70

<210> SEQ ID NO 102
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 102

Thr Cys Gly Ala Gly Ala Gly Ala Ala Thr Gly Thr Thr Gly Cys Cys
1               5                  10                  15

Ala Ala Ala Cys Ala Cys Gly Cys Ala Thr Ala Thr Thr Ala Ala Gly
            20                  25                  30

Cys Cys Ala Thr Thr Cys Ala Cys Gly Thr Ala Gly Ala Gly Thr Thr
        35                  40                  45

```
Gly Gly Ala Cys Cys Thr Thr Cys Ala Cys Gly Ala Cys Cys Ala Gly
    50                  55                  60

Cys Ala Cys Cys Thr Thr Gly
65                  70
```

<210> SEQ ID NO 103
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 103

```
gt gca caa ggt gct ggt cgt gaa ggt cca act cta cgt gaa tgg ctt      47
   Ala Gln Gly Ala Gly Arg Glu Gly Pro Thr Leu Arg Glu Trp Leu
   1               5                   10                  15 aat atg cgt gtt tgg caa cat tct ctc gag                              77
Asn Met Arg Val Trp Gln His Ser Leu Glu
            20                  25
```

<210> SEQ ID NO 104
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 104

```
Ala Gln Gly Ala Gly Arg Glu Gly Pro Thr Leu Arg Glu Trp Leu Asn
1               5                   10                  15

Met Arg Val Trp Gln His Ser Leu Glu
            20                  25
```

<210> SEQ ID NO 105
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 105

```
Thr Gly Cys Ala Cys Ala Ala Gly Gly Ala Gly Cys Thr Thr Ala
1               5                   10                  15

Cys Ala Ala Gly Ala Ala Gly Gly Ala Cys Cys Ala Ala Cys Ala Thr
                20                  25                  30

Thr Ala Cys Gly Thr Cys Ala Ala Thr Gly Gly Thr Thr Ala Gly Gly
            35                  40                  45

Ala Thr Gly Gly Gly Gly Thr Cys Ala Ala Thr Gly Gly Gly Ala
        50                  55                  60

Cys Ala Cys Thr Cys Thr Cys
65                  70
```

<210> SEQ ID NO 106
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 106

```
Thr Cys Gly Ala Gly Ala Gly Thr Gly Thr Cys Cys Cys
1               5                   10                  15

Ala Thr Thr Gly Ala Cys Cys Cys Ala Thr Cys Cys Thr Ala Ala
                20                  25                  30

Cys Cys Ala Thr Thr Gly Ala Cys Gly Thr Ala Ala Thr Gly Thr Thr
                35                  40                  45

Gly Gly Thr Cys Cys Thr Thr Cys Thr Thr Gly Thr Ala Ala Ala Gly
            50                  55                  60

Cys Thr Cys Cys Thr Thr Gly
65                  70
```

<210> SEQ ID NO 107
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 107

```
gt gca caa gga gct tta caa gaa gga cca aca tta cgt caa tgg tta    47
   Ala Gln Gly Ala Leu Gln Glu Gly Pro Thr Leu Arg Gln Trp Leu
   1               5                   10                  15 gga tgg ggt caa tgg gga cac tct ctc gag                           77
Gly Trp Gly Gln Trp Gly His Ser Leu Glu
                20                  25
```

<210> SEQ ID NO 108
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 108

```
Ala Gln Gly Ala Leu Gln Glu Gly Pro Thr Leu Arg Gln Trp Leu Gly
1               5                   10                  15

Trp Gly Gln Trp Gly His Ser Leu Glu
            20                  25
```

<210> SEQ ID NO 109
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 109

```
Thr Gly Cys Ala Cys Ala Ala Gly Gly Ala Thr Ala Cys Thr Gly Thr
1               5                   10                  15

Gly Ala Thr Gly Ala Ala Gly Gly Thr Cys Cys Ala Ala Cys Thr Cys
                20                  25                  30

Thr Thr Ala Ala Ala Cys Ala Ala Thr Gly Gly Thr Thr Ala Gly Thr
            35                  40                  45

Ala Thr Gly Thr Cys Thr Thr Gly Gly Thr Thr Ala Cys Ala Ala
        50                  55                  60

Cys Ala Thr Ala Gly Thr Cys
65                  70
```

-continued

```
<210> SEQ ID NO 110
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 110

Thr Cys Gly Ala Gly Ala Cys Thr Ala Thr Gly Thr Thr Gly Thr Ala
1               5                   10                  15

Ala Ala Cys Cys Ala Ala Gly Ala Cys Ala Thr Ala Cys Thr Ala Ala
            20                  25                  30

Cys Cys Ala Thr Thr Gly Thr Thr Thr Ala Ala Gly Ala Gly Thr Thr
        35                  40                  45

Gly Gly Ala Cys Cys Thr Thr Cys Ala Thr Cys Ala Cys Ala Gly Thr
    50                  55                  60

Ala Thr Cys Cys Thr Thr Gly
65                  70

<210> SEQ ID NO 111
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 111 gt gca caa gga tac tgt gat gaa ggt cca act ctt aaa caa tgg tta      47
   Ala Gln Gly Tyr Cys Asp Glu Gly Pro Thr Leu Lys Gln Trp Leu
   1               5                   10                  15 gta tgt ctt ggt tta caa cat agt ctc gag                             77
Val Cys Leu Gly Leu Gln His Ser Leu Glu
                20                  25

<210> SEQ ID NO 112
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 112

Ala Gln Gly Tyr Cys Asp Glu Gly Pro Thr Leu Lys Gln Trp Leu Val
1               5                   10                  15

Cys Leu Gly Leu Gln His Ser Leu Glu
            20                  25

<210> SEQ ID NO 113
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 113

Thr Gly Cys Ala Cys Ala Ala Gly Gly Ala Thr Gly Thr Ala Gly Thr
1               5                   10                  15

Thr Cys Ala Gly Gly Ala Gly Gly Thr Cys Cys Ala Ala Cys Thr Thr
            20                  25                  30
```

-continued

```
Thr Ala Cys Gly Thr Gly Ala Ala Thr Gly Gly Thr Thr Ala Cys Ala
            35                  40                  45
Ala Thr Gly Thr Cys Gly Thr Cys Gly Thr Ala Thr Gly Cys Ala Ala
        50                  55                  60
Cys Ala Thr Thr Cys Thr Cys
65                  70

<210> SEQ ID NO 114
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 114

Thr Cys Gly Ala Gly Ala Gly Ala Ala Thr Gly Thr Thr Gly Cys Ala
1               5                   10                  15
Thr Ala Cys Gly Ala Cys Gly Ala Cys Ala Thr Thr Gly Thr Ala Ala
            20                  25                  30
Cys Cys Ala Thr Thr Cys Ala Cys Gly Thr Ala Ala Gly Thr Thr Thr
        35                  40                  45
Gly Gly Ala Cys Cys Thr Cys Cys Thr Gly Ala Ala Cys Thr Ala Cys
    50                  55                  60
Ala Thr Cys Cys Thr Thr Gly
65                  70

<210> SEQ ID NO 115
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 115 gt gca caa gga tgt agt tca gga ggt cca act tta cgt gaa tgg tta        47
   Ala Gln Gly Cys Ser Ser Gly Gly Pro Thr Leu Arg Glu Trp Leu
   1               5                   10                  15 caa tgt cgt cgt atg caa cat tct ctc gag                               77
Gln Cys Arg Arg Met Gln His Ser Leu Glu
            20                  25

<210> SEQ ID NO 116
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 116

Ala Gln Gly Cys Ser Ser Gly Gly Pro Thr Leu Arg Glu Trp Leu Gln
1               5                   10                  15
Cys Arg Arg Met Gln His Ser Leu Glu
            20                  25

<210> SEQ ID NO 117
<211> LENGTH: 71
<212> TYPE: PRT
<213> ORGANISM: Artificial Sequence
<220> FEATURE:
<223> OTHER INFORMATION: Synthesized Peptide Sequence
```

<400> SEQUENCE: 117

Thr Gly Cys Ala Cys Ala Ala Gly Gly Ala Thr Gly Thr Thr Cys Ala
1               5                   10                  15
Thr Gly Gly Gly Thr Gly Gly Thr Cys Cys Ala Ala Cys Thr Cys
            20                  25                  30
Thr Thr Ala Ala Cys Ala Ala Thr Gly Gly Thr Thr Ala Cys Ala
        35                  40                  45
Ala Thr Gly Thr Gly Thr Thr Cys Gly Thr Gly Cys Thr Ala Ala Ala
    50                  55                  60
Cys Ala Thr Thr Cys Thr Cys
65                  70

<210> SEQ ID NO 118
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 118

Thr Cys Gly Ala Gly Ala Gly Ala Ala Thr Gly Thr Thr Thr Ala Gly
1               5                   10                  15
Cys Ala Cys Gly Ala Ala Cys Ala Cys Ala Thr Thr Gly Thr Ala Ala
            20                  25                  30
Cys Cys Ala Thr Thr Gly Thr Thr Thr Ala Ala Gly Ala Gly Thr Thr
        35                  40                  45
Gly Gly Ala Cys Cys Ala Cys Cys Cys Cys Ala Thr Gly Ala Ala Cys
    50                  55                  60
Ala Thr Cys Cys Thr Thr Gly
65                  70

<210> SEQ ID NO 119
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 119 gt gca caa gga tgt tca tgg ggt ggt cca act ctt aaa caa tgg tta         47
   Ala Gln Gly Cys Ser Trp Gly Gly Pro Thr Leu Lys Gln Trp Leu
   1               5                   10                  15 caa tgt gtt cgt gct aaa cat tct ctc gag                                77
Gln Cys Val Arg Ala Lys His Ser Leu Glu
                20                  25

<210> SEQ ID NO 120
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 120

Ala Gln Gly Cys Ser Trp Gly Gly Pro Thr Leu Lys Gln Trp Leu Gln
1               5                   10                  15
Cys Val Arg Ala Lys His Ser Leu Glu
            20                  25

<210> SEQ ID NO 121
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 121

Thr Gly Cys Ala Cys Ala Ala Gly Gly Ala Thr Gly Thr Cys Ala Ala
1               5                   10                  15

Thr Thr Ala Gly Gly Thr Gly Gly Thr Cys Cys Gly Ala Cys Thr Cys
            20                  25                  30

Thr Thr Cys Gly Thr Gly Ala Ala Thr Gly Gly Cys Thr Thr Gly Cys
        35                  40                  45

Thr Thr Gly Thr Cys Gly Thr Cys Thr Thr Gly Gly Thr Gly Cys Thr
    50                  55                  60

Cys Ala Thr Thr Cys Ala Cys
65                  70

<210> SEQ ID NO 122
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 122

Thr Cys Gly Ala Gly Thr Gly Ala Ala Thr Gly Ala Gly Cys Ala Cys
1               5                   10                  15

Cys Ala Ala Gly Ala Cys Gly Ala Cys Ala Ala Gly Cys Ala Ala Gly
            20                  25                  30

Cys Cys Ala Thr Thr Cys Ala Cys Gly Ala Ala Gly Ala Gly Thr Cys
        35                  40                  45

Gly Gly Ala Cys Cys Ala Cys Cys Thr Ala Ala Thr Thr Gly Ala Cys
    50                  55                  60

Ala Thr Cys Cys Thr Thr Gly
65                  70

<210> SEQ ID NO 123
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 123 gt gca caa gga tgt caa tta ggt ggt ccg act ctt cgt gaa tgg ctt      47
   Ala Gln Gly Cys Gln Leu Gly Gly Pro Thr Leu Arg Glu Trp Leu
   1               5                   10                  15 gct tgt cgt ctt ggt gct cat tca ctc gag                             77
Ala Cys Arg Leu Gly Ala His Ser Leu Glu
                20                  25

<210> SEQ ID NO 124
<211> LENGTH: 25
<212> TYPE: PRT
<213> ORGANISM: Artificial Sequence

```
<220> FEATURE:
<223> OTHER INFORMATION: Synthesized Peptide Sequence

<400> SEQUENCE: 124

Ala Gln Gly Cys Gln Leu Gly Gly Pro Thr Leu Arg Glu Trp Leu Ala
1               5                   10                  15

Cys Arg Leu Gly Ala His Ser Leu Glu
            20                  25

<210> SEQ ID NO 125
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 125

Thr Gly Cys Ala Cys Ala Ala Gly Gly Ala Thr Gly Thr Thr Gly Gly
1               5                   10                  15

Gly Ala Ala Gly Gly Thr Gly Gly Thr Cys Cys Thr Ala Cys Ala Cys
            20                  25                  30

Thr Thr Ala Ala Ala Gly Ala Ala Thr Gly Gly Cys Thr Thr Cys Ala
            35                  40                  45

Ala Thr Gly Thr Cys Thr Thr Gly Thr Ala Gly Ala Ala Cys Gly Thr
        50                  55                  60

Cys Ala Thr Thr Cys Ala Cys
65                  70

<210> SEQ ID NO 126
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 126

Thr Cys Gly Ala Gly Thr Gly Ala Ala Thr Gly Ala Cys Gly Thr Thr
1               5                   10                  15

Cys Thr Ala Cys Ala Ala Gly Ala Cys Ala Thr Thr Gly Ala Ala Gly
            20                  25                  30

Cys Cys Ala Thr Thr Cys Thr Thr Thr Ala Ala Gly Thr Gly Thr Ala
            35                  40                  45

Gly Gly Ala Cys Cys Ala Cys Cys Thr Thr Cys Cys Cys Ala Ala Cys
        50                  55                  60

Ala Thr Cys Cys Thr Thr Gly
65                  70

<210> SEQ ID NO 127
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 127 gt gca caa gga tgt tgg gaa ggt ggt cct aca ctt aaa gaa tgg ctt      47
   Ala Gln Gly Cys Trp Glu Gly Gly Pro Thr Leu Lys Glu Trp Leu
   1               5                   10                  15
```

```
caa tgt ctt gta gaa cgt cat tca ctc gag                                77
Gln Cys Leu Val Glu Arg His Ser Leu Glu
            20                  25
```

<210> SEQ ID NO 128
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 128

```
Ala Gln Gly Cys Trp Glu Gly Gly Pro Thr Leu Lys Glu Trp Leu Gln
1               5                   10                  15

Cys Leu Val Glu Arg His Ser Leu Glu
            20                  25
```

<210> SEQ ID NO 129
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 129

```
Thr Gly Cys Ala Cys Ala Ala Gly Gly Thr Thr Gly Thr Cys Gly Thr
1               5                   10                  15

Gly Gly Thr Gly Gly Thr Gly Gly Thr Cys Cys Ala Ala Cys Thr Cys
            20                  25                  30

Thr Thr Cys Ala Thr Cys Ala Ala Thr Gly Gly Cys Thr Thr Thr Cys
            35                  40                  45

Thr Thr Gly Thr Thr Thr Thr Cys Gly Thr Thr Gly Gly Cys Ala Ala
            50                  55                  60

Cys Ala Thr Thr Cys Ala Cys
65                  70
```

<210> SEQ ID NO 130
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 130

```
Thr Cys Gly Ala Gly Thr Gly Ala Ala Thr Gly Thr Thr Gly Cys Cys
1               5                   10                  15

Ala Ala Cys Gly Ala Ala Ala Cys Ala Ala Gly Ala Ala Ala Gly
            20                  25                  30

Cys Cys Ala Thr Thr Gly Ala Thr Gly Ala Ala Gly Ala Gly Thr Thr
            35                  40                  45

Gly Gly Ala Cys Cys Ala Cys Cys Ala Cys Cys Ala Cys Gly Ala Cys
            50                  55                  60

Ala Ala Cys Cys Thr Thr Gly
65                  70
```

<210> SEQ ID NO 131
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS

```
<222> LOCATION: (3)..(77)
<223> OTHER INFORMATION:

<400> SEQUENCE: 131 gt gca caa ggt tgt cgt ggt ggt ggt cca act ctt cat caa tgg ctt        47
   Ala Gln Gly Cys Arg Gly Gly Gly Pro Thr Leu His Gln Trp Leu
   1               5                  10                  15 tct tgt ttt cgt tgg caa cat tca ctc gag                               77
Ser Cys Phe Arg Trp Gln His Ser Leu Glu
                20                  25

<210> SEQ ID NO 132
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 132

Ala Gln Gly Cys Arg Gly Gly Gly Pro Thr Leu His Gln Trp Leu Ser
1               5                   10                  15

Cys Phe Arg Trp Gln His Ser Leu Glu
            20                  25

<210> SEQ ID NO 133
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 133

Thr Gly Cys Ala Cys Ala Ala Gly Gly Ala Thr Gly Thr Cys Gly Thr
1               5                   10                  15

Gly Ala Thr Gly Gly Thr Gly Thr Cys Cys Ala Ala Cys Thr Cys
            20                  25                  30

Thr Thr Ala Gly Ala Cys Ala Ala Thr Gly Gly Cys Thr Thr Gly Cys
        35                  40                  45

Thr Thr Gly Thr Cys Thr Thr Cys Ala Ala Cys Ala Ala Ala Ala
            50                  55                  60

Cys Ala Thr Thr Cys Ala Cys
65                  70

<210> SEQ ID NO 134
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 134

Thr Cys Gly Ala Gly Thr Gly Ala Ala Thr Gly Thr Thr Thr Thr
1               5                   10                  15

Gly Thr Thr Gly Ala Ala Gly Ala Cys Ala Ala Gly Cys Ala Ala Gly
            20                  25                  30

Cys Cys Ala Thr Thr Gly Thr Cys Thr Ala Gly Ala Gly Thr Thr
        35                  40                  45

Gly Gly Ala Cys Cys Ala Cys Cys Ala Thr Cys Ala Cys Gly Ala Cys
            50                  55                  60

Ala Thr Cys Cys Thr Thr Gly
65                  70
```

```
<210> SEQ ID NO 135
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 135 gt gca caa gga tgt cgt gat ggt ggt cca act ctt aga caa tgg ctt      47
   Ala Gln Gly Cys Arg Asp Gly Gly Pro Thr Leu Arg Gln Trp Leu
   1               5                   10                  15 gct tgt ctt caa caa aaa cat tca ctc gag                              77
Ala Cys Leu Gln Gln Lys His Ser Leu Glu
            20                  25

<210> SEQ ID NO 136
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 136

Ala Gln Gly Cys Arg Asp Gly Gly Pro Thr Leu Arg Gln Trp Leu Ala
1               5                   10                  15

Cys Leu Gln Gln Lys His Ser Leu Glu
            20                  25

<210> SEQ ID NO 137
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 137

Thr Cys Gly Ala Gly Thr Gly Ala Ala Thr Gly Thr Thr Gly Ala Gly
1               5                   10                  15

Cys Ala Ala Gly Ala Cys Gly Cys Cys Ala Ala Ala Cys Ala Ala Gly
            20                  25                  30

Cys Cys Ala Thr Thr Cys Thr Thr Thr Ala Ala Ala Gly Thr Thr
        35                  40                  45

Gly Gly Ala Cys Cys Ala Gly Ala Thr Cys Thr Thr Ala Ala Thr Thr
    50                  55                  60

Cys Thr Cys Cys Thr Thr Gly
65                  70

<210> SEQ ID NO 138
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 138

Thr Gly Cys Ala Cys Ala Ala Gly Gly Ala Gly Ala Ala Thr Thr Ala
1               5                   10                  15

Ala Gly Ala Thr Cys Thr Gly Gly Thr Cys Cys Ala Ala Cys Thr Thr
            20                  25                  30
```

```
Thr Ala Ala Ala Ala Gly Ala Ala Thr Gly Gly Cys Thr Thr Gly Thr
        35                  40                  45

Thr Thr Gly Gly Cys Gly Thr Cys Thr Thr Gly Cys Thr Cys Ala Ala
    50                  55                  60

Cys Ala Thr Thr Cys Ala Cys
65                  70
```

<210> SEQ ID NO 139
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 139

```
gt gca caa gga gaa tta aga tct ggt cca act tta aaa gaa tgg ctt     47
   Ala Gln Gly Glu Leu Arg Ser Gly Pro Thr Leu Lys Glu Trp Leu
   1               5                   10                  15 gtt tgg cgt ctt gct caa cat tca ctc gag                            77
Val Trp Arg Leu Ala Gln His Ser Leu Glu
                20                  25
```

<210> SEQ ID NO 140
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 140

```
Ala Gln Gly Glu Leu Arg Ser Gly Pro Thr Leu Lys Glu Trp Leu Val
1               5                   10                  15

Trp Arg Leu Ala Gln His Ser Leu Glu
            20                  25
```

<210> SEQ ID NO 141
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 141

```
Thr Gly Cys Ala Cys Ala Ala Gly Gly Ala Gly Gly Ala Thr Gly Thr
1               5                   10                  15

Ala Gly Ala Thr Cys Thr Gly Gly Thr Cys Cys Ala Ala Cys Ala Cys
                20                  25                  30

Thr Thr Cys Gly Thr Gly Ala Ala Thr Gly Gly Thr Thr Ala Gly Cys
        35                  40                  45

Thr Thr Gly Thr Ala Gly Ala Gly Gly Thr Thr Cys Ala Ala
    50                  55                  60

Cys Ala Cys Thr Cys Thr Cys
65                  70
```

<210> SEQ ID NO 142
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 142

Thr Cys Gly Ala Gly Ala Gly Ala Gly Thr Gly Thr Thr Gly Ala Ala
1               5                   10                  15

Cys Cys Thr Cys Thr Cys Thr Ala Cys Ala Ala Gly Cys Thr Ala Ala
                20                  25                  30

Cys Cys Ala Thr Thr Cys Ala Cys Gly Ala Ala Gly Thr Gly Thr Thr
            35                  40                  45

Gly Gly Ala Cys Cys Ala Gly Ala Thr Cys Thr Ala Cys Ala Thr Cys
        50                  55                  60

Cys Thr Cys Cys Thr Thr Gly
65                  70

<210> SEQ ID NO 143
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 143 gt gca caa gga gga tgt aga tct ggt cca aca ctt cgt gaa tgg tta      47
   Ala Gln Gly Gly Cys Arg Ser Gly Pro Thr Leu Arg Glu Trp Leu
   1               5                   10                  15 gct tgt aga gag gtt caa cac tct ctc gag                             77
Ala Cys Arg Glu Val Gln His Ser Leu Glu
                20                  25

<210> SEQ ID NO 144
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 144

Ala Gln Gly Gly Cys Arg Ser Gly Pro Thr Leu Arg Glu Trp Leu Ala
1               5                   10                  15

Cys Arg Glu Val Gln His Ser Leu Glu
                20                  25

<210> SEQ ID NO 145
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 145

Thr Gly Cys Ala Cys Ala Ala Gly Gly Thr Ala Cys Ala Thr Gly Cys
1               5                   10                  15

Gly Ala Ala Cys Ala Ala Gly Gly Ala Cys Cys Ala Ala Cys Thr Cys
                20                  25                  30

Thr Ala Ala Gly Ala Cys Ala Ala Thr Gly Gly Cys Thr Ala Cys Thr
            35                  40                  45

Ala Thr Gly Thr Ala Gly Ala Cys Ala Ala Gly Gly Ala Ala Gly Ala
        50                  55                  60

Cys Ala Cys Thr Cys Ala Cys
65                  70

<210> SEQ ID NO 146
<211> LENGTH: 71
<212> TYPE: PRT
<213> ORGANISM: Artificial Sequence
<220> FEATURE:
<223> OTHER INFORMATION: Synthesized Peptide Sequence

<400> SEQUENCE: 146

Thr Cys Gly Ala Gly Thr Gly Ala Gly Thr Gly Thr Cys Thr Thr Cys
1               5                   10                  15

Cys Thr Thr Gly Thr Cys Thr Ala Cys Ala Thr Ala Gly Thr Ala Gly
                20                  25                  30

Cys Cys Ala Thr Thr Gly Thr Cys Thr Ala Gly Ala Gly Thr Thr
            35                  40                  45

Gly Gly Thr Cys Cys Thr Thr Gly Thr Thr Cys Gly Cys Ala Thr Gly
        50                  55                  60

Thr Ala Cys Cys Thr Thr Gly
65                  70

<210> SEQ ID NO 147
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 147 gt gca caa ggt aca tgc gaa caa gga cca act cta aga caa tgg cta        47
   Ala Gln Gly Thr Cys Glu Gln Gly Pro Thr Leu Arg Gln Trp Leu
   1               5                   10                  15 cta tgt aga caa gga aga cac tca ctc gag                                77
Leu Cys Arg Gln Gly Arg His Ser Leu Glu
                20                  25

<210> SEQ ID NO 148
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 148

Ala Gln Gly Thr Cys Glu Gln Gly Pro Thr Leu Arg Gln Trp Leu Leu
1               5                   10                  15

Cys Arg Gln Gly Arg His Ser Leu Glu
                20                  25

<210> SEQ ID NO 149
<211> LENGTH: 77
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (3)..(77)
<223> OTHER INFORMATION:

<400> SEQUENCE: 149

```
gt gca cag ggt tgg tgt aag gag ggt cct act ctg cgt gag tgg ctg      47
   Ala Gln Gly Trp Cys Lys Glu Gly Pro Thr Leu Arg Glu Trp Leu
   1               5                   10                  15 cgg tgg ggt ttt ctg tgt cat tct ctc gag                             77
Arg Trp Gly Phe Leu Cys His Ser Leu Glu
                20                  25

<210> SEQ ID NO 150
<211> LENGTH: 25
<212> TYPE: PRT
<213> ORGANISM: Artificial Sequence
<220> FEATURE:
<223> OTHER INFORMATION: Synthesized Peptide Sequence

<400> SEQUENCE: 150

Ala Gln Gly Trp Cys Lys Glu Gly Pro Thr Leu Arg Glu Trp Leu Arg
1               5                   10                  15

Trp Gly Phe Leu Cys His Ser Leu Glu
            20                  25

<210> SEQ ID NO 151
<211> LENGTH: 837
<212> TYPE: DNA
<213> ORGANISM: Artificial Sequence
<220> FEATURE:
<223> OTHER INFORMATION: Synthesized Peptide Sequence
<220> FEATURE:
<221> NAME/KEY: CDS
<222> LOCATION: (57)..(785)
<223> OTHER INFORMATION:

<400> SEQUENCE: 151
tcgattaatc gatttgattc tagatttgtt ttaactaatt aaaggaggaa taacat atg    59
                                                                Met
                                                                1 gac aaa act cac aca tgt cca cct tgt cca gct ccg gaa ctc ctg ggg    107
Asp Lys Thr His Thr Cys Pro Pro Cys Pro Ala Pro Glu Leu Leu Gly
        5                   10                  15 gga ccg tca gtc ttc ctc ttc ccc cca aaa ccc aag gac acc ctc atg    155
Gly Pro Ser Val Phe Leu Phe Pro Pro Lys Pro Lys Asp Thr Leu Met
    20                  25                  30 atc tcc cgg acc cct gag gtc aca tgc gtg gtg gtg gac gtg agc cac    203
Ile Ser Arg Thr Pro Glu Val Thr Cys Val Val Val Asp Val Ser His
35                  40                  45 gaa gac cct gag gtc aag ttc aac tgg tac gtg gac ggc gtg gag gtg    251
Glu Asp Pro Glu Val Lys Phe Asn Trp Tyr Val Asp Gly Val Glu Val
50                  55                  60                  65 cat aat gcc aag aca aag ccg cgg gag gag cag tac aac agc acg tac    299
His Asn Ala Lys Thr Lys Pro Arg Glu Glu Gln Tyr Asn Ser Thr Tyr
                70                  75                  80 cgt gtg gtc agc gtc ctc acc gtc ctg cac cag gac tgg ctg aat ggc    347
Arg Val Val Ser Val Leu Thr Val Leu His Gln Asp Trp Leu Asn Gly
            85                  90                  95 aag gag tac aag tgc aag gtc tcc aac aaa gcc ctc cca gcc ccc atc    395
Lys Glu Tyr Lys Cys Lys Val Ser Asn Lys Ala Leu Pro Ala Pro Ile
        100                 105                 110 gag aaa acc atc tcc aaa gcc aaa ggg cag ccc cga gaa cca cag gtg    443
Glu Lys Thr Ile Ser Lys Ala Lys Gly Gln Pro Arg Glu Pro Gln Val
    115                 120                 125 tac acc ctg ccc cca tcc cgg gat gag ctg acc aag aac cag gtc agc    491
Tyr Thr Leu Pro Pro Ser Arg Asp Glu Leu Thr Lys Asn Gln Val Ser
130                 135                 140                 145 ctg acc tgc ctg gtc aaa ggc ttc tat ccc agc gac atc gcc gtg gag    539
Leu Thr Cys Leu Val Lys Gly Phe Tyr Pro Ser Asp Ile Ala Val Glu
```

```
Leu Thr Cys Leu Val Lys Gly Phe Tyr Pro Ser Asp Ile Ala Val Glu
            150                 155                 160 tgg gag agc aat ggg cag ccg gag aac aac tac aag acc acg cct ccc      587
Trp Glu Ser Asn Gly Gln Pro Glu Asn Asn Tyr Lys Thr Thr Pro Pro
            165                 170                 175 gtg ctg gac tcc gac ggc tcc ttc ttc ctc tac agc aag ctc acc gtg      635
Val Leu Asp Ser Asp Gly Ser Phe Phe Leu Tyr Ser Lys Leu Thr Val
            180                 185                 190 gac aag agc agg tgg cag cag ggg aac gtc ttc tca tgc tcc gtg atg      683
Asp Lys Ser Arg Trp Gln Gln Gly Asn Val Phe Ser Cys Ser Val Met
            195                 200                 205 cat gag gct ctg cac aac cac tac acg cag aag agc ctc tcc ctg tct      731
His Glu Ala Leu His Asn His Tyr Thr Gln Lys Ser Leu Ser Leu Ser
210                 215                 220                 225 ccg ggt aaa ggt gga ggt ggt ggt gca cag aaa gcg gcc gca aaa aaa      779
Pro Gly Lys Gly Gly Gly Gly Gly Ala Gln Lys Ala Ala Ala Lys Lys
                230                 235                 240 ctc gag taatggatcc gcggaaagaa gaagaagaag aagaaagccc gaaaggaagc tg    837
Leu Glu
```

<210> SEQ ID NO 152
<211> LENGTH: 243
<212> TYPE: PRT
<213> ORGANISM: Artificial Sequence
<220> FEATURE:
<223> OTHER INFORMATION: Synthesized Peptide Sequence

<400> SEQUENCE: 152

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
        210                 215                 220

Ser Pro Gly Lys Gly Gly Gly Gly Gly Ala Gln Lys Ala Ala Ala Lys
```

```
                 225                 230                 235                 240

Lys Leu Glu

<210> SEQ ID NO 153
<211> LENGTH: 45
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (22)..(22)
<223> OTHER INFORMATION: At Position 22, PEG linker

<400> SEQUENCE: 153

His Ile Arg Glu Gly Pro Thr Leu Arg Gln Trp Leu Val Ala Leu Arg
1               5                   10                  15

Met Val Gly Gly Gly Pro Glu Gly Gly Gly His Ile Arg Glu Gly
            20                  25                  30

Pro Thr Leu Arg Gln Trp Leu Val Ala Leu Arg Met Val
        35                  40                  45

<210> SEQ ID NO 154
<211> LENGTH: 43
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At Position 1, Fc at N-terminus
<220> FEATURE:
<221> NAME/KEY: misc_feature
<222> LOCATION: (43)..(43)
<223> OTHER INFORMATION: At position 43, Fc on C-terminus

<400> SEQUENCE: 154

Thr Cys Glu Gln Gly Pro Thr Leu Arg Gln Trp Leu Leu Cys Arg Gln
1               5                   10                  15

Gly Arg Gly Gly Gly Lys Gly Gly Gly Thr Cys Glu Gln Gly Pro Thr
            20                  25                  30

Leu Arg Gln Trp Leu Leu Cys Arg Gln Gly Arg
        35                  40

<210> SEQ ID NO 155
<211> LENGTH: 40
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 155

Gln Leu Gly His Gly Pro Thr Leu Arg Gln Trp Leu Ser Trp Tyr Arg
1               5                   10                  15

Gly Met Gly Pro Asn Gly Glu Leu Arg Ser Gly Pro Thr Leu Lys Glu
            20                  25                  30

Trp Leu Val Trp Arg Leu Ala Gln
        35                  40

<210> SEQ ID NO 156
```

```
<211> LENGTH: 18
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (19)..(19)
<223> OTHER INFORMATION: At position 19, Fc at C-terminus

<400> SEQUENCE: 156

Cys Ser Trp Gly Gly Pro Thr Leu Lys Gln Trp Leu Gln Cys Val Arg
1               5                   10                  15
Ala Lys

<210> SEQ ID NO 157
<211> LENGTH: 25
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 157

Gly Gly Gly Lys Gly Gly Gly Ala Val Pro Gln Gly Pro Thr Leu Lys
1               5                   10                  15
Gln Trp Leu Leu Trp Arg Arg Cys Ala
            20                  25

<210> SEQ ID NO 158
<211> LENGTH: 18
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, PEG group attached

<400> SEQUENCE: 158

Cys Ser Ser Gly Gly Pro Thr Leu Arg Glu Trp Leu Gln Cys Arg Arg
1               5                   10                  15
Met Gln

<210> SEQ ID NO 159
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 159

Gly Gly Gly Gly Gly Tyr Cys Asp Glu Gly Pro Thr Leu Lys Gln Trp
1               5                   10                  15
Leu Val Cys Leu Gly Leu Gln Gly Gly Gly Gly Tyr Cys Asp Glu
            20                  25                  30
Gly Pro Thr Leu Lys Gln Trp Leu Val Cys Leu Gly Leu Gln
        35                  40                  45
```

```
<210> SEQ ID NO 160
<211> LENGTH: 75
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (76)..(76)
<223> OTHER INFORMATION: At position 76, Fc at C-terminus

<400> SEQUENCE: 160

Cys Ser Trp Gly Gly Pro Thr Leu Lys Gln Trp Leu Gln Cys Val Arg
1               5                   10                  15

Ala Lys Gly Gly Gly Ala Gly Gly Cys Ser Trp Gly Gly Pro Thr
        20                  25                  30

Leu Lys Gln Trp Leu Gln Cys Val Arg Ala Lys Gly Gly Gly Ala Gly
        35                  40                  45

Gly Gly Cys Ser Trp Gly Gly Pro Thr Leu Lys Gln Trp Leu Gln Cys
    50                  55                  60

Val Arg Ala Lys Gly Gly Gly Ala Gly Gly Gly
65                  70                  75

<210> SEQ ID NO 161
<211> LENGTH: 43
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (44)..(44)
<223> OTHER INFORMATION: At position 44, PEG group at C-terminus

<400> SEQUENCE: 161

Val Gly Ile Glu Gly Pro Thr Leu Arg Gln Trp Leu Ala Gln Arg Leu
1               5                   10                  15

Asn Pro Gly Gly Gly Cys Gly Gly Gly Val Gly Ile Glu Gly Pro Thr
            20                  25                  30

Leu Arg Gln Trp Leu Ala Gln Arg Leu Asn Pro
        35                  40

<210> SEQ ID NO 162
<211> LENGTH: 40
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 162

Glu Leu Arg Ser Gly Pro Thr Leu Lys Glu Trp Leu Val Trp Arg Leu
1               5                   10                  15

Ala Gln Gly Gly Gly Gly Glu Leu Arg Ser Gly Pro Thr Leu Lys Glu
            20                  25                  30

Trp Leu Val Trp Arg Leu Ala Gln
        35                  40

<210> SEQ ID NO 163
<211> LENGTH: 43
<212> TYPE: PRT
```

```
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus
<220> FEATURE:
<221> NAME/KEY: misc_feature
<222> LOCATION: (44)..(44)
<223> OTHER INFORMATION: At position 44, Fc at C-terminus

<400> SEQUENCE: 163

Ala Leu Arg Asp Gly Pro Thr Leu Lys Gln Trp Leu Glu Tyr Arg Arg
1               5                   10                  15

Gln Ala Gly Gly Gly Lys Gly Gly Ala Leu Arg Asp Gly Pro Thr
            20                  25                  30

Leu Lys Gln Trp Leu Glu Tyr Arg Arg Gln Ala
        35                  40

<210> SEQ ID NO 164
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 164

Ala Leu Arg Asp Gly Pro Thr Leu Lys Gln Trp Leu Glu Tyr Arg Arg
1               5                   10                  15

Gln Ala Ala Leu Arg Asp Gly Pro Thr Leu Lys Gln Trp Leu Glu Tyr
            20                  25                  30

Arg Arg Gln Ala
        35

<210> SEQ ID NO 165
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 165

Glu Ala Leu Leu Gly Pro Thr Leu Arg Glu Trp Leu Ala Trp Arg Arg
1               5                   10                  15

Ala Gln Glu Ala Leu Leu Gly Pro Thr Leu Arg Glu Trp Leu Ala Trp
            20                  25                  30

Arg Arg Ala Gln
        35

<210> SEQ ID NO 166
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 166

Ala Val Pro Gln Gly Pro Thr Leu Lys Gln Trp Leu Leu Trp Arg Arg
1               5                   10                  15

Cys Ala Ala Val Pro Gln Gly Pro Thr Leu Lys Gln Trp Leu Leu Trp
            20                  25                  30

Arg Arg Cys Ala
        35
```

<210> SEQ ID NO 167
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 167

Tyr Cys Asp Glu Gly Pro Thr Leu Lys Gln Trp Leu Val Cys Leu Gly
 1               5                  10                  15

Leu Gln Tyr Cys Asp Glu Gly Pro Thr Leu Lys Gln Trp Leu Val Cys
            20                  25                  30

Leu Gly Leu Gln
        35

<210> SEQ ID NO 168
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 168

Cys Ser Ser Gly Gly Pro Thr Leu Arg Glu Trp Leu Gln Cys Arg Arg
 1               5                  10                  15

Met Gln Cys Ser Ser Gly Gly Pro Thr Leu Arg Glu Trp Leu Gln Cys
            20                  25                  30

Arg Arg Met Gln
        35

<210> SEQ ID NO 169
<211> LENGTH: 36
<212> TYPE: PRT
<213> ORGANISM: Artificial Sequence
<220> FEATURE:
<223> OTHER INFORMATION: Synthesized Peptide Sequence

<400> SEQUENCE: 169

Cys Ser Trp Gly Gly Pro Thr Leu Lys Gln Trp Leu Gln Cys Val Arg
 1               5                  10                  15

Ala Lys Cys Ser Trp Gly Gly Pro Thr Leu Lys Gln Trp Leu Gln Cys
            20                  25                  30

Val Arg Ala Lys
        35

<210> SEQ ID NO 170
<211> LENGTH: 41
<212> TYPE: PRT
<213> ORGANISM: Artificial Sequence
<220> FEATURE:
<223> OTHER INFORMATION: Synthesized Peptide Sequence

<400> SEQUENCE: 170

Ala Leu Arg Asp Gly Pro Thr Leu Lys Gln Trp Leu Glu Tyr Arg Arg
 1               5                  10                  15

Gln Ala Gly Gly Gly Gly Gly Ala Leu Arg Asp Gly Pro Thr Leu Lys
            20                  25                  30

Gln Trp Leu Glu Tyr Arg Arg Gln Ala
        35                  40

<210> SEQ ID NO 171

```
<211> LENGTH: 41
<212> TYPE: PRT
<213> ORGANISM: Artificial Sequence
<220> FEATURE:
<223> OTHER INFORMATION: Synthesized Peptide Sequence

<400> SEQUENCE: 171

Glu Ala Leu Leu Gly Pro Thr Leu Arg Glu Trp Leu Ala Trp Arg Arg
1               5                   10                  15

Ala Gln Gly Gly Gly Gly Glu Ala Leu Leu Gly Pro Thr Leu Arg
            20                  25                  30

Glu Trp Leu Ala Trp Arg Arg Ala Gln
        35                  40

<210> SEQ ID NO 172
<211> LENGTH: 41
<212> TYPE: PRT
<213> ORGANISM: Artificial Sequence
<220> FEATURE:
<223> OTHER INFORMATION: Synthesized Peptide Sequence

<400> SEQUENCE: 172

Ala Val Pro Gln Gly Pro Thr Leu Lys Gln Trp Leu Leu Trp Arg Arg
1               5                   10                  15

Cys Ala Gly Gly Gly Gly Ala Val Pro Gln Gly Pro Thr Leu Lys
            20                  25                  30

Gln Trp Leu Leu Trp Arg Arg Cys Ala
        35                  40

<210> SEQ ID NO 173
<211> LENGTH: 41
<212> TYPE: PRT
<213> ORGANISM: Artificial Sequence
<220> FEATURE:
<223> OTHER INFORMATION: Synthesized Peptide Sequence

<400> SEQUENCE: 173

Tyr Cys Asp Glu Gly Pro Thr Leu Lys Gln Trp Leu Val Cys Leu Gly
1               5                   10                  15

Leu Gln Gly Gly Gly Gly Tyr Cys Asp Glu Gly Pro Thr Leu Lys
            20                  25                  30

Gln Trp Leu Val Cys Leu Gly Leu Gln
        35                  40

<210> SEQ ID NO 174
<211> LENGTH: 41
<212> TYPE: PRT
<213> ORGANISM: Artificial Sequence
<220> FEATURE:
<223> OTHER INFORMATION: Synthesized Peptide Sequence

<400> SEQUENCE: 174

Cys Ser Ser Gly Gly Pro Thr Leu Arg Glu Trp Leu Gln Cys Arg Arg
1               5                   10                  15

Met Gln Gly Gly Gly Gly Cys Ser Ser Gly Gly Pro Thr Leu Arg
            20                  25                  30

Glu Trp Leu Gln Cys Arg Arg Met Gln
        35                  40

<210> SEQ ID NO 175
<211> LENGTH: 41
<212> TYPE: PRT
<213> ORGANISM: Artificial Sequence
```

```
<220> FEATURE:
<223> OTHER INFORMATION: Synthesized Peptide Sequence

<400> SEQUENCE: 175

Cys Ser Trp Gly Gly Pro Thr Leu Lys Gln Trp Leu Gln Cys Val Arg
1               5                   10                  15

Ala Lys Gly Gly Gly Gly Cys Ser Trp Gly Gly Pro Thr Leu Lys
            20                  25                  30

Gln Trp Leu Gln Cys Val Arg Ala Lys
        35                  40

<210> SEQ ID NO 176
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 176

Gly Gly Gly Gly Gly Ala Leu Arg Asp Gly Pro Thr Leu Lys Gln Trp
1               5                   10                  15

Leu Glu Tyr Arg Arg Gln Ala
            20

<210> SEQ ID NO 177
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 177

Gly Gly Gly Gly Gly Glu Ala Leu Leu Gly Pro Thr Leu Arg Glu Trp
1               5                   10                  15

Leu Ala Trp Arg Arg Ala Gln
            20

<210> SEQ ID NO 178
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 178

Gly Gly Gly Gly Gly Ala Val Pro Gln Gly Pro Thr Leu Lys Gln Trp
1               5                   10                  15

Leu Leu Trp Arg Arg Cys Ala
            20

<210> SEQ ID NO 179
<211> LENGTH: 23
<212> TYPE: PRT
<213> ORGANISM: Artificial Sequence
```

```
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 179

Gly Gly Gly Gly Gly Tyr Cys Asp Glu Gly Pro Thr Leu Lys Gln Trp
1               5                   10                  15

Leu Val Cys Leu Gly Leu Gln
            20

<210> SEQ ID NO 180
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 180

Gly Gly Gly Gly Gly Cys Ser Ser Gly Gly Pro Thr Leu Arg Glu Trp
1               5                   10                  15

Leu Gln Cys Arg Arg Met Gln
            20

<210> SEQ ID NO 181
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 181

Gly Gly Gly Gly Gly Cys Ser Trp Gly Gly Pro Thr Leu Lys Gln Trp
1               5                   10                  15

Leu Gln Cys Val Arg Ala Lys
            20

<210> SEQ ID NO 182
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 182

Gly Gly Gly Gly Gly Ala Leu Arg Asp Gly Pro Thr Leu Lys Gln Trp
1               5                   10                  15

Leu Glu Tyr Arg Arg Gln Ala Gly Gly Gly Gly Ala Leu Arg Asp
            20                  25                  30

Gly Pro Thr Leu Lys Gln Trp Leu Glu Tyr Arg Arg Gln Ala
        35                  40                  45
```

```
<210> SEQ ID NO 183
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 183

Gly Gly Gly Gly Gly Glu Ala Leu Leu Gly Pro Thr Leu Arg Glu Trp
1               5                   10                  15

Leu Ala Trp Arg Arg Ala Gln Gly Gly Gly Gly Glu Ala Leu Leu
            20                  25                  30

Gly Pro Thr Leu Arg Glu Trp Leu Ala Trp Arg Arg Ala Gln
        35                  40                  45

<210> SEQ ID NO 184
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 184

Gly Gly Gly Gly Gly Ala Val Pro Gln Gly Pro Thr Leu Lys Gln Trp
1               5                   10                  15

Leu Leu Trp Arg Arg Cys Ala Gly Gly Gly Gly Ala Val Pro Gln
            20                  25                  30

Gly Pro Thr Leu Lys Gln Trp Leu Leu Trp Arg Arg Cys Ala
        35                  40                  45

<210> SEQ ID NO 185
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 185

Gly Gly Gly Gly Gly Tyr Cys Asp Glu Gly Pro Thr Leu Lys Gln Trp
1               5                   10                  15

Leu Val Cys Leu Gly Leu Gln Gly Gly Gly Gly Tyr Cys Asp Glu
            20                  25                  30

Gly Pro Thr Leu Lys Gln Trp Leu Val Cys Leu Gly Leu Gln
        35                  40                  45

<210> SEQ ID NO 186
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus
```

<400> SEQUENCE: 186

Gly Gly Gly Gly Gly Cys Ser Ser Gly Gly Pro Thr Leu Arg Glu Trp
1               5                   10                  15

Leu Gln Cys Arg Arg Met Gln Gly Gly Gly Gly Cys Ser Ser Gly
            20                  25                  30

Gly Pro Thr Leu Arg Glu Trp Leu Gln Cys Arg Arg Met Gln
        35                  40                  45

<210> SEQ ID NO 187
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (1)..(1)
<223> OTHER INFORMATION: At position 1, Fc at N-terminus

<400> SEQUENCE: 187

Gly Gly Gly Gly Gly Cys Ser Trp Gly Gly Pro Thr Leu Lys Gln Trp
1               5                   10                  15

Leu Gln Cys Val Arg Ala Lys Gly Gly Gly Gly Cys Ser Trp Gly
            20                  25                  30

Gly Pro Thr Leu Lys Gln Trp Leu Gln Cys Val Arg Ala Lys
        35                  40                  45

<210> SEQ ID NO 188
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (47)..(47)
<223> OTHER INFORMATION: At position 47, Fc at C-terminus

<400> SEQUENCE: 188

Ala Leu Arg Asp Gly Pro Thr Leu Lys Gln Trp Leu Glu Tyr Arg Arg
1               5                   10                  15

Gln Ala Gly Gly Gly Gly Gly Ala Leu Arg Asp Gly Pro Thr Leu Lys
            20                  25                  30

Gln Trp Leu Glu Tyr Arg Arg Gln Ala Gly Gly Gly Gly Gly
        35                  40                  45

<210> SEQ ID NO 189
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (47)..(47)
<223> OTHER INFORMATION: At position 47, Fc at C-terminus

<400> SEQUENCE: 189

Glu Ala Leu Leu Gly Pro Thr Leu Arg Glu Trp Leu Ala Trp Arg Arg
1               5                   10                  15

Ala Gln Gly Gly Gly Gly Gly Glu Ala Leu Leu Gly Pro Thr Leu Arg
            20                  25                  30

Glu Trp Leu Ala Trp Arg Arg Ala Gln Gly Gly Gly Gly Gly

-continued

```
                35                  40                  45

<210> SEQ ID NO 190
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (47)..(47)
<223> OTHER INFORMATION: At position 47, Fc at C-terminus

<400> SEQUENCE: 190

Ala Val Pro Gln Gly Pro Thr Leu Lys Gln Trp Leu Trp Arg Arg
1               5                   10                  15

Cys Ala Gly Gly Gly Gly Ala Val Pro Gln Gly Pro Thr Leu Lys
                20                  25                  30

Gln Trp Leu Leu Trp Arg Arg Cys Ala Gly Gly Gly Gly Gly
            35                  40                  45

<210> SEQ ID NO 191
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (47)..(47)
<223> OTHER INFORMATION: At position 47, Fc at C-terminus

<400> SEQUENCE: 191

Tyr Cys Asp Glu Gly Pro Thr Leu Lys Gln Trp Leu Val Cys Leu Gly
1               5                   10                  15

Leu Gln Gly Gly Gly Gly Gly Tyr Cys Asp Glu Gly Pro Thr Leu Lys
                20                  25                  30

Gln Trp Leu Val Cys Leu Gly Leu Gln Gly Gly Gly Gly
            35                  40                  45

<210> SEQ ID NO 192
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (47)..(47)
<223> OTHER INFORMATION: At position 47, Fc at C-terminus

<400> SEQUENCE: 192

Cys Ser Ser Gly Gly Pro Thr Leu Arg Glu Trp Leu Gln Cys Arg Arg
1               5                   10                  15

Met Gln Gly Gly Gly Gly Cys Ser Ser Gly Gly Pro Thr Leu Arg
                20                  25                  30

Glu Trp Leu Gln Cys Arg Arg Met Gln Gly Gly Gly Gly
            35                  40                  45

<210> SEQ ID NO 193
<211> LENGTH: 46
<212> TYPE: PRT
<213> ORGANISM: Artificial Sequence
<220> FEATURE:
<223> OTHER INFORMATION: Synthesized Peptide Sequence
<220> FEATURE:
```

<221> NAME/KEY: misc_feature
<222> LOCATION: (47)..(47)
<223> OTHER INFORMATION: At position 47, Fc at C-terminus

<400> SEQUENCE: 193

Cys Ser Trp Gly Gly Pro Thr Leu Lys Gln Trp Leu Gln Cys Val Arg
1               5                   10                  15

Ala Lys Gly Gly Gly Gly Gly Cys Ser Trp Gly Gly Pro Thr Leu Lys
            20                  25                  30

Gln Trp Leu Gln Cys Val Arg Ala Lys Gly Gly Gly Gly
        35                  40                  45

<210> SEQ ID NO 194
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 194

Ala Leu Arg Asp Gly Pro Thr Leu Lys Gln Trp Leu Glu Tyr Arg Arg
1               5                   10                  15

Gln Ala Gly Gly Gly Gly Gly
            20

<210> SEQ ID NO 195
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 195

Glu Ala Leu Leu Gly Pro Thr Leu Arg Glu Trp Leu Ala Trp Arg Arg
1               5                   10                  15

Ala Gln Gly Gly Gly Gly Gly
            20

<210> SEQ ID NO 196
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 196

Glu Ala Leu Leu Gly Pro Thr Leu Arg Glu Trp Leu Ala Trp Arg Arg
1               5                   10                  15

Ala Gln Gly Gly Gly Gly Gly
            20

<210> SEQ ID NO 197
<211> LENGTH: 23
<212> TYPE: PRT

```
-continued

<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 197

Tyr Cys Asp Glu Gly Pro Thr Leu Lys Gln Trp Leu Val Cys Leu Gly
 1               5                  10                  15

Leu Gln Gly Gly Gly Gly Gly
            20

<210> SEQ ID NO 198
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 198

Cys Ser Ser Gly Gly Pro Thr Leu Arg Glu Trp Leu Gln Cys Arg Arg
 1               5                  10                  15

Met Gln Gly Gly Gly Gly Gly
            20

<210> SEQ ID NO 199
<211> LENGTH: 23
<212> TYPE: PRT
<213> ORGANISM: Artificial Sequence
<220> FEATURE:
<223> OTHER INFORMATION: Synthesized Peptide Sequence
<220> FEATURE:
<221> NAME/KEY: misc_feature
<222> LOCATION: (24)..(24)
<223> OTHER INFORMATION: At position 24, Fc at C-terminus

<400> SEQUENCE: 199

Cys Ser Trp Gly Gly Pro Thr Leu Lys Gln Trp Leu Gln Cys Val Arg
 1               5                  10                  15

Ala Lys Gly Gly Gly Gly Gly
            20
```